United States Patent
Fischell et al.

(10) Patent No.: US 9,174,057 B1
(45) Date of Patent: *Nov. 3, 2015

(54) CARDIAC EVENT DETECTION BASED ON SELECTIVE PACING FOR ESTABLISHING A PACED HEART SIGNAL PARAMETER BASELINE

(71) Applicant: ANGEL MEDICAL SYSTEMS, INC., Fair Haven, NJ (US)

(72) Inventors: David R. Fischell, Fair Haven, NJ (US); Michael Sasha John, Larchmont, NY (US); Bruce Hopenfeld, Salt Lake City, UT (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,249

(22) Filed: Nov. 3, 2014

Related U.S. Application Data

(63) Continuation of application No. 12/624,521, filed on Nov. 24, 2009, now Pat. No. 8,903,487.

(51) Int. Cl.
*A61N 1/00* (2006.01)
*A61N 1/37* (2006.01)
*A61N 1/362* (2006.01)
*A61B 5/0452* (2006.01)

(52) U.S. Cl.
CPC .............. *A61N 1/3702* (2013.01); *A61N 1/362* (2013.01); *A61B 5/0452* (2013.01)

(58) Field of Classification Search
CPC ............................. A61B 5/0452; A61N 1/362
USPC .................. 607/4, 5, 9, 14, 28; 600/508, 509, 600/515–518
See application file for complete search history.

(56) References Cited

U.S. PATENT DOCUMENTS 6,381,493 B1 * 4/2002 Stadler et al. ..................... 607/9

* cited by examiner

Primary Examiner — Christopher D Koharski
Assistant Examiner — Roland Dinga
(74) Attorney, Agent, or Firm — Rosenberg, Klein & Lee

(57) ABSTRACT

A device for detecting cardiac ischemia is disclosed. The device includes a processor that is configured to distinguish between two different heart beats types such as ventricularly paced beats and supraventricular beats. The processor collects separate reference data for a first one of the beat types indicative of the normal values of a cardiac feature. The processor performs an ischemia test to beats of the first type by first checking whether valid reference data exists for that beat type. If so, the ischemia test is based on this reference data. If no valid reference data exists for the firs beat type, the processor applies an ischemia test that is not based on reference data for the first beat type.

15 Claims, 22 Drawing Sheets

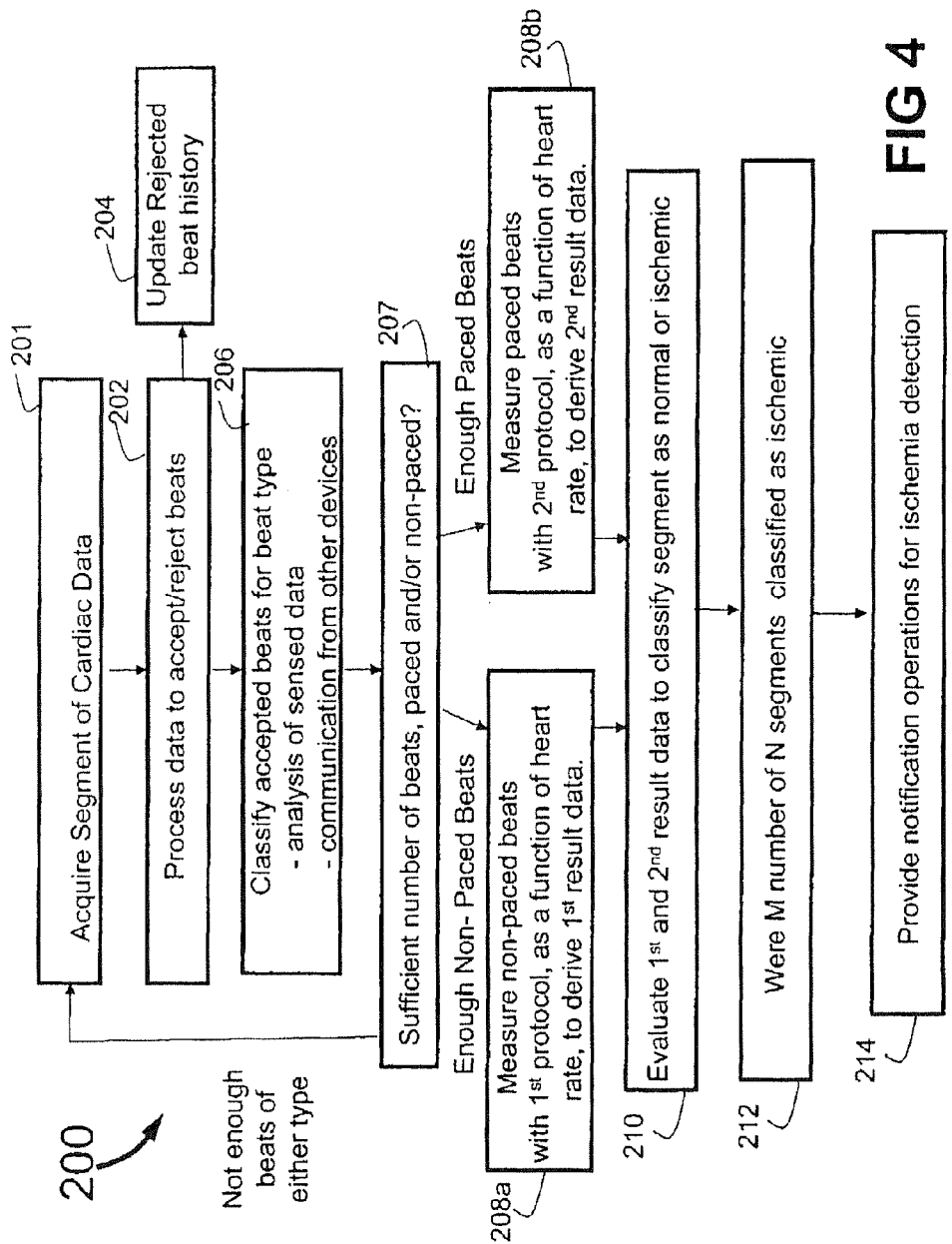

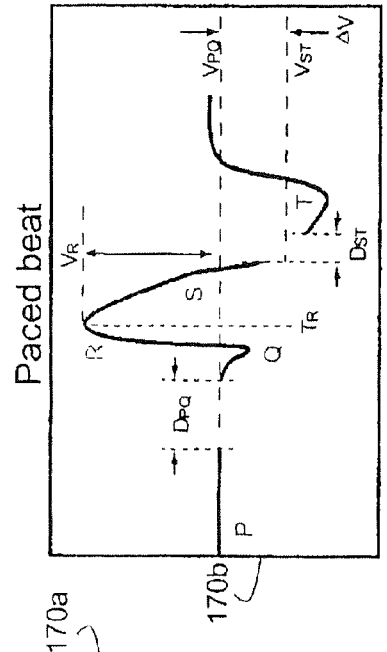
FIG 5B Paced beat
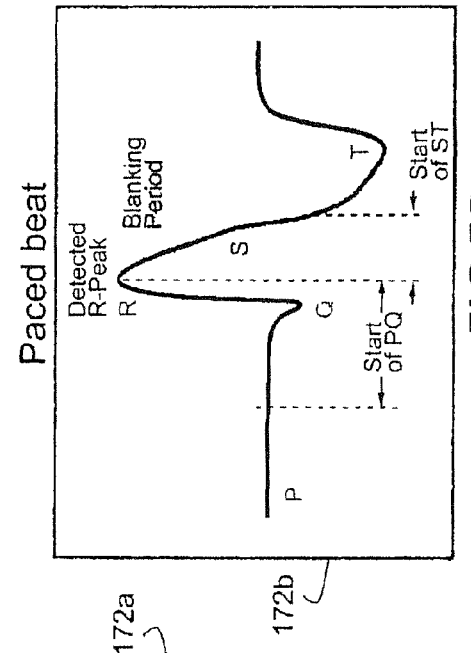
FIG 5D Paced beat
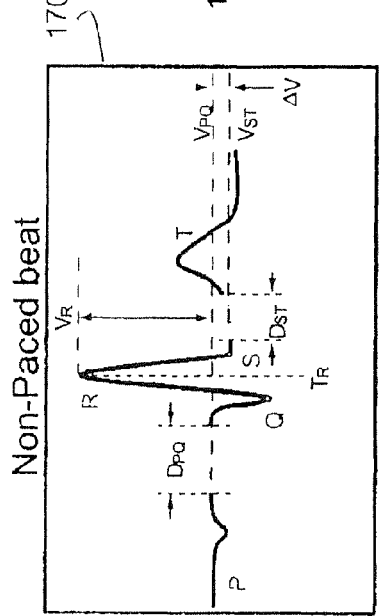
FIG 5A Non-Paced beat
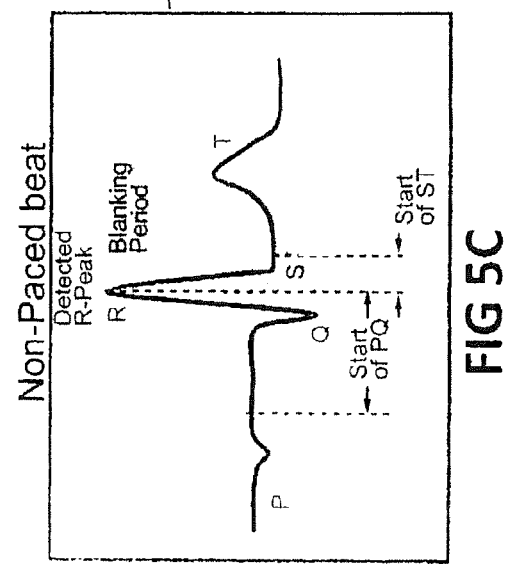
FIG 5C Non-Paced beat

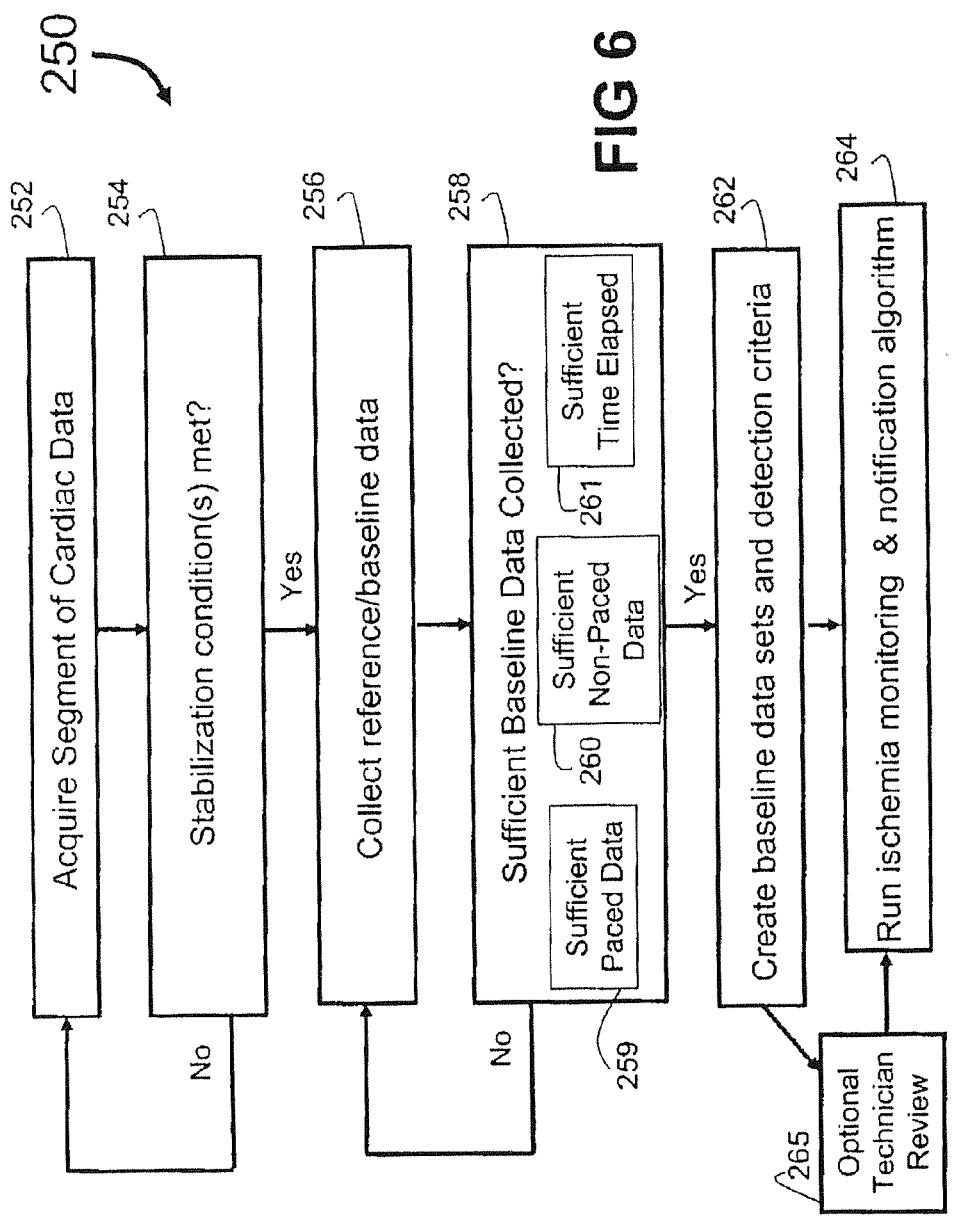

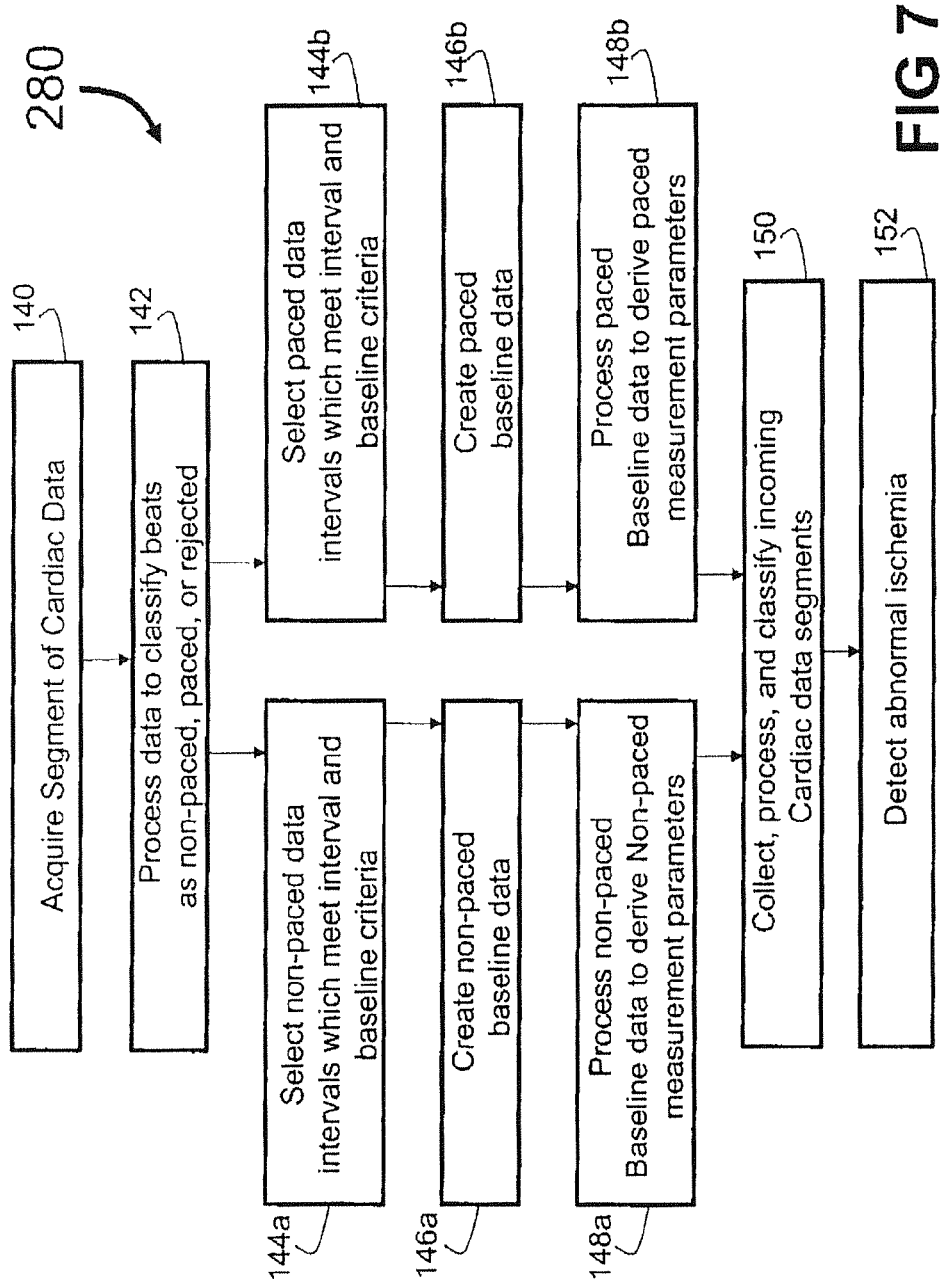

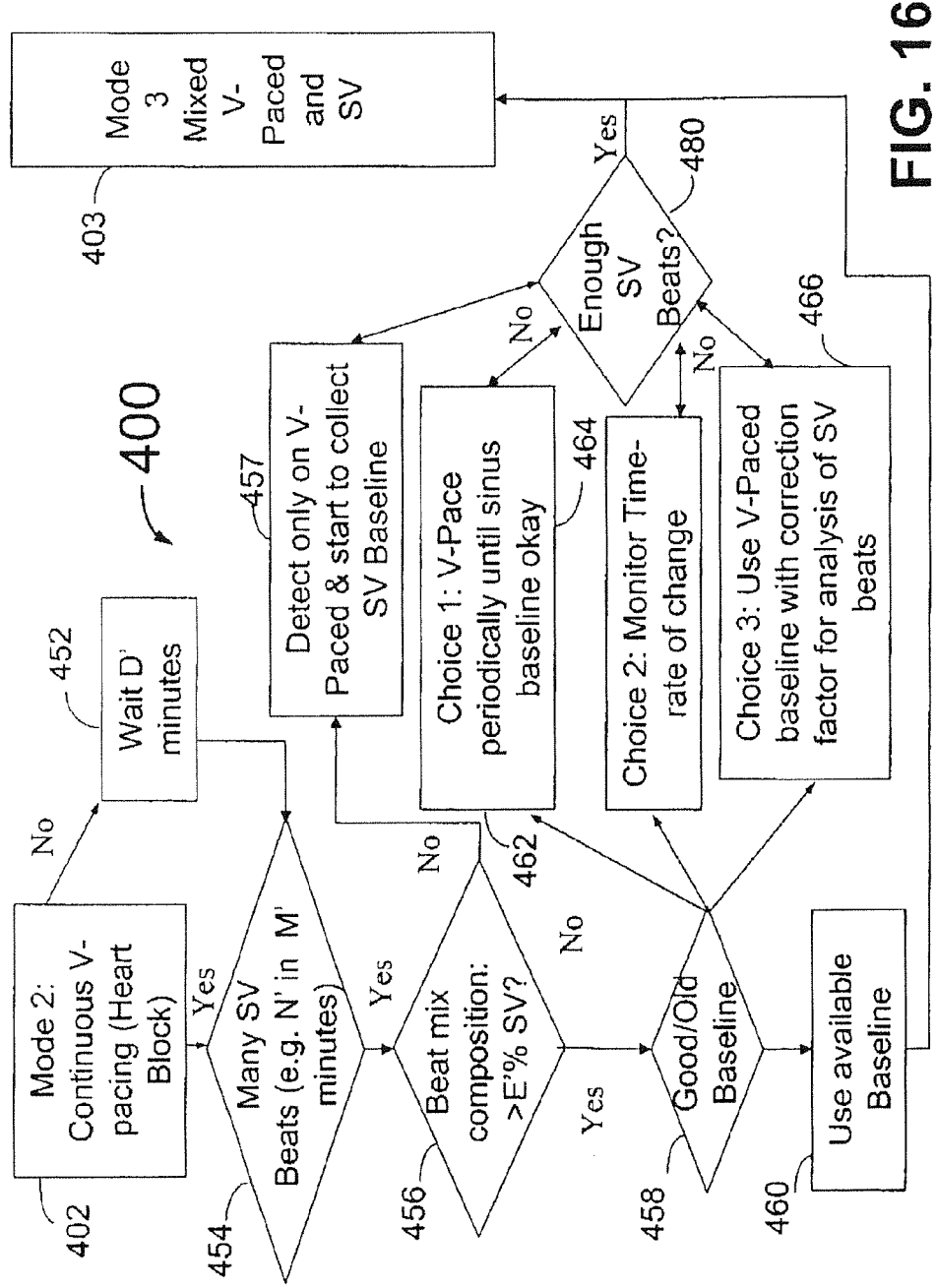

CARDIAC EVENT DETECTION BASED ON SELECTIVE PACING FOR ESTABLISHING A PACED HEART SIGNAL PARAMETER BASELINE

REFERENCE TO RELATED APPLICATION

This invention is based on patent application Ser. No. 12/624,521, filed 24 Nov. 2009, currently pending.

FIELD OF THE INVENTION

The invention is in the field of cardiac diagnostic devices and implantable cardiac pacemakers and resynchronization devices.

BACKGROUND

Implantable medical devices (IMD) that can alert patients or third parties to the detection of ischemic events including heart attacks (Myocardial Infarction) can save lives and reduce damage to a patient's heart tissue, improving the post-myocardial-infarction quality of life. Myocardial infarction (MI) occurs when a blood clot blocks the blood supply to a portion of the heart causing the heart tissue to become hypoxic (ischemic) and also experience decreased metabolite removal. Ischemia detection may occur by analysis of the patient's cardiac activity, especially via electrical waveforms sensed by electrodes.

The sino-atrial (SA) node normally serves as the pacemaker for the healthy human heart. Electrical pacing pulses travel through conduction pathways and cause electrical/chemical changes in adjacent myocardium, producing the coordinated activity of various regions which are associated with the beating of the heart and normal blood-flow. When the electrical conduction network of the heart becomes diminished, when there are factors which cause tissue damage, or when there is insufficient blood-flow supplying the heart itself, the timing of the propagating electrical signals will cause the heart to beat in a less efficient manner, to beat abnormally, or to not beat at all. The heart has back-up systems for beating when the SA node experiences failure, such as the atrioventricular node (AV node), which has a natural pacing rate that is slower than the SA node. Although the heart can somewhat compensate for abnormal pacing, providing artificial pacing in order to assist a sick heart deters the risk of further complications which may lead a patient to more quickly experience worsening levels of heart failure.

Most pacemakers are "demand pacemakers" which utilize sensing in order to only deliver pacing when the heartbeat is too slow. This feature allows pacing to not occur continuously and there may be both paced and non-paced heartbeats throughout the day. Pacemakers can also be "rate-responsive" and contain means for determining what the heart rate should be at different moments in time. Not only do they provide pacing when the heart rate drops below a selected minimum, but these can also set the rate of pacing to create a well adjusted heart rate. Rate-responsive pacemakers may rely upon multiple technologies and sensors to determine the appropriate heart rate. An accelerometer may serve as an activity sensor which detects the patient's level and direction of movement so that increased pacing rates may be provided when the patient is active. Additionally, various sensors may serve to measure breathing characteristics, such as rate, so that faster breathing will provide rate-responsive pacing more akin to that seen endogenously in patients with normal cardiac electrical systems. Additional sensors that measure indices such as carbon-dioxide or cardiovascular sounds can also be used to adjust pacing rate.

Pacemakers can have two or more stimulation leads which not only keep the heart rate from dropping too low, but also to maintain improved coordination between different chambers of the heart. For example, the atria and the ventricles can be made to cooperate better by pacing the structures sequentially and at a well chosen latency for a particular heart rate range. In a multiple lead pacemaker, the processor analyzes sensed cardiac data, and derives information that enables the pacemaker to determine if, when, and where to provide pacing to improve synchronization of the different chambers.

One type of multiple lead pacemaker is a "biventricular pacemaker", also known as CRT (cardiac resynchronization therapy) device. CRT devices can pace both the septal and lateral walls of the left ventricle in order to "resynchronize" a heart. A CRT device may utilize a first lead located in the right ventricle to provide septal stimulation while the second is routed through the coronary sinus and anchored to pace the lateral wall of the left ventricle. A third lead, positioned in the right atrium, may also be used to improve ventricular synchrony with the atrial contraction. The timing between the atrial and ventricular contractions, as well as between the septal and lateral walls of the left ventricle can be programmably adjusted to improve cardiac function in individual patients. CRT technology can be implemented within an implantable cardioverter-defibrillator (ICD). Medically dangerous rhythms such as certain arrhythmias can be halted by giving the heart an electric shock delivered using the ICD (e.g., within the heart itself or by stimulation sites in the chest wall) or external devices. Modern programmable pacemakers allow the medical personnel to select the optimum pacing modes for individual patients. The term "pacemaker" shall henceforth mean a system of one or more devices that provides one or more of pacemaker, CRT, cardioversion, and defibrillator capacity.

When therapies, such as electrical pacing of the patient's heart, occur concurrently with ischemia monitoring of the patient, the effects of these therapies both on the heart and on the sensed cardiac data must be managed by monitoring methods so that ischemia can be accurately measured from the sensed cardiac data.

The combination of a pacemaker or ICD with an ischemia detector is described by Fischell et al in U.S. Pat. Nos. 6,112, 116, 6,272,379 and 6,609,023. Fischell describes an IMD which can detect a change in the electrical signal from the patient's heart (cardiac electrical signal) that is indicative of a cardiac event, such as an acute ischemia, and then provide a notification of such an event. The IMD can also be a medical device which senses and/or stimulates cardiac, neural, vagal-nerve, or other anatomical target in order to control cardiac activity. Fischell also describes an external alarm system that can provide additional visual, sonic and vibratory alerting signals and may also provide voice/data communication between the IMD and a remote medical monitoring station.

SUMMARY

Systems and methods for monitoring ischemia in a patient who, at least sporadically, receives electrical therapy are described. Ischemia monitoring can lead to notification of the patient or a third party when certain events occur. Events may include, for example, measuring an abnormal level of ischemia in paced heart-beats, non-paced heartbeats, or both.

In one embodiment of the current invention, the choice of measured features for each heart beat, are different as a function of beat type for the paced and non-paced heartbeats. Alternatively, the measured features for each heart beat are the same for both beat types, but the measurement protocol for deriving each feature varies according to beat type. Further, assessment of ischemia is contingently adjusted based upon beat type. When segment-based ischemia detection as described by Fischell in U.S. Pat. No. 6,609,023 is utilized, the number of segments, or other segment-based criteria used to determine if ischemia-related alerting should occur can vary according to the composition of beat types (e.g. proportion of each type of beat) distributed within the segments.

In another aspect, reference values and baseline data to which current beats are compared are operated upon as a function of beat type. Baseline data may be collected at particular intervals or times or in relation to pacing parameters such as pacing schedules and rates and types of pacing. Reference data may be obtained as a function of the pacing program that is implemented by a device. If insufficient paced beats are available over a pre-set baseline period then the IMD may be turned on to pace the heart for a period of time even if pacing is not otherwise required so that a sufficient number of paced beats can be analyzed for use as a baseline for ischemia detection in future beats where pacing is required.

In another aspect the period of ischemia monitoring is contingently delayed, aborted, extended or otherwise adjusted based upon the provision of pacing. Adjustment of monitoring can also occur in relation to a recent history of pacing either alone or in conjunction with a consideration of endogenous cardiac activity. Adjustment of monitoring can also occur in relation to what baseline data is available for a particular beat type. Adjustment of monitoring can include increasing the amount of time that sensing occurs so that instead of monitoring N of every M seconds, for example, monitoring may be extended to the full M seconds until a sufficient amount of acceptable data is obtained to monitor ischemia.

In another aspect the ischemia monitoring may be adjusted based upon the occurrence, or anticipation, of pacing which may be inferred from the analysis of cardiac data which is sensed.

In another aspect the implantable ischemia monitor may contain a pacing system that delivers pacing pulses. In another aspect the monitor may be used in a patient where the pacing is provided by an independently operated pacemaker, which may or may not be configured to cooperate or communicate with the ischemia monitoring device.

In another aspect, the ischemia monitor may adjust the pacing provided by an implanted pacemaker based upon ischemia related measurements, ischemia related levels defined for that patient, recent history of ischemia measurements, detection of ischemic beats, or the detection of a medically relevant ischemic episode which is sufficient to require alerting or sending data so that appropriate medical intervention can be supplied.

In another aspect, device operation including, for example, the measurement of beat features, assessment of features in relation to ischemia, baseline and reference data collection, and alerting operations, can be adjusted in relation to current or historical presence of paced and non-paced beat types. Further, paced and supraventricular beat types can be further classified into subtypes, such as type of pacing provided and normal or abnormal beat types. The type of pacing which occurs may also be used to adjust monitoring operations, whereby if a specific type of pacing has not been indicated for the patient during device programming, then the monitoring program will use a monitoring protocol that does not incorporate this type of paced-beat. In other words, ischemia monitoring protocols can be selected or adjusted in relation to pacing protocols. For example, don't ever try to analyze data using a protocol designed for two leads if only 1 lead provides pacing in that patient.

In a further aspect, the monitoring device contains a pacing module which contains the ability to operate upon sensed cardiac data to determine if pacing should be provided and to operate a stimulation subsystem to provide pacing according to a pacing protocol. The parameters of the pacing protocol may be further modified according to the ischemia detection operations and monitoring operations, and vice-versa.

In a further aspect, when the monitoring device does not contain provisions for pacing, a pacing module of the monitoring device assists with interaction between the monitoring device and other devices that provide pacing to the patient (e.g., to obtain a wired or wireless communication about provision of pacing), in order to determine if, when, and what type of pacing has been, is, or will be, provided by this other device. For example the programmer of the monitoring device can detect pacing devices or interact with their programmers, to obtain the pacing protocol and a history of pacing for a particular patient. Additionally, the pacing module of the monitoring device contains the ability to operate upon sensed cardiac data to determine if pacing has been provided, by a separate pacemaker device and to adjust monitoring operation accordingly.

Lastly, in one embodiment, the present invention classifies three modes of ischemia monitoring based on the pacing protocol being used for the patient. The first is a mode that is oriented for ischemia monitoring when ventricular pacing is rarely provided, such as for treatment of syncope. The second mode is used when ventricular pacing is continuous or provided frequently, such as in the case of heart block. The third mode is used when ventricular pacing is provided such that there are both relatively frequent intervals of paced and non-paced beats. Further, the mode which is used can be programmed by a doctor or can be adaptively selected by the device based upon the history of pacing of the patient as recorded in the device's memory.

The primary functionality of the present invention has ischemia detection capability for both paced and non-paced beats, can identify the pacing prevalence for the patient and consequently select one of the ischemia monitoring modes listed above and operates as follows for each mode.

In the case of mode 1, ventricular pacing is rare and occurs typically only for a short time, e.g. less than 10 minutes at a time and less than an hour a day. Pacing in this mode may be to prevent fainting from an episode of syncope. When ventricular pacing is rare, the primary ischemia detection technique is to process only supraventricular beats and ignore ventricularly paced beats. Because any real ischemic event such as a heart attack from a blocked coronary artery will produce electrogram or electrocardiogram changes that may last for tens of minutes or even hours, ignoring a small number of paced beats during, for example, rare periods of syncope will not create significant delays in detection and alerting.

For mode 2 where ventricular pacing is pretty much continuous, one can ignore supraventricular beats when they occur.

For mode 3 the present invention must separately run detection algorithms for both ventricularly paced and supraventricular beats so that it can identify an ischemic event either from a single beat type or by sufficient changes in both beat types using detection protocols having any of the following: different detection criteria, different algorithms for detection and/or different thresholds for detection. In this mode there would typically be more than 30 minutes a day of both paced and non-paced beats with episodes of both paced and non-paced beats that exceed 10 minutes. One significant aspect of the present invention pertains to mode 3 pacing and deciding when to transition the ischemia detection scheme between modes, such as from mode 1 or mode 2 to mode 3. One embodiment of the present invention uses an ischemia detection algorithm such as that of Fischell in U.S. Pat. No. 6,069,023 where calculated heart signal parameters from newly collected beats of the heart signal are compared to baseline data collected at a prior time period when the heart signal was "normal". The essence of this algorithm is the collection of this baseline heart signal parameter data during "normal" heart activity. In this embodiment the present invention can decide to process beats of the heart signal to extract baseline heart signal parameter data whenever the signal has a sufficiency of "normal" beats over a period of time, for example at least 10 supraventricular beats over a 5 minute period. Similarly it can process ventricularly paced beats to extract baseline heart signal parameter data for paced beats if the signal has a sufficiency of "normal" paced beats over a period of time, for example at least 10 paced beats over a 5 minute period. This baseline ventricularly paced and supraventricular heart signal parameter data can be collected periodically (e.g. once an hour) and averaged together over a longer period (e.g. a day) to create the current paced and supraventricular heart signal parameter baseline data against which the heart signal parameter data of new beats are compared. Heart signal parameters for new paced beats being compared to the paced beat baseline data and heart signal parameters for supraventricular beats being compared to the supraventricular baseline data.

It is envisioned that if an insufficient number of supraventricular beats occur over a period of time, the algorithm can revert to mode 2 and ignore supraventricular beats until there are enough to establish a new baseline. Alternately this can occur when the baseline data for supraventricular beats becomes too old (e.g. has had no new data added for 3 days). Until then the old baseline may still be used.

A similar technique can also be used if there is an insufficiency of ventricularly paced beats where the algorithm would revert to mode 1 and ignore ventricularly paced beats until there are a sufficiency to establish a new baseline. Alternately, the present invention can cause the heart to be periodically ventricularly paced (even if not needed) so that ventricularly paced baseline data can be collected. For example, if once every hour if there are no ventricularly paced beats, the present invention can using its own or adjunctive pacing means pace the right ventricle (and perhaps the left ventricle) for 10 seconds at a rate just slightly higher than the native heart rate. The patient should feel no discomfort when this occurs and the system will be able to collect paced beat heart signal parameter data for use in the ventricularly paced baseline.

Another feature of the present invention involves the selective application of time rate of change information to test for ischemia. Time rate of change ischemia tests are disclosed in U.S. patent application Ser. No. 11/898,673, filed 9/2007, entitled "Waveform Feature Value Averaging System and Methods for the Detection of Cardiac Events", and owned by the assignee hereof; and U.S. provisional patent application 61/152,367, filed 2/2009, entitled "Time Series Tracking System and Methods for the Detection of Cardiac Events", filed 2/2009 and owned by the assignee hereof, and U.S. patent application Ser. No. 12/461,442 entitled "Heart Rate Correction System and Methods for the Detection of Cardiac Events", filed 8/2009 and owned by the assignee hereof (collectively, "Rate of Change Applications") The present invention separately examines paced and non-paced beats, calculate the time rate of change separately for each, and compare the rate of change with separate detection thresholds. It is also envisioned in this embodiment, the heart signal parameter(s) could be different or could be calculated differently for paced vs. non-paced beats. For example, the time rate of change of ST segment voltage could be used for non-paced beats while the time rate of change of QT time could be used for paced beats. It is also envisioned that the system can be examining the time rate of change of more than one heart signal parameter for either or both paced and non-paced beats. For example, time rate of change of ST voltage could be used for non-paced beats and both time rate of change of ST voltage and QT time could be used for paced beats or vice versa. It is also envisioned that the location of the ST segment or other heart signal features in relation to the R wave or another reference heart signal feature can be determined differently for paced and non-paced beats. Since paced beats have a wider QRS width than normal non-paced beats, it is envisioned that the ST segment for paced beats occurs later after the R wave than for non-paced beats. For example the ST segment might for a 60 bpm heart rate be 30 ms long and 50 ms after the R wave for a non-paced beat and 20 ms long and 70 ms after the R wave for a paced beat.

In all of the above modes the current invention will ignore fusion beats where it is unclear whether the beat is paced or non-paced as these are rare enough so that there will still be enough other beats on which to measure ischemia.

The described invention addresses the shortcomings of medical ischemia monitoring systems that do not monitor, adjust in response to, or compensate for the provision of electrical therapy such as pacing. Further, pacing devices which do not modify their operation based upon ischemic measures may provide less than optimal pacing therapy. Additionally, the invention provides the advantage of adjusting ischemia detection parameters based upon the types of beats which are present in cardiac data in order to more accurately provide ischemia monitoring and detection of medically relevant ischemic events.

Thus it is an object of the present invention to have a combination pacemaker/ischemia detection system capable of identifying the mode of pacing present over any period of time and applying appropriate ischemia detection rules based on the mode of pacing.

Another object of the present invention is to ignore ventricularly paced beats if the primary pacing mode is one in which ventricular pacing is rare.

Still another object of the present invention is to ignore supraventricular (e.g. sinus) beats if the primary pacing mode is one in which ventricular pacing is continuous.

Still another object of the present invention is in the case of significant numbers of both ventricularly paced and supraventricular beats to separately process each beat, applying different ischemia detection criteria to each type of beat.

Yet another object of the present invention is to identify an acute ischemic event based on a sufficient change in either ventricularly paced or supraventricular beats.

Yet another object of the present invention is to be able to identify an acute ischemic event based on a combination of changes in both paced and non-paced beats.

This summary does not provide an exhaustive disclosure of the present invention.

Accordingly, these as well as other objects and advantages of the current invention will now be described in the description of the figures, the detailed description of the invention, and the claims.

BRIEF DESCRIPTION OF THE FIGURES

FIG. 4 shows a method for measuring ischemic related features of both paced and non-paced beats in order to detect ischemia using a segment based detection scheme.

FIGS. 5A and 5B show ventricular paced and supraventricular beat types, respectively, with sample cardiac features measured in the two types of beats.

FIGS. 5C and 5D show ventricular paced and supraventricular beat types, respectively, with sample protocol parameters which are used to measure heart-beat features in the two types of beats, such as defining blanking intervals.

FIG. 6 shows a method for creating two different types of baselines which can serve as a self-normative reference for paced and non-paced beats.

FIG. 7 shows a method for ischemia monitoring which includes obtaining baselines and measuring features in both paced and non-paced beats for baseline reference data, and then collecting, processing, and comparing the measured features of current data for each beat type to their corresponding baselines in order to classify cardiac data and detect abnormal ischemia.

FIG. 16 shows steps of a method used to transition from Mode 2 in which ventricular pacing occurs frequently to Modes 1 or 3 when the pattern of ventricular pacing changes for a patient.

DETAILED DESCRIPTION OF THE INVENTION

In this application, "pacing" generally refers to ventricular pacing, and sinus or non-paced beatsgenerally includes beats of supraventricular origin, including atrially paced beats without subsequent ventricular pacing. However, the teachings of the present invention are applicable to any number of different beat types, in which case normal/sinus beats (as that term in used in the application) generically refers to type A beats, and paced beats (as that term in used in the application) generically refers to type B beats.

Figure 1:
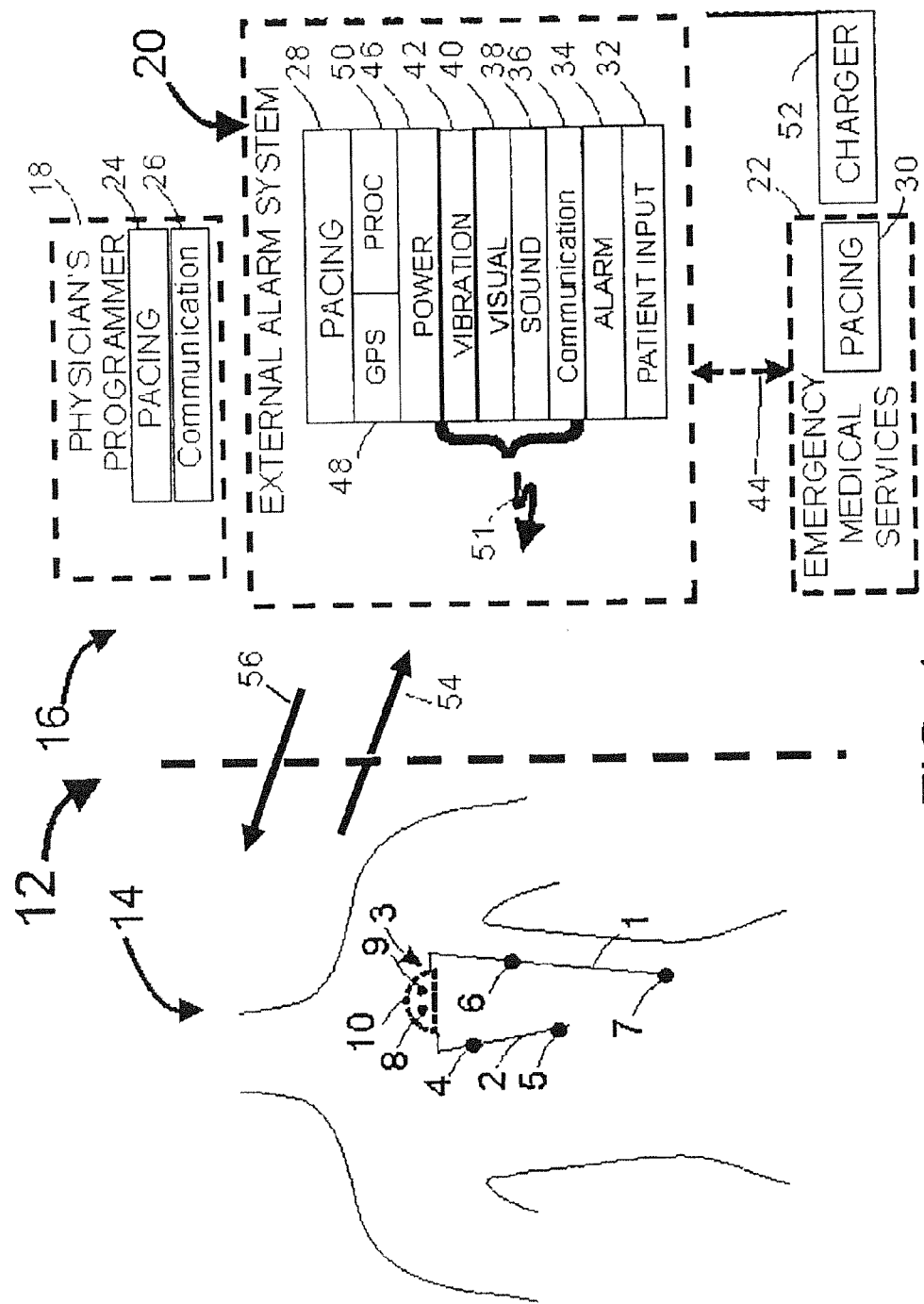
FIG. 1 shows a system which uses a single device having both ischemia monitoring and pacing capability.

FIG. 1 illustrates an example of a medical system 12 including implanted components 14 and external equipment 16. The implantable medical device (IMD) 3 includes sensors to monitor a cardiac condition associated with a patient. Electrode sensors can measure cardiac activity, neural activity, vagal activity, respiratory activity or other electrical activity which can influence cardiac function and demand. A microphone sensor can measure sonic data related to the patient (e.g. cardiac or respiratory sounds), an accelerometer can measure movement, acceleration or position, and a biosensor can measure metabolite levels within the patient. In one embodiment, sensors include the electrodes 4 and 5 incorporated into an insulated electrical wire lead 2. The lead 2 is electrically connected with the IMD 3. Through this connection the IMD that includes battery-powered sensing electronics receives signals from the electrodes 4 and 5. The connection may be of a custom design or preferably use a standardized pacemaker connector such as an IS1. The lead 2 with electrodes 4 and 5, can be placed subcutaneously or within the heart. It is also that the lead 2 could have only one electrode or a many as sixteen. When multiple electrodes are used, the cardiac features for the beats sensed in the data from each electrode may be measured using a protocol specific to each electrode. Further, baselines may be collected and analyzed for each electrode and ischemia detection thresholds may be defined for data sensed at each electrode. During ischemia monitoring the data from each electrode can be evaluated using multivariate methods, where data from each electrode is evaluated to produce an ischemia score, or the data may be combined using "and" or "or" logic by the ischemia detection algorithm. The implantable cardiac monitoring device can include a set of leads which are referenced to each other or to the case 10 of the IMD 3. In a preferred embodiment, the lead 2 is situated with the electrode 5 attached to the endocardium at the right apex of the patient's heart. In an alternative embodiment the electrodes 4 and 5 may be embedded under the patients skin, or may be any combination of implanted intracardiac and extracardiac locations in order to collect cardiac data both within and external to the heart. The lead 1 includes sensors 6 and 7. The sensors 6 and 7 may be additional intracardiac or extracardiac electrodes, microphones, optical sensors, accelerometers, or may be biosensors or chemical sensors that detect the presence or concentration of a biological substrate, medication, or metabolite. The lead 1 connects to the IMD3 providing signals from the patients body produced by the sensors 6 and 7.

IMD case sensors 8 and 9 could be situated within surface of the case 10 without any wire leads extending from the IMD 3. The case 10 which is typically a thin metal can constructed from a titanium can also serve as a sensing electrode providing electrode-to-can or can-to-electrode sensing for the electrodes 4 and 5, by being connected to one end of a differential amplifier circuit in the sensing electronics of the IMD 3. The IMD 3 may also include pacing electronics designed to electrically stimulate the patient's heart in an currently known form of pacing including single chamber pacing, dual chamber pacing, fixed rate pacing, variable rate pacing, AV pacing and cardiac resynchronization (CRT). The IMD 3 can provide pacing through the electrodes 4 and 5 of the lead 2, through the electrodes 6 and 7 of the second lead 1, both leads or a third lead (not shown). When sensors 4, 5, 6, 7, 8, and 9 are all electrodes, these can be configured with respect to the stimulation and sensing subsystems of the IMD 3 in order to provide stimulation, sensing, or both. Electrical stimulation, for example, using electrodes 8 and 9 which may stimulate referenced to each other or to the can 10, can also be used to provide an electric tickle for alerting purposes. In one embodiment the lead 2 in FIG. 1 could contain a sensor 5 that is advantageously placed through the patient's vascular system and into the apex of the right ventricle in order to monitor cardiac activity. When the lead 2 contains a sensor 5 such as a pressure or optical sensor, the lead 2 will have multiple conductive pathways for providing power to the sensor 5 and receiving data from the sensor 5.

FIG. 1 also shows external equipment 16 designed to communicate with the IMD 3 that may include: 1. a physician's programmer 18; 2. an external alarm system (EXD) 20 which may be implemented as one or more of: a pager-type device, a cell phone or PDA type device or a desktop unit; and, 3. a remote monitoring center 22. The physician's programmer 18 has 2-way wireless communication 26, with antenna, for communication between the programmer 18, the IMD 3 and the EXD 20. The EXD 20 includes a communication module 36 having one or more antenna for wireless communication with the IMD 3, Physician's Programmer 18 and remote monitoring center 22. The Physician's Programmer 18 provides users with the capability of interacting with the IMD 3, for operations including programming and retrieving data from the IMD 3. The EXD 20 also provides external alarm signals for alerting the patient and allows two way wired or wireless communication with the remote monitoring center 22. The remote monitoring center 22 can be one or more third parties including a monitoring service, the patient's doctor, or other intended target.

The programmer 18 shown in FIG. 1 can be used to communicate with the IMD 3 in order to adjust operational parameters related to, for example, pacing protocols and parameters, data collection, measurement of cardiac features in sensed data, event detection, data storage, and alerting protocols. Communication can include wireless signals 56 sent from the programmer 18 communications module 26 to the IMD 3 and or incoming wireless signals 54 sent from the IMD 3 to the communications module 26 of the programmer 18. The programmer 18 has a pacing module 24 which provides functionality related both to pacing of the patient and also to monitoring of ischemia in patients for which the IMD 3 provides pacing. For example, the pacing module 24 can be configured to:

1. Adjust pacing and ischemia monitoring protocols used in the IMD 3. The pacing module 24 can be used to command the IMD 3 to perform a particular pacing protocol and a particular type of ischemia monitoring protocol which can be adjusted based upon the pacing protocol. In one embodiment, the programmer 18 can download a history of pacing provided to the patient from the IMD 3, and this can be used (either alone or in conjunction with analysis of sensed data of paced and un-paced beats) to enable a medical professional to adjust a monitoring protocol for improved ischemia monitoring of the patient (e.g., see FIG. 8).
2. Adjust parameters used to measure features of paced and non-paced beats, and adjust criteria used to assess these features in relation to ischemia. For example, the pacing module 24 also has software routines that provide the medical professional with an interactive graphical display for viewing and or measuring paced beats, such as setting start and stop times for the measurements of ST-segments of paced and non-paced beats. Further, the displays can be used to adjust thresholds used for determining ischemia in these two different beat types (e.g., see FIGS. 5A-5F).
3. Synchronize pacing and associated monitoring information between the programmer and other system components. The programmer's pacing module 24 also permits medical professionals to adjust protocols stored in the pacing module 28 of the EXD 20 and pacing module 120 of the IMD 3 (see FIG. 3) which are related monitoring, pacing, communication of data, and patient alerting in a patient who receives pacing therapy. The modules 24, 28, and 120 may operate jointly and are configured with routines that allow these modules to synchronize or update each other's information and parameter settings according to device operation or as implemented by a medical practitioner who operates the devices 18, 20. The remote monitoring center 22, is provided with a pacing module 30. The various pacing modules of the system are provided with routines for interfacing with each other in order to communicate, set, and synchronize parameters as may be required by an individual patient's monitoring and pacing needs (e.g., see FIG. 11 where the "synchronize system components" button allows for at-will synchronization of system components, although this normally occurs automatically when the IMD 3 is programmed).

In FIG. 1, the EXD 20 and its pacing module 28 may be provided with some or all of the features described for the pacing module 24 of the Programmer, but are generally more limited to features which are useful for a patient. The EXD 20 has a patient input module 32 which contains a series of physical controls such a buttons. A "patient initiate" button can allow for the initiation of communication between the EXD 20 and the IMD 3. An "alarm disable" button can be used to cause an alarm of the IMD 3 and/or EXD 20 to halt rather than repetitively and needlessly re-alerting a patient. A "panic" button can allow a patient to send an alarm with or without attached data from the IMD 3 to a remote monitoring center 22, even in the absence of IMD 3 or EXD 20 alarm notification. An "event" button can allow patients to tag events and thereby cause data to be tagged and/or sent remotely. An alarm module 34 can operate the communication module 36, sound module 38, visual module 40, and vibration module 42, to create an alarm signal 51 that comprises at least one of: communicating with a $3^{rd}$ party, a sonic alarm, a visual alarm, and a vibration alarm, respectively.

The communication module 36, with the one or more antennae, provides near-field and far-field wireless communication. The near-field communication may use inductively coupled wake-up type communication methods such as are well known while medium and far-field communication may rely upon other means. The communication module 36 can employ standardized wireless methods such as Bluetooth, WiFi, the FCC medical band., and/or cellular communications system such as GSM, CDMA, TDMA. The communication module 36 allows for data and/or voice transmission to and from the medical monitoring center 22 via the communication link 44, and also allows communication with the IMD 3 and programmer 18. The sound module 38 has both sound input and output such as a microphone, and speaker, respectively and associated electronics for providing two-way voice communication with the remote monitoring center 22. Examples of external auditory alarm signals 51 include a periodic buzzing, a sequence of tones and/or speech which may be a pre-recorded message that instructs the patient as to what is happening and what actions should be taken or which may be real speech communicated by the remote monitoring center 22. The visual module 40 can include 1 or more colored diodes which are activated continuously, periodically, or according to a pattern that is associated with a particular alarm type. The visual module 40 may also include a display screen for displaying waveforms, pictures, and text related to system parameters, alarm information, or information related to pacing or ischemia monitoring. Patients may use navigation buttons provided by the patient input module 32 in order to navigate through menus presented on the display of the visual module 40 and to select desired menu options. Alternatively, the display of the visual module 40 may have a touch sensitive display that allows for patient input. The vibration module 42 can contain a vibration motor to produce the vibration alarm signal component of the alarm signal 51, and can also contain an accelerometer which can be used to test the vibration alarm and also to measure a patient's physical activity level when the EXD 20 is worn by the patient.

The patient can select a communication protocol from a menu presented on the display of the visual module 40, the various protocols being defined in pacing module 28 which are related to pacing provided by the IMD 3. The patient can then place the EXD 20 within range of the IMD 3 and initiate communication (e.g., by pushing the patient initiate button). This causes the EXD 20 to establish communication with the IMD 3, using its communication module 36, about a pacing related operations, the communication including, for example, obtaining statistics about pacing operations or monitoring of cardiac activity from a patient in which pacing is available. The pacing module 120 of the IMD 3 (see FIG. 3), can provide the pacing related data back to the EXD 20, which can be analyzed, stored, or displayed under direction of the pacing module 28.

The processing module 50 of the EXD 20 contains a real time clock or timer and other components which are normally available in the processing modules of current art portable smart-devices and pagers. Further, in a preferred embodiment, the EXD 20 is realized using a smart-phone (e.g., an iPhone, Blackberry or Palm), which may, if necessary, be implemented using specialized software and/or smartcards including means for wireless communication with the IMD 3. The alarm module 34, as well as the other modules of the EXD 20, may be implemented in hardware or software and contains all of the necessary components to implement alarming of the patient and/or remote station. The alarm module 34 collaborates with the processor module 50 to provide alerting by providing instructions to the processor or by receiving commands from the processor which cause it to implement alerting as defined in the alarm protocols, or both.

If an alarm notification is sent from the IMD 3 to the EXD 20, via the 2 way communication modules 36, 124 then the alarm module 34 can alert the patient, alert a 3$^{rd}$ party, or no alarm may be provided and the EXD 20 is simply operated to send data to a 3rd party for evaluation or storage. When the detection of a life threatening event (e.g., AMI or arrhythmia) is the cause of the alarm, the EXD 20 could automatically notify remote monitoring center 22 that a serious medical condition has occurred, an ambulance could be sent to treat the patient and to bring him to a hospital emergency room or directly to a catheterization laboratory. The pacing module 30 of the remote monitoring center allows the processing and display of paced data such as pacing parameters, pacing history, and other information that it may receive. The pacing module 30 may also allow remote adjustment of selected pacing parameters within selected ranges, such as the ability to change a mode of pacing.

If communication with remote monitoring center 22 occurs, then the message sent over the link 44 may include at least one of the following types of information as previously stored in the memory provided within the EXD's processor module 50 or as directly uploaded from the IMD 3: (1) What type of medical event has occurred, (2) the patient's name, address and a brief medical history, (3) a GPS coordinate and/or directions to where the patient is located (using the GPS satellite or cellular grid information as per GPS module 48), (4) patient data, historical monitoring data, and the data that caused the alarm (5) continuous real time data as it is collected after the alarm, and (6) pacing related information such as parameters, protocols, and recent history of pacing that has been provided to a patient. The EXD 20 may use a charger 52 to charge a rechargeable power supply 46 in the EXD 20.

Figure 2:
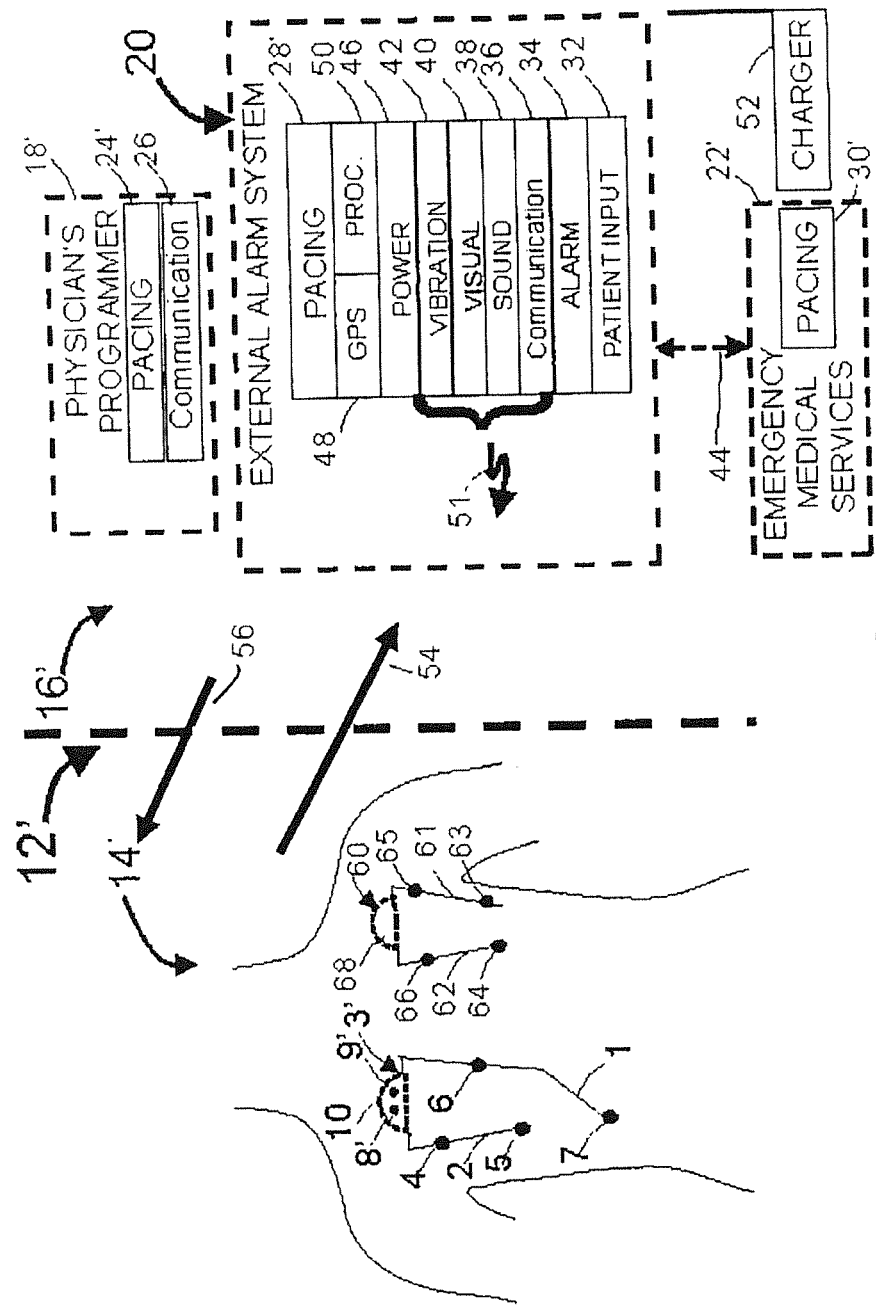
FIG. 2 shows an implanted device that has ischemia monitoring and is separate from a pacemaker device which is also implanted. (e.g., Subq)

The term "pacing" refers primarily to electrical pacing of the patient's heart. However, pacing can also be a therapy which relies upon chemical, mechanical, magnetic, or optical stimulation of tissue that result in heart beats that have distinct electrical characteristics. In the IMD 3 of FIG. 1, pacing is provided by the same IMD that monitors ischemia. The system 12 may also be implemented using multiple IMDs, stimulators, or sensors, which can be intracardiac, subcutaneous, and the system may be under control of a master IMD that controls subservient components of the system. Rather than using an IMD, the system 12 can use one or more devices that are external to the patient to provide pacing. As shown in FIG. 2, the IMD 3 may monitor ischemia in a patient who also has a generic pacemaker implanted which may, or may not, be designed to cooperate with the IMD 3.

FIG. 2 illustrates an alternative embodiment of a medical system 12' including internal components 14' and external equipment 16'. The IMD 3' includes sensors to monitor a cardiac condition associated with a patient such as ischemia. For example, electrode sensors can measure cardiac activity, neural activity, vagal activity, or other electrical activity of the body including pacing pulses provided by a pacemaker device 60. In one embodiment, sensors can include an insulated electrical wire lead 2, which is used to sense cardiac data that contains both paced or non-paced beats. The lead 2 can be configured with electrodes 4 and 5 which can be placed within the heart. Alternatively, the lead 2 may be subcutaneous if lead 62 from the pacemaker 60 is situated in the heart so that electrodes 64, 66 may provide pacing pulses. If the pacemaker provides pacing using two leads (dual chamber pacemaker) it may also contain lead 62 and electrodes 63 and 65, or the single lead 62 may be bifurcated to provide electrodes to different regions of the heart. While the IMD 's sensors may be in the apex of the right ventricle or can be located subcutaneously, in one preferred embodiment, the device will have at least one sensor in the heart and one outside, which is in addition to the IMD itself (i.e., the "can") and which may even be a sensor which is external to the patient, such as a cutaneous sensor that cooperates with the IMD 3'. When more than one sensor is used then the detection of ischemia may require that ischemic beats be detected at both of the two or more sensors. The ischemic beats may be measured across two or more sensors using "or" and "and" logic, where the evaluation which occurs in step 188*b* of FIG. 8, can require ischemic beats to be detected by one or more sensors. Generalizing this principle, the ischemia detection criteria, beat type criteria, fusion beat criteria, and data quality criteria may be implemented using information sensed at more than one sensor.

Stimulator/sensor 9' can be configured to provide defibrillation, sensing, or both. Sensor 9' can be configured as connector port which receives digital or analog signals from a communication cable (not shown), which extends from the pacemaker's housing 68 and which may be used to enable the pacemaker 60 to communicate with the IMD 3' about when, if, and what type of pacing is being provided.

FIG. 2 also shows external equipment 14' that consists of: 1. a physician's programmer 18'; 2. an external alarm system EXD 20'; and, 3. a remote monitoring center 22' which are configured to work with an IMD 3' that is designed to work with a patient in which a pacemaker 60 is also implanted. The physician's programmer 18' can be used to program the IMD 3' in order to adjust parameters related to data collection, event detection, data storage, alerting protocols, monitoring of paced and non-paced beats, and other information related to device operation. The programmer 18' also allows for the information retrieval from the memory of the IMD 3', such as information sensed data, and summary statistics which may be tagged or organized in relation to beat type. The programmer 18' has a pacing module 24' which provides functionality related to monitoring ischemia in patients for which the pacemaker 60 provides pacing. The pacing module 24 can be configured to command the IMD 3 to perform a particular type of monitoring protocol which can be adjusted based upon the pacing protocol, for example, in relation to the type of pulses which are provided by the pacemaker 60. For example, the programmer 18' can download a history of pacing that has been provided to the patient which has been sensed by the IMD 3' and derived from the sensed data, and can then adjust a monitoring protocol accordingly. The pacing module 24' also has software routines that provide the medical professional with an interactive graphical display for viewing and measuring both paced and non-paced beats and for determining how to measure ischemia in these beats. In a preferred embodiment the programmer 18' can use the pacing module 24' in order to communicate with the pacemaker 60 so that the programmer is configured to serve as a programmer for both devices, although separate programs or display screens may be required to program the IMD 3' and the pacemaker 60.

The pacing module 24' can allow the programmer to interact with the pacemaker 60, or the pacemaker's 60 programmer (not shown), in order to download information related to the pacing protocol so that monitoring can be adjusted as a function of pacing protocol. In one embodiment, the pacing module 24' is designed to automatically establish communication with the pacemaker 60 to identify the pacemaker 60 and/or its protocol and then adjust monitoring parameter values. In a second embodiment, the IMD 3' or programmer 18' has a database which contains information about third party pacing devices. This is used to provide the user of the programmer 18' with a menu for selecting the pacer model, pacing protocol, and pacing mode used by the pacemaker 60 (see FIG. 11). The values which are selected and which relate to the pacing therapy are then used to adjust the monitoring protocol. In a further embodiment, the user is provided with a look-up table (which may be stored in the pacer module 24' and which can be displayed on a programmers 18' display screen) which provides monitoring parameter values or preset protocols which are associated with different pacemakers and which can be selected or adjusted so that monitoring occurs in relation to the pacemaker 60 (and the selected protocols and modes) that is in the patient. In addition, the user programming the IMD 3' and the pacemaker 60 may involve initiating a period of override pacing where the patient's heart is paced even if not needed, so that pacing related data can be collected by the IMD 3', sent wirelessly to the physician's programmer 24 and to program the IMD 3' to be able to detect and differentiate between paced beats and non-pacedsupraventricular beats of the patient's heart.

The pacing module 28' of the EXD 20' may be provided with some or all of the features described for the pacing module 24' of the Programmer 18', but is generally more limited to features which are useful for a patient. Additionally, the modules 24', 28', and 120 (see FIG. 2) may operate jointly and are configured with routines that allow these modules to synchronize or update each other's information and parameter settings. The remote monitoring center 22', is provided with a pacing module 30' which allows remote interfacing pacing modules 24', 28', and 120' in order to communicate and set parameters as may be required by an individual patient's monitoring (or pacing) needs.

In FIG. 2, the EXD 20' with communication module 36, and one or more antennae, provides near-field and far-field wireless communication. The near-field communication may use inductively coupled wake-up type communication methods such as [??] are well known while medium and far-field communication may rely upon other means. The communication module 36 can employ standardized wireless methods such as Bluetooth, WiFi, the FCC medical band., and/or cellular communications system such as GSM, CDMA, TDMA. The communication module 36 allows for data and/or voice transmission to and from the medical monitoring center 22 via the communication link 44, and also allows communication with the IMD 3 and programmer 18. The sound module 38 has both sound input and output such as a microphone, and speaker, respectively and associated electronics for providing two-way voice communication with the remote monitoring center 22. In some embodiments the modem and communication module 36 can also communicate with the pacemaker 60. In this latter embodiment, the pacing module 28' provides the EXD 20' with the ability to serve as an external alarm and communication system for both the IMD 3' and pacemaker 60. If communication with remote monitoring center 22' occurs, the data sent over the link 44 may include, for example; (1) Description of the type of medical event that has occurred, (2) sensor data collected by the IMD 3' and or pacemaker 60 from before and after the alarm, (3) summary data processed by the IMD 3', pacemaker 60 or EXD 20', and (4) information such as parameters, protocols, and recent history categorized as a function of beat type for both paced and non paced beats recorded from a patient.

Figure 3:
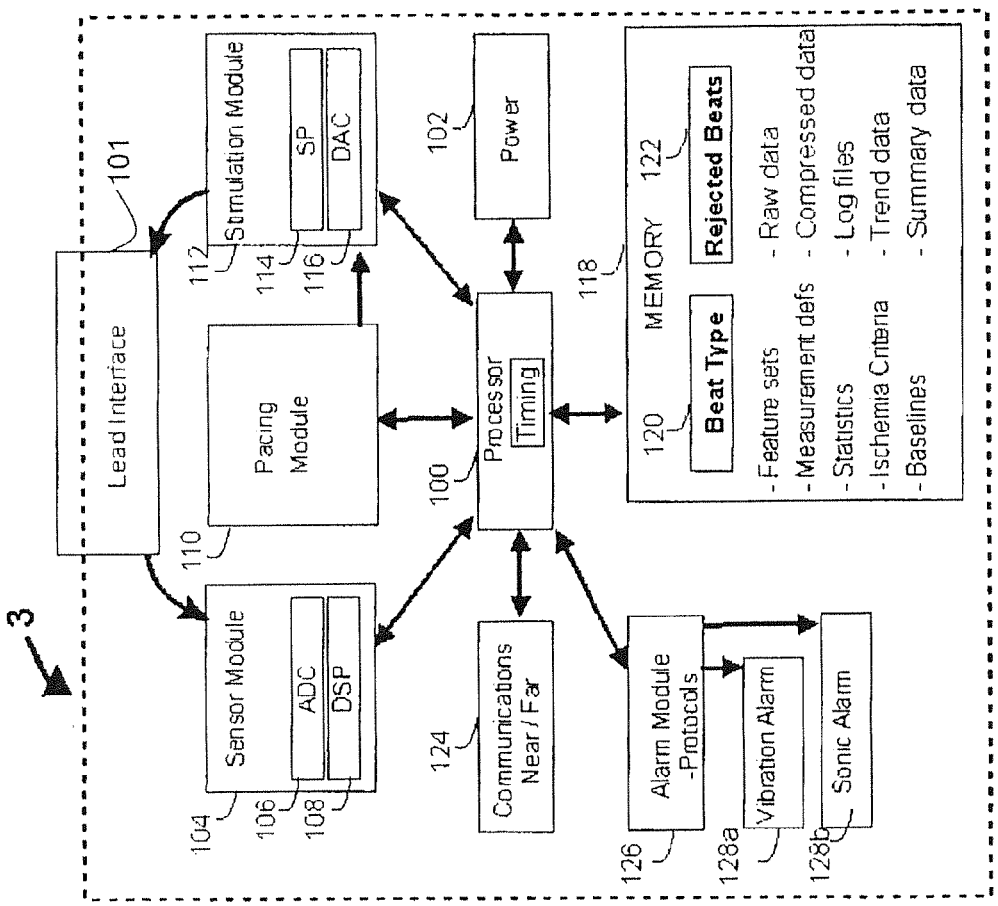
FIG. 3 shows a schematic of the functional modules of a device configured for monitoring ischemia in a patient who may sometimes receive pacing

FIG. 3 is a block diagram of an embodiment of the IMD 3 shown in FIG. 1. The IMD 3 includes a processor 100 which is powered by a power module 102, having a power supply 102 that is for example a rechargeable lithium battery. The power supply 102 may include measurement circuitry for identifying power use or predicting battery end of life, and a means for receiving inductive charging if a rechargeable battery is used. The processor 100 is functionally coupled to the other modules of the IMD 3, such that communication and power are provided and the modules operate to provide monitoring, patient alerting, and pacing therapy. The processor 100 operates a sensing subsystem which can include a sensor module 104 that received signals from the leads 1 and 2 connected to the IMD 3 through the lead interface 101. Sensed data can be amplified and conditioned by the analog-to-digital (ADC) circuitry 106 and may be further conditioned by means of optional digital-signal-processing (DSP) circuitry 108. Alternately the processor 100 may receive and process the digital signals from the ADC 106. The sensor module 104 can also provide power (if needed) to any sensor which is used by the IMD 3. The processor 100 can process the sensed data from the ADC 106 or after pre-processing by the DSP 108 to measure selected features such as the amplitude or duration of cardiac data features (e.g. R-wave height and width, average ST-segment voltage and duration). Thus the processor 100 computes the value of one or more heart signal parameters based on the measurements of these selected features of the sensed signals.

The processor 100 and/or the sensor module 104 can communicate the sensed data to the pacing module 110 which analyzes the sensed cardiac data in order to determine if pacing is required and if so, then will also determine the type of pacing. These types of pacing include any combination of fixed or variable rate pacing, single or dual chamber pacing, anti-tachycardia pacing, defibrillation and cardiac resynchronization therapy. If pacing is required then the pacing module 110 can issue a command to the stimulation module 112 to provide pacing therapy through the leads 1 or 2 connected to the lead interface 101 of the IMD 3. The stimulation signal can be created by a signal-processing (SP) circuitry 114 which may include an arbitrary function generator and can then be converted to and analog signal and amplified by the digital-to-analog (DAC) circuitry 116. The processor 100 can use the memory 118 to store, for example, raw waveforms, measured features, summary data, computed statistics, measurement definitions, ischemia criteria, and an event logs. An event log can contain characteristics of the events and times of events that are registered by the processor 100 of the IMD 3. Events may include information such as the detection of ischemic beats, communications between the IMD 3 and EXD 20, delivery of pacing, patient notification, and any other event relevant to IMD 3 operation. The memory 118 may be accessed by the processor in a manner that allows it to function as a query-capable database. The memory module 118 can contain a beat type module 120 which is the parameterized description of paced and non-paced (sinus) beats used by the processor 100 to identify beat data as coming from a paced or non-paced beat. The beat type module 120 may also allow the processor 100 to flag/classify any data which has been stored in memory as relating to paced or non-paced beat types. Further, datasets of stored sensed data for different beat types can include all data types (e.g., raw data, trend data, statistics) and can be calculated and operated upon separately by the processor module 100 under the guidance of the beat-type module 120. The reference data stored in memory 118 can include, as a function of beat type, ischemia detection thresholds related to size or duration criteria (or both), trend summaries of features, statistical calculations such as mean and variance. Alternatively, the reference data, log files, and other data stored in memory 118 may concatenate at least a portion of the data values across more than one beat type.

The rejected beats module 122 stores raw sensed/digitized data and statistics related to the description of rejected beats. Rejected beats can be classified into several categories. One type of rejected beat that the rejected beats module 122 tracks are either paced or non-paced beats which are rejected from analysis, especially if these occur while waiting for a selected type of beat which is required to measure ischemia. For example, if the ischemia monitoring protocol attempts to measure non-paced (sinus) beats in order to measure ischemia and either paced or non-sinus beats have occurred, a running count of these beats is maintained by the rejected beats module 122. The processor module 100 may perform certain operations when selected rejected beat values exceed a selected level. The rejected beats module 122 can also keep a track of fusion beats which have been rejected from analysis. Additionally, the module 122 can keep track of data that has been rejected due to noise or quality issues and can send notification if beats are rejected over an extended duration. Both the beat type and rejected modules will typically contain detection criterion associated with different types of beats. For example, PVCs may be identified by a shortened R-R interval and paced beats might be identified by an elongated QRS width associated with a QRS shape that is typical of the particular type of paced beat in question.

If the processor 100 analyzes the sensed data records stored in memory 118 and determines that a medical event has occurred which has been defined as requiring patient notification, it then operates to provide such notification and may do so in a manner defined by the alarm module 126 for the particular event. This may include operating the communication module 124 to attempt to communicate with external devices. The communication module 124 permits 2-way communication between the IMD and external devices and is configured for both near field communication (e.g. magnetic induction through the skin) and far field communication (e.g. the FCC medical band using the Zarlink chipset). In the case of an alarm that has been defined to have a vibration component, the vibration alarm module 128a having a drive circuit that powers a vibration motor (e.g. the vibrator motor used in a cell phone) to cause movement can be activated to provide a vibration signal as defined in the alarm module 126. Sonic alarms can also be provided by the sonic alarm module 128b that drives a sonic transducer such as a piezoelectric speaker to produce a signal that can be audibly heard outside the patient's chest. It is envisioned that patients would be alerted for a wide range of types of events including medically relevant events and device performance related events. Medical monitoring events trigger alarms when the processor 100 detects a medical event in the sensed data. For example, episodes of acute ischemia that may be indicative of a heart attack based upon a measurement of ST-shift which exceeds a specified threshold for a specified amount of time. For acute ischemia detection it is envisioned that the detection criteria including duration and thresholds would be different for when measured upon paced beats, non-paced beats, or a mixture of the two. Alerting for device performance can also occur for events such as low power, failure to detect beats for a specified period of time indicative of lead or internal device failure.

When the IMD 3' does not provide pacing the IMD 3' can analyze the cardiac data that is sensed by the implanted sensors 4, 5 in order to distinguish between paced beats, supraventricular beats, fusion beats, transition beats and beats rejected for their failure to meet one or more acceptance criteria. Paced beats can be identified according to features common for paced beats (e.g., a relatively longer QRS width and a known QRS shape) or can be identified when pacing pulse "artifacts" are detected in the sensed data. Left bundle branch block (LBBB) beats, as measured by an electrode in the RV apex, often appear similar to paced beats. To distinguish between the two, a paced beat template is stored. Beats that have a general paced/LBBB morphology are characterized by a longer QRS than supraventricular beats, different QRS morphology than supraventricular beats and inverted T wave. Beats with the paced/LBBB morphology are distinguished from one another by applying template matching algorithms known in the art (and examining any pacing artifact, if present).

Because pacing pulses may be much shorter (e.g. 1 ms) than the sampling resolution (5 ms at 200 Hz), the sampling rate may set at 4 kHz, in order to detect pacing pulses, and the data may then be decimated to 200 Hz prior to analysis and storage. In addition to the signal conditioning that is provided by the sensing module 104 of the sensing subsystem, times during which pacing has been provided either by the device itself, or by a pacemaker 60 which communicates these times to the IMD 3', may be logged into the IMD memory 118 so that the monitored data can be tagged accordingly. Paced beats can then be analyzed using fusion criteria in order to determine if the paced beat is also a fusion beat. When the fusion criteria are defined as data acceptance criteria then the fused beats will be rejected from further analysis and excluded from the data used for the detection of ischemia. Further, distinguishing between sinus and paced beats can be accomplished by the analysis of the cardiac data in which paced beats are defined as having features that deviate from supraventricular beats according to beat type criteria which may be based upon prior data collected for that patient. Since a pacing pulse may look different depending upon the types of pacing provided and the locations of the stimulation leads and sensing leads, prior data of a patient can be used to adjust the beat-type criteria for improved classification performance. The device may detect ischemia, or ischemic data segments in segment-based approaches, by performing calculations on the number of detected ischemic beats which occurred within selected intervals. Under some ischemia monitoring schemes, the candidate beats which are evaluated as ischemic should not be fusion beats. Further paced beats may also be excluded as candidate ischemic beats. In other words, some assessment strategies, paced or fusion beats may be counted as normal beats but not ischemic beats. For example, if under one ischemia detection algorithm, at least 25 of 40 beats must be identified as ischemic for medically relevant ischemia to be detected (i.e. over 50% of the last 40 beats must have been ischemic), and 20 beats have been detected as non-ischemic from supraventricular beats, while 20 beats were paced or were fusion, then these other beat types may be used to satisfy the requirement for 40 total beats. Accordingly, beats of a particular beat type may be excluded from some types of analysis (not allowed to count towards ischemic beat count) and may be included in others (allowed to count for non-ischemic beat count). The IMD's processor module 100 is configured to analyze the sensed data from the leads 1 and 2 in order to accomplish a number of objectives. One objective of analyzing the cardiac data is to ensure that the data is of sufficient quality that it can then be used to detect ischemia. In FIG. 4, a process 200 for detecting ischemia using both paced and non-paced beats is shown. In step 201 a segment of data is acquired and stored in memory 118 of the IMD 3 of FIG. 3. Data analysis using descriptions in the rejected beat module 122 of the memory 118 can allow the processor 100 in step 202 to accept or reject beats to be used in the subsequent analysis of ischemia. For example, beats which are too noisy, irregular, or partial beats which are the first or the last beat in a particular interval of cardiac data may be excluded from analysis, as may fusion beats. Data related to these rejected beats (e.g., for example whether these were paced or non-paced) may be stored in the rejected beats module 122 in step 204 which can then be used to adapt the description of rejected beats for future use. Data portions which occur adjacent to axis shifts, or which also have electrical or other artifact that serves to decrease the quality of the recorded sensed data, may also be rejected. One example, of a quality check is to look for the $2^{nd}$ derivative of certain frequency range, wherein if this is above a specified level, then the data will not meet an acceptance criterion. Beats which are accepted can then be categorized by the processor 100 into different beat types (e.g. paced vs non-paced/sinus beats) in step 206 using the descriptions stored in the beat type module 120 of FIG. 3. Paced beats can be detected using a number of beat type criteria such as requiring the paced beats occur at a particular heart rate (e.g. the R-R interval is within a defined range), requiring the identification of a pacing-pulse for data sensed by at least one electrode, or when the device itself provides pacing and the pacing module 110 of FIG. 3 notifies the processor 100 or stores in the memory 118 as to whether a particular beat is a paced beat. For example, the processor 100 can index times when the device has operated to provide pacing and these times can be used to appropriately "tag" the cardiac data record which is analyzed, such as by beat-type module 120. Paced beats may require further criteria are met, such as requiring that paced beat contain a particular feature (such as a relatively long QRS interval compared to non-paced beats which have been identified). Since paced beats may not occur at higher heart rates, under some pacing protocols, in one embodiment the R-R interval can be limited to a defined range so that in order for a beat, or beats of a segment, to be either simply a candidate or actually identified as a paced beat, the R-R interval must be below a selected duration.

Rather than analyzing the cardiac data itself, beat type can be derived in step 206 using other techniques which are operated upon non-cardiac data. For example, if a second implanted device is providing the pacing as in the embodiment of FIG. 2, then the wireless communication subsystem of the monitoring device can be configured for communication with this second device, and distinguishing between paced and supraventricular beats is accomplished using communication data about when pacing is provided (and capture occurred). Rather than being wireless, the data relating to when pacing occur can be obtained in other manners such as a wired connection between the first and second implanted device. Additionally, the monitoring device can use a sensor that monitors the housing of the pacing device and detect an electrical, sonic, or other data which is emitted by the pacing device when it delivers pacing. Additionally, the pacing lead of the second device can be monitored by the implanted monitoring device (using lead that contacts the pacing lead) in order to determine when pacing has occurred. As will be described in FIG. 10, if an insufficient number of beats have been accepted as determined by step 207, then more data may be acquired by returning to step 200 and extending or repeating the data acquisition. For example if in a 10 second segment there are 10 beats, the first and last may be eliminated leaving 8 beats, there might be 2 PVCs, 1 noisy beat and 1 fusion beat leaving only 4 good paced or non-paced beats. If the detection criteria requires detection of 6 out of 8 beats, an additional 4 beats may be needed so the step 207 can require the steps 201 thru 206 provide additional beats from another segment of data so that a sufficient number of beats are available for subsequent analysis by steps 208a, through 212.

In one embodiment beats are measured and evaluated for ischemia in relation to beat type. Beats are classified as either ischemic or non-ischemic in steps 208a and 208b based upon a first ischemia detection criterion that is applied to non-paced/sinus beats in step 208a and a second ischemia detection criterion that is applied to paced beats in step 208b. Applying an ischemia detection criterion to a given beat can comprise measuring a beat using a measurement protocol defined for that beat type and then comparing the measured feature to the respective ischemia criterion, which may be adjusted as a function of heart-rate for the sample of data being evaluated. Heart rate can be computed only using the data being monitored for ischemia, or may also be calculated using recent data from the pacing protocol which can relate to data from just before (e.g. the last 30 seconds) the current data were collected.

Next in step 210 of the process 200 the combination of identified ischemic paced and non-paced beats from steps 208a and 208b are analyzed to see if there are a sufficient number of ischemic beats in a preset period of time to classify the segment or segments analyzed as ischemic. For example if 6 out of 8 analyzed beats either paced or non-paced were classified as ischemic beats by steps 208a or 208b then the segment is classified as ischemic. It is also envisioned that if there can be separate detections based on paced beats or non-paced beats with the decision to classify the segment as ischemic dependent on a combined detection criteria. For example if 5 out of 7 non-paced beats are ischemic and no paced beats are ischemic, the segment might be still declared ischemic based on a non-paced alone criteria even though 6 out of 8 total beats are not ischemic. Similarly if 2 out of 4 non-paced beats and 2 out of 4 paced beats are ischemic, there might be a detection of ischemia due to seeing it in both paced types at a lower level that needed for detection for a single type or the two types together.

Alternatively, in a different embodiment after beats have been categorized as paced or non-paced and then further characterized as ischemic or not, the averageof the actual ST shift of all pertinent beats in a segment (rather than the number of detected ischemic beats which occurred within an interval of cardiac data) is used to categorize the segment of cardiac data which was collected. Additionally, characteristics such as the rate or size of changes of measured features may be used to classify the segments and detect ischemia. Segment based classification schemes in the detection of ischemia have been described in US patent application 7,558,623. As an alternative to segment based detection of medically relevant ischemic events, calculations can be performed upon detected paced and non-paced beats which occurred within an interval of cardiac data, where paced beat acceptance criteria and non-paced beat acceptance criteria can be used to determine how large a change must be in order for a beat of a particular beat type to be included in a running sum which is used to detect a medically relevant ischemic event (see, the Rate of Change Applications mentioned in the Summary of the Invention). In these cases, either individual beats or segment averages may be used to provide detection of ischemic events worthy of patient notification.

In the next step 212 a recent history of segments are evaluated in relation to ischemia event detection. An ischemic event is different than classifying beats or segments as ischemic and its detection is the trigger for specific actions such as the initiation of patient alerting or wireless data transmission to the remote monitoring center 22 of FIGS. 1 and 2. Ischemic events occur when more than a specified number of segments are classified as ischemic, for example, 3 adjacent ischemic segments may be required for detection of an ischemic event. In response to the detection of ischemia notification by step 214 of the process 200 may occur through the alarm module 126 of the IMD 3 of FIG. 3 or using the wireless communication module 124 of the IMD 3 which can be configured to communicate with an external patient device, patient programmer, or other type of external device such as a third party device which is located in a hospital. Additionally, such wireless communication as provided by modules 26, 36, 124 can provide notification of ischemia to a remote party such as the patient's doctor or the remote monitoring center 22. This may occur directly, such as the internal device communicating with a cellular or wide area network (WAN), or via the external pager type device which then relays this communication. The monitoring device can contain alerting means for providing notification when ischemic events are detected. If the patient is to be alerted then there may be transducers to allow this to occur such as vibrators or sonic transducers. Additionally, alert signals and data, or simply data, may be sent to a remote party according to a protocol when data has been identified as having ischemic beats that have the potential to be medically relevant and which should be reviewed prior to alerting the patient. There are many types of medical notification strategies. Some of these are automatic and notify the patient directly, others send data to a remote station where it is automatically or semi-automatically processed in order to determine if a patient is experiencing a medically relevant event requiring notification/intervention. All of these known methods may be used with the current invention.

Rather than combining two different beat types, the processor 100 of the IMD 3 can be further configured to classify a segment or measure ischemia by only counting ischemic beats of one beat type when a sufficient number of such paced or non-paced beats exist within a specified interval, while rejecting the others from analysis. For example, if in step 202 it is found that 8 out of 11 beats of a cardiac data sample are non-paced, then instead of attempting to incorporate the paced beat in to the analysis of ischemia, the paced beats can simply be rejected and excluded from further analysis, aside from updating the rejected beat history in step 204 with this information. In the case where there are not enough non-paced beats in a segment in step 207, rather than incorporating the paced-beat information, the processor 100 can also be configured to increase the duration of data collection by a selected amount (by returning to step 201) in order to attempt to collect more non-paced beats (also see FIG. 8). Further, this attempt may be repeated more than once. Alternatively, a minimum delay such as 90 seconds may be introduced between these subsequent attempts.

The analysis of cardiac data by the processor 100 includes measuring features of each beat type. FIGS. 5A and 5B illustrate features which may be measured for non-paced and paced beats in the first and second column, respectively, from a tip-to-can perspective. The pacing beats shown in FIGS. 5B and 5D are representative of an individual with chronic ischemia. In the case of the non-paced beat a clear QRS complex is shown, which allows measurement of the R-wave height, while in the case of a paced-beat the QRS complex demonstrates an expanded width. Although a pacing artifact may be resident at the start of the complex, this may often not be seen when sampling of the waveforms used in ischemia detection is only in the range of 200 Hz, since pacing pulse may last 1 msec or less, which is too fast to be detected consistently using that sample rate. The same features may be measured for different beat types, and this may occur using identical definitions of beginning and end latencies or identical intervals but with different start times. For example, in the case of a non-paced beat the R-wave may be measured based upon the largest slope alternation within a candidate heartbeat, while in the case of a paced beat, the "R-wave" may be identified as the largest recorded potential which occurred within a selected interval that is defined in relation to the timing of the pacing pulse. Further the PQ interval may start at the detection of a p-wave in the case of a non-paced beat, and will be defined in relation to the pacing pulse in the case of a paced-beat, although measurement of both beat types will include a PQ interval measurement. Alternatively, different features may be measured for different beat types, where the paced beat may not include the same measured features as those derived for the non-paced beats. The ST-segment which is subsequently measured for paced and non-paced types of beats can be temporally defined in relation to the two different types of R-waves which are measure, or may be defined otherwise. The features that are defined differently for each beat type include interval definitions (e.g. start times and durations) during which the defined features must occur in order to be included in the evaluation of ischemia. Accordingly, the measured features of each heartbeat can be defined differently for each beat type so that features are measured using a non-paced/sinus measuring protocol to measure non paced/sinus beats and a paced beat measuring protocol to measure paced beats. The rules used to define acceptable activity which is measured in each type of beat may also vary as a function of beat type. FIGS. 5C and 5D show a "blanking period" which is used to define a period during which a subsequent R-wave may not be measured subsequent to an R-wave which has just been detected. This period is useful, for example, in preventing algorithms from identifying waveforms incorrectly such as may occur when a T-wave is incorrectly identified as an R-wave. In the case of a paced beats the R-waves will be known, and therefore the paced beat measurement protocol may not require use of the blanking period if the next beat is a paced beat, or may use a different blanking period. These examples illustrate features of the different measurement protocols that could be used in steps 208a and 208b.

Figures 5E, 5F:
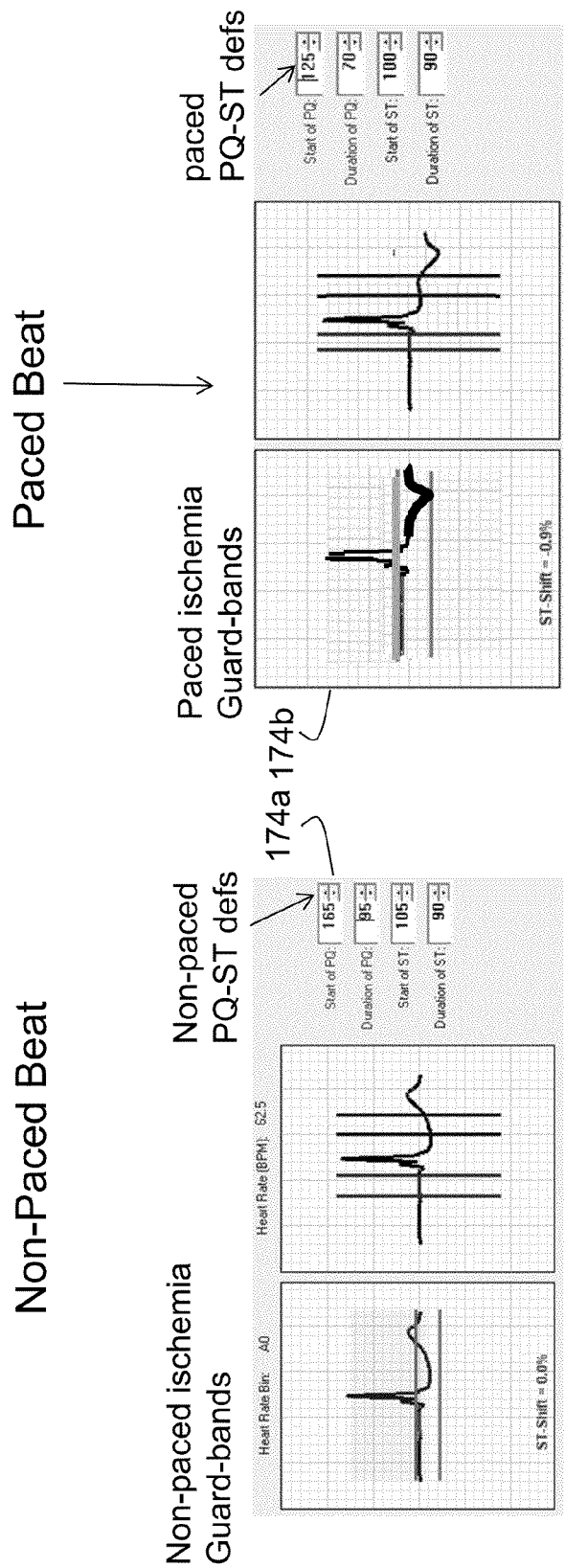
FIGS. 5E and 5F show ventricular paced and supraventricular beat types, respectively, with examples of how graphical interfaces can be used to set parameter values for measuring features and evaluating those features in relation to ischemic criteria.

In an alternative embodiment, ST deviation is measured with respect to ST and PQ points that are found based on slope criteria, as described in provisional patent application 61/152, 367, filed 2/2009, entitled "Time Series Tracking System and Methods for the Detection of Cardiac Events", filed 2/2009 and owned by the assignee hereof Once the processor 100 has measured the relevant features of each beat type and calculated the values of specific heart signal parameters for the beat type, these are operated upon to detect ischemia. One manner of processing compares the value of one or more heart signal parameters for a beat type to a first and a second ischemia detection criterion, for non-paced and paced beat types respectively. In this manner, when the two types of criteria, which may be heart-rate dependent, are applied to a measure which includes the ST-segment, as measured from either of the two types of beats, then each beat can be classified as ischemic or not. FIGS. 5E and 5F, show a graphical user interface for viewing/setting the upper and lower ischemia detection thresholds. On the left the ischemia thresholds for non-paced beats are shown as lines above and below the heart beat. Also shown are intervals in which the PQ and ST segments are allowed to be detected, with graphical controls for setting latencies relative to the identified R-wave peak of each beat. On the right side of the figure, similar information is shown as defined for the paced-beats.

The ischemia detection thresholds shown in FIGS. 5E and 5F, may be based on the difference between ST segment and PQ segment voltage defined here as "ST-deviation". Features, such as ST-deviation, may not be compared directly to a criterion, but rather to previously measured features. For example, the difference between the ST-deviations of the beats of the current set of data and an appropriate reference (e.g. a reference calculated for a particular beat type) can be evaluated. When a baseline reference value is compared to a current ST-segment value, a measure of ST shift can be calculated and the equation used to evaluate each beat may be:

$$ST\text{-Shift }\%_{type}((PQ\text{-}ST_{base})-(PQ\text{-}ST_{type})/RPQ_{type})*100$$

Where ST-Shift $\%_{type}$ is the normalized difference between the current ST-deviation and a baseline ST-deviation average value for a particular beat type. Normalization may be made using the R-wave reference height to the PQ segment from a collection of baseline beats with references set separately for paced and non-paced/sinus beat types (i.e., $RPQ_{type}$), or simply using a baseline R-wave reference value which is used for both beat types. In this latter case, a correction coefficient may be used. For example, R-wave height for non-paced beats may be multiplied against the correction factor before being used to calculate the ST-shift % for the paced-beats. This may be of use when the R-wave of the paced beats are not used, due to the pacing artifact or for other reasons. It may be preferred however to use a single value for amplitude normalization but allow different thresholds for ischemia detection for paced vs non-paced/sinus beats. It is also envisioned that any baseline signal amplitude measurement such as QRS height can be used here for normalization.

As an alternative to classifying beats as either normal or ischemic, and performing calculations on this binary set of results, one can quantitatively assess cardiac features and the changes which occur in the beats over time and in relation to reference values. Further, rates of change as a function of time may be used to derive important features in the data. In one embodiment, time rate of change measures are calculated separately for each beat type and ischemia is detected separately for each beat type in the manner described in. the Rate of Change Applications mentioned in the Summary of the Invention In one embodiment of the present invention, self-normative or "baseline" data is used by the IMD 3 as a reference to which currently sensed data is compared. FIG. 6 shows an example of the process 252 by which the IMD 3 of FIG. 1 or IMD 3' of FIG. 2 would initiate collection of such baseline data. Once the IMD 3 or 3' is implanted it would be programmed to begin acquiring cardiac data; however, obtaining reference data does not begin until a stabilization condition has been met in step 254. This is to ensure that following surgery, the characteristics of the electrode-tissue interface have stabilized and that factors such as injury current are not biasing the shape of heart-beat features. An example of such a stabilization is that of implanted electrodes, where there is a one to 7 day time period during which injury current from the implantation affects the signal typically creating a significant ST voltage offsets. It is also envisioned that the stabilization condition of step 254 could be a time delay, e.g. 7 days.

Once the stabilization condition(s) in step 254 is(are) met, the IMD 3 or 3' would begin collecting baseline data from the implanted sensors in step 256. Step 256 will also include the ability to reject beats that fit rejected beat descriptions as stored in the rejected beat module 122 of the memory 118 of FIG. 3.

In step 258 the IMD 3/3' will determine if sufficient baseline data has been collected to calculate a baseline data set in step 262 and initiate cardiac monitoring. The step 258 may include processes 259 which determines if there is a sufficient amount of paced baseline data collected, process 260 that determines if there is a sufficient amount of non-paced data collected and process 261 that determines enough time has elapsed to that the data is representative of a sufficient period of time. Once this time condition is met the step 258 could then run processes 259 and 260 to determine if sufficient numbers of paced and non-paced data has been collected and then move on from there.

Since the IMD 3/3' is designed to detect ischemia on both paced and non-paced beats, there are several ways in which the steps 256 through 264 can be implemented.

In one embodiment, both paced and non-paced beat baseline data is collected in step 256 and the IMD 3 will have sufficient baseline data collected when there are either enough paced or non-paced beats analyzed by step 258. For example, if in step 258 at a given time there are enough paced baseline beats but not enough non-paced beats, the IMD 3/3' will go to step 262 and create a baseline and detection criteria for paced beats and begin cardiac ischemia monitoring for paced beats only while an ongoing baseline creation process which is part of step 264 continues to update the paced beat baseline and tries to collect enough non-paced beats to create a non-paced baseline and detection criteria and begin ischemia monitoring on non-paced beats in step 264. This embodiment could act in a similar manner if there are enough non-paced beats but not enough paced beats in step 258 by allowing cardiac monitoring to begin after there is sufficient non-paced baseline data collected.

One modification of the above embodiment allows the IMD 3/3' in step 258 to initiate periods of pacing of the patient's heart to create a sufficiency of paced beats allowing creation of a paced beat baseline data set by step 262. These periods of pacing can be scheduled or initiated if there have been an insufficient number of paced beats over a specific time period that can be regulated by process 261, e.g. a day.

In all of the baseline data calculations the acceptance of non-paced beats may be limited to "normal beats meeting one or more criteria such as that the R-R interval for the beat lies within a specified "normal" range.

It is also envisioned that step 262 could be performed by the physician's programmer 18 of FIGS. 1 and 2 which has been sent baseline data from the IMD 3/3'. The programmer 18 may function in an automatic mode with automatic return of detection criteria back to the IMD 3/3', in a manual mode where the operator of the programmer 18 uses the programmer to calculate and or set detection criteria and then return them to the IMD 3/3' or in a semi-automated mode where the programmer calculates the detection criteria but the operator checks the result before it is downloaded back to the IMD. The manual or semi-automated modes can also be done through data communication with the remote monitoring center 22 in step 265 where a technician can either calculate and return detection criteria to the IMD 3/3' or the technician can verify and accept the calculation from step 262 and enable implementation and initiation of step 264. Step 264 also includes patient alerting appropriate to the type of ischemia detected.

The stabilization condition of step 254 can also, for example, require that the net change of a feature is above or below a selected level, a rate of change of one or more cardiac features (e.g., as evidenced by trend data) is below some level, or some feature measured in the data is present or absent (e.g., fluctuation of noise level is within a specified range defined for stability which may indicate that a subcutaneous lead has interfaced sufficiently with surrounding tissue). Additionally, when pacing is provided, stability can be defined based upon a consistency of a cardiac feature that is measured after pacing is delivered. For instance, the threshold needed to achieve pacing decreases in the initial period after implantation. Pacemakers can automatically adjust for this using auto-capture feature which adjusts applied energy as a function of physiological threshold. The auto-capture feature may be used to determine when enough time has elapsed since implantation so that baseline data collection can be initiated. Additionally, the assessment beats which are used to determine when baseline collection can be initiated may be designed so that only paced or non-paced beats are used. For example, evaluating both paced and non-paced beats, without consideration of beat type may produce sensed cardiac data which does not reliably reflect the actual injury current well. Since R-wave and ST-segments may look different for sinus and paced beats, it can be difficult to assess changes in beat features over time when more than one beat-type is considered.

The ischemia detection criterion produced by step 262 can be based upon statistical measures that are calculated for the upper and lower boundaries of the normal range of a patient based upon the baseline data. The upper and lower thresholds can be calculated independently rather than simply being a measure such as mean+/−3 standard deviations. Further, the detection criterion can be based upon non-parametric or parametric statistics computed upon the reference baseline data and may be calculated using probably distributions of this data (e.g., bootstrapped confidence limits). The detection criterion can also be set in relation to the most extreme values found in a patient during a reference period. Multiple criteria can be used that can be heart-rate dependent and specific to a particular beat type.

Several types of baseline data can be obtained. For instance, baseline data can be obtained for each of two or more beat types. FIG. 7 shows another embodiment of the present invention method in which baseline data are collected for paced and non-paced beats. In step 140 cardiac data are sensed according to an ischemia monitoring protocol. In step 142, the sensed data are processed in order to classify non-paced or paced beats. The data may be analyzed in order to determine if particular beats can be classified as either of the defined beat types and to then make their associated measurements. Alternatively, the monitoring algorithm can access the recent record of the pacing protocol in order to obtain data for identified paced beats and their measured features. The algorithm can then apply the information from the pacing monitor record onto the ischemia monitoring record. For example, times at which paces were provided, and times at which R-waves occurred for normal beats, during the pacing protocol are tagged in the data which will be then be analyzed during ischemia monitoring. In the next step the ischemia monitoring protocol then identifies any remaining beats and or features of beats which are not included in the pacing record (assuming that not all beats were paced) in order to obtain the measures needed to assess ischemic status of all beats in the current recording. This includes, for example, using times of pacing pulses to identify likely regions of R-waves for any non-paced beats (i.e. if pacing wasn't provided then the R-wave likely occurred prior to the time limit defined for the sensing parameter algorithm of the pacing protocol) and the calculation of the average heart rate of the beats assessed in the sample interval (see FIG. 10B Step 227). The ischemia monitoring and pacing protocol may operate upon the same sensed data or two datasets may be created since these two different protocols may rely upon different analysis and filtering schemes. For example, the pacing protocol may filter data between 20 and 40 Hz while the ischemia monitoring protocol may use a filter of 0.5 to 100 Hz. (See steps 227 and 236 of 10B, respectively).

After the beats are classified as paced or non-paced, the next step is to select beats that meet both "interval criteria" and "baseline criteria" 144a, 144b. Interval criteria can entail requiring sensed data in the interval to meet noise-criteria, or can require that the interval be characterized by having at least a selected number of recognized beats. Baseline criteria can require that a selected number of beats in the interval are either paced or non-paced. Another type of baseline criterion can require that the baseline data be constrained to cardiac data having beats-per-minute values which are within a specified range such as the normal resting range of an individual. This can be termed "resting heart rate range baseline data". Additionally, more than one set of baseline data can be obtained whereby baselines for different heart rate ranges are stored to serve as reference data for when currently sensed data correspond to the same range. In step 148 the non-paced baseline data are used to derive "non-paced measurement parameters" such as a reference value which contains statistical measures such as the mean and variance of ST-deviation, averaged R-wave height, or other parameters for a selected portion of baseline data which have been collected. The same is done for the paced beats 148. These statistical measures can be used to determine ischemia thresholds used during subsequent monitoring. Additionally, the baseline data can be analyzed by the IMD3 or by medically trained personnel in order to create the definitions for how beats will be measured as is shown graphically in FIGS. 5E and 5F, where a graphical user interface allows the start and duration values to be defined which will then be used to measure subsequent data. In step 150, the ischemia monitoring occurs and includes collecting, processing, and classifying incoming cardiac data according to the ischemia monitoring protocol. The incoming data can be defined within segments which can be classified in various manners (e.g., as ischemic or not) or can be evaluated in relation to individual beats, but preferentially a segment based protocol is relied upon. Step 150 can also include using sensed data to create a recent baseline dataset which may span the current data and a prior period such as a 4, 8, 12, or 24 hour period. The recent baseline data can be used to create a recent reference dataset against which new data will be compared in order to determine if there has been a medically relevant change in the ischemic status of the patient. In step 152, the results are used to detect abnormal ischemia which is medically relevant to the patient and this will lead to ischemia detection operations such as alerting the patient or sending data to a remote party.

The detection of medically relevant ischemic events may be defined differently as a function of beat types that are resident within the cardiac data that have been measured. In the case of segment-based analysis of ischemia, normally 3 segments are required to be abnormal prior to ischemia being detected. In the case of paced-beats, this number may change. In other words the criteria for detection of ischemic events that trigger alerting of a patient may change as a function of beat type. Further, if the segments contain mostly paced beats (e.g., 80%) then the criteria can be different than if few beats (e.g., 20%) are paced. In the same way, while segments of data may require 3 non-paced beats (out of 8 or so) to be elevated before the segment is classified as ischemic, a different number (e.g., 4) of paced-beats may be required in order to classify the segment in that manner. In one aspect, when beats of both types are used, these may be treated as identical and the total number of ischemic beats is simply counted across the specific interval or for a specified number of beats.

In one embodiment, reference data is collected during an initial period of about 1 week. During this time the patient may undergo a stress test in order to ensure that beats are collected over a wider range of heart rates. This reference data can be collected and can be classified into paced and non-paced interval which can then be used to set ischemia criteria. For example, the difference between the PQ segment voltages and ST-segment voltages may be used to calculate a measure termed ST-deviation for both paced and non-paced beats. ST-deviation, or additional measures, may then be evaluated to obtain statistical measures, such as the mean and standard deviation of the ST-deviation measure, which can be used to set ischemia thresholds. As cardiac monitoring progresses the newly collected baselines may be used as reference data to update the ischemia detection criteria and related statistics which are used to evaluate current cardiac data. Initial reference data which are collected are not only used to set ischemia detection thresholds, but can also be used to determine how beats of a particular beat type are measured. The detection of the start and stop latencies of a feature such as ST-segment can be accomplished either automatically, by the device, or under the guidance of a medical professional using a graphical user interface such as that shown in FIGS. 5E and 5F. Further, once measurement parameters that will be used to measure one type of beat are set, these may be used to set the measurement parameters that are used for measuring features of a different beat type. For example, the ST-segment end latency for paced beats can be set to be 10% longer than that which is set for the non-paced beats. Parameters used to measure features of paced beats may be prorated according to measures defined for non-paced beats of the patient.

Steps 140 to 148 can occur prior to the beginning of monitoring and then can occur periodically during monitoring in order to update a dataset of recent baselines to which incoming data is compared. Each of the baseline datasets can require a minimum number of recent collected beats to be present in order for to the baseline data to be used. These beats can be used to create running averages or sums, may be used to compute mean and standard deviations for various measures, or may be otherwise combined. In a preferred embodiment at least one sample (segment) of beats is collected every hour for each of 24 hours so that each baseline is calculated upon 24 datasets, or statistical summaries of these sets. Alternatively, baseline data may be collected across 6 different intervals, each spanning 4 hours, or 4 different intervals each spanning 6 hours, in each 24 hour period. It is a preference to use at least 4 sets of data in any average in order to maintain the stability of statistical measure computed upon the baseline data. When possible, the baseline data should be collected between the prior 1 hour and the prior 48 hours, in relation to the current data being assessed so that it is not too old. Data which is older than 48 hours can be considered "stale" and my not serve well as a reference to which current data should be compared because the patient's state may have changed since the baseline data were collected. Further, baseline datasets may be required to have a minimum number of beats in order to be considered reliable, such as 100 beats, and these beats may be required to be less than 4 days old.

Since the detection of ischemia is based on an analysis of a particular beat type with its respective baseline, detection can only occur if adequate baseline data exists for that type. In the case where baseline data is not available for a particular beat type then several alternatives include: alert the patient to see their doctor; increase the sampling time of data segments that are sensed; decrease the time between when data segments are sensed; reject a selected beat type such as paced or non-paced beats and then reject that beats of that type from the analysis; use an absolute or relative value criterion; use the baseline data (such as particular parameter values and threshold criteria) for a beat type that is different than the current beat being evaluated (i.e. use the baseline for non-paced beats to evaluate paced beats), and further this baseline data can be multiplied by a correction factor to be appropriately used in the evaluation of a different beat type). Additionally, in the case of paced beats, strategies can be used to obtain baseline reference data. While normal baseline data may be collected at the top of every hour, baseline data for paced beats can be collected whenever pacing occurs so that baseline collection coincides with when pacing is actually delivered. In one embodiment, the processor operates to cause sensing of cardiac data concurrent with the provision of pacing even if cardiac data are not normally scheduled to be sensed during that time. Additionally, cardiac data may be continually sensed and stored within a circular buffer until pacing takes place, at which time the buffer is allowed to fill and then is analyzed.

Alternative ischemia detection algorithms which do not rely upon a baseline reference may also be used. These may be used in addition to baseline-based ischemia detection protocols, or alternatively, when a baseline is not available or is not available for a particular beat type. As mentioned above and as will be further described below, one ischemia detection strategy is to look at the time-rate of change of at least one heart signal parameter and to detect ischemia when the cumulative change over a short period exceeds a criterion.

Rather than use of within beat-type reference data, the measured features of a particular beat type can be compared to data obtained for a different beat type. For example, a paced beat can be compared to a non-paced beat reference value. Data from paced beats which have different timings relative to the non-paced beat may be compared in the detection of ischemia. Further, paced beats may be beats that merit pacing, or upon which pacing is imposed with the intention of measuring ischemia. Further the rate of pacing may be set at a specific rate or according to a particular pattern and ischemia may be measured using a differential between the features measured in the first beat of that series to a beat which occurs later in the pacing series.

In some patients both atrial and ventricular pacing may be provided. In one embodiment the ischemia monitoring is limited to data sensed from the (right) ventricular pacing lead. Alternatively, both atrial and ventricular leads may be used for ischemia monitoring and may each have its own measurement and ischemia threshold criteria. When both leads are used then detection of ischemia may be defined as requiring a change to be seen in both leads using "and" type logic or a single lead may be sufficient when an "or" logical condition is evaluated.

Figure 8:
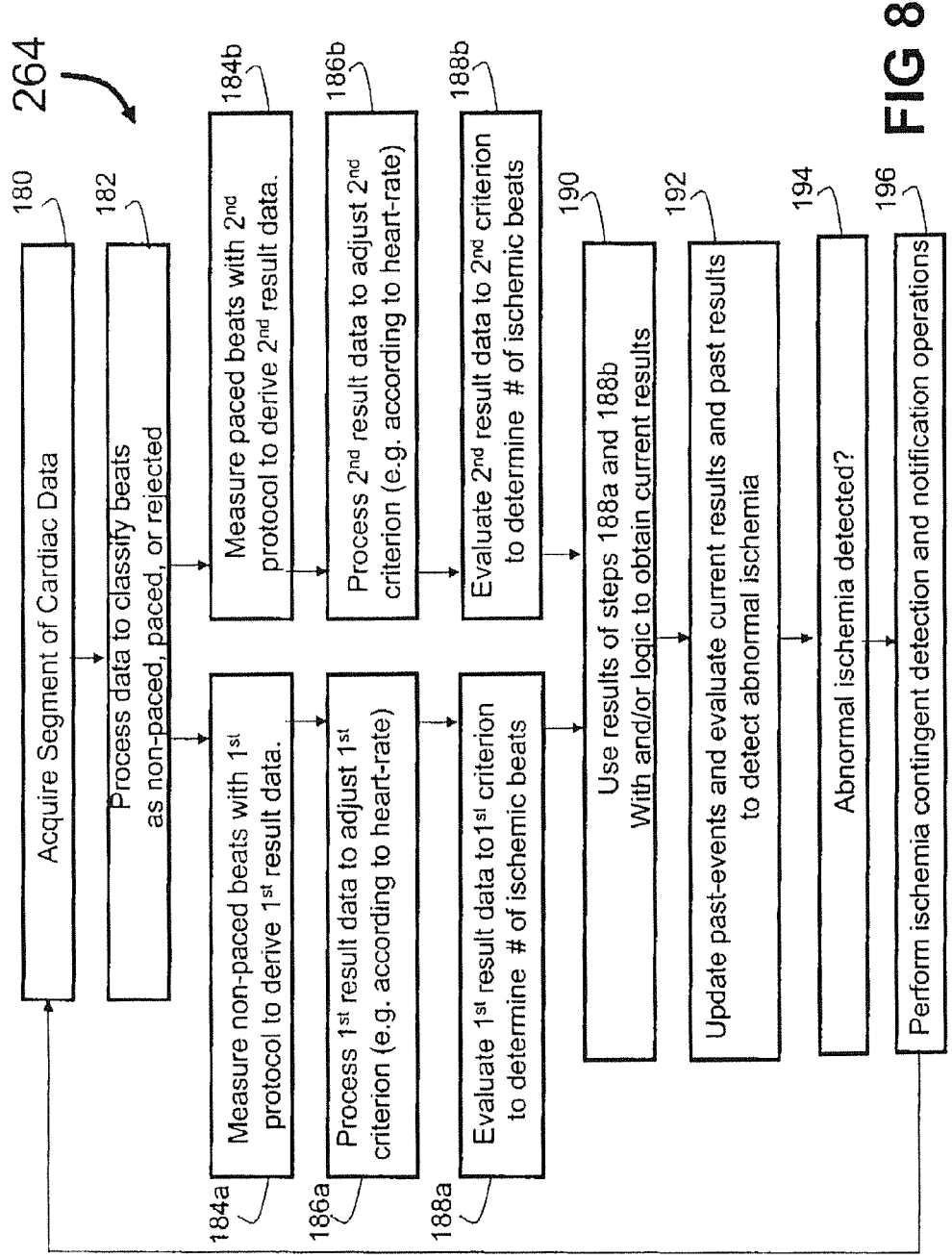
FIG. 8 shows a method for ischemia monitoring which includes monitoring paced and non-paced beats separately and combining the monitoring of the two beat types in the detection of ischemia.

FIG. 8 shows one embodiment of step 264 of FIG. 6 which is includes a method for detecting ischemia during daily life monitoring. Step 150 of FIG. 7 could be realized as steps 180 to 182 here. In steps 180 the ischemia monitoring protocol determines that the acquisition of a current data set is warranted. In step 182 the beat waveforms of the sensed cardiac data (and other data if this is also sensed by other sensors) are classified into non-paced or paced beats or are rejected. The processor 100 of FIGS. 1 and 2 is configured to assess data for each beat type only after applying data acceptance criteria to the cardiac data and rejecting data that does not meet the data acceptance criteria from being evaluated further. In the case of data that will be used for baseline data, then these criteria are called baseline data acceptance criteria. Acceptance criteria may vary as a function of beat type. For example, data acceptance criteria can also be used to ensure that fused beats are not evaluated as paced-beats by rejecting these from the analysis.

In step 184A the features of the non-paced beats are measured using a first protocol to derive a first set of result data. In step 186a, the first set of result data are used to adjust a first criterion which is used to evaluate the data. For example, the average heart rate of the first set of result data is calculated and is used to select the ischemia detection criterion that will be used to evaluate the heart beats of the first data set. In step 188a the heartbeats of the first result data are compared to a first criterion in order to determine the number of ischemic beats. This step can include computing the ST segment voltage/ST-deviation for each beat and comparing that to the ST segment voltage/ST-deviation reference computed upon the non-paced baseline data, and then comparing the calculated differences to an ischemia criterion at the appropriate heart-rate which was calculated from the variance of a reference dataset of non-paced baseline data. In steps 188b, 186b, and 188b, the method is repeated using data from paced-beats. Alternatively, based upon the ischemia monitoring protocol selected, the baseline data that is available, or the prevalence of non-paced and paced beats in the recent history of sensed data available in the reference data, only steps 184a-188a or 184b-188b can be provided. In step 190 the results of steps 188a and 188b are combined in order to obtain current results. In step 192 the recent history of past results is updated (for example, the prior "current results" are moved further down a FIFO array that may be part of the memory 118 is used to hold the result data) and then the current results and past results are evaluated in order to provide ischemia detection. For example, if the current results and the 2 most recent sets of past results are all classified as ischemic rather than normal, then a medically relevant ischemic event will be detected. In the case where ischemia is detected 194, then the defined ischemia detection and notification operations occur 196, whereas if no ischemia is detected then the method reverts back to step 180.

The IMD 3 can be set to apply separate ischemia detection criteria for the data of each beat type of paced and non-paced beats. The ischemia detection criteria that are used to detect ischemic beats may require that an ST-segment measure (e.g., ST segment voltage, ST-deviation, ST-shift, or ST-shift %) remain within a particular heart-rate related range (that can vary as a function of beat type), and may require further conditions be met such as requiring that changes (e.g. increases) in this measure occur at a particular rate, within a particular time-frame, or remain within a particular range of size. Ischemic beats can be detected using detection criteria which compare at least one heart signal parameter of current data to the patient's self-norm data and determine, for example, if this comparison exceeds a pre-set detection threshold for a particular beat type. The detection threshold may be calculated based upon either patient self-norm data, or population-matched data, with respect to a particular beat type. Relative changes (comparing features of current data to those of reference data) or absolute levels (of features in the current data) may be assessed by detection criteria, and further a combination of both these approaches may be used for either beat type.

In another aspect, an IMD 3 for monitoring ischemia and providing pacing in an ambulatory patient has a sensor implanted to sense cardiac data from a patient's heart, a stimulator configured to provide pacing, and a processor 100 which is configured both to distinguish between paced and supraventricular beats and to reject beats that do not meet acceptance criteria. The processor 100 analyzes the collected data and, in conjunction with information from the pacing protocol, detects beat samples for each beat type across a number of defined sensing periods. The processor 100 is also configured to access data from a non-electrical sensor such as an accelerometer and to use this non-cardiac data in order to adjust the analysis of cardiac data, for example, by adjusting the ischemia thresholds used to detect ischemic status of heartbeats. The processor 100 is further configured to measure heart signal features both for current sensed data and for baseline reference data and to calculate at least one statistical measure upon these heart signal features for each beat type such as mean, sum or variance. The processor 100 may thus generate at least one statistical measure for each beat type and these measures can be used either to calculate criteria for ischemia detection (in the case of baseline reference data) or can be compared against these criteria (in the case of currently sensed data). The sensing periods for baselines can be defined to occur over a prior time period, e.g. 24-hours, and may also be contingently adjusted based upon trends which occur in the historical records of sensed data. Likewise, current data may be sensed in a discontinuous manner, for example, 10 seconds of data collected every 90 seconds, may be continuous, and/or may be event driven by characteristics detected in the data monitored to provide pacing. Prior baseline reference data from the patient, including normal heart rate range baselines can be termed patient self-norm data and may be segregated and operated upon as a function of beat-type. Patient self-norm data for a heart signal parameter can be compared to current heart signal parameter data and ischemia detection can be made by comparing current and self norm data against a pre-set detection threshold. This also may be specific to a particular type of beat (e.g. sinus or paced) and which is dynamically adjusted based upon recent cardiac activity.

Figure 9A:
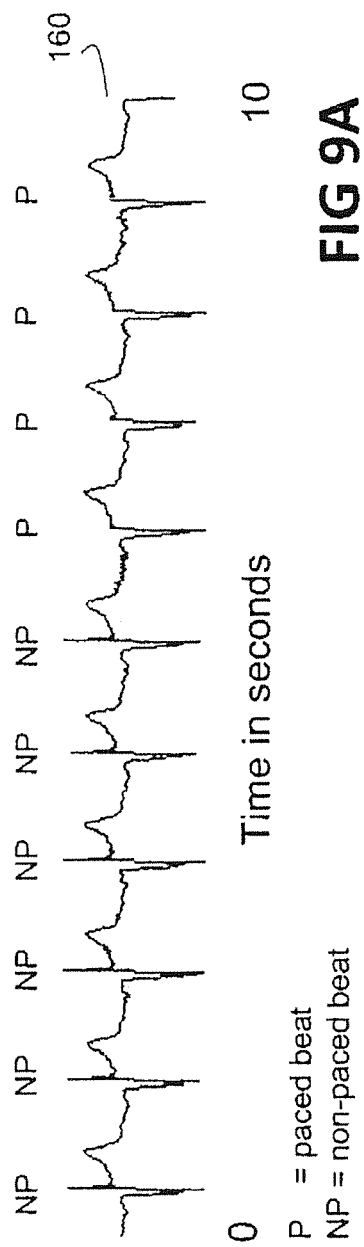
FIGS. 9A and 9B show a segment of cardiac data containing both non-paced and paced beats, respectively, and demonstrates one beat type difference that can be evident in the ST-segments of these different beat types.
Figure 9B:
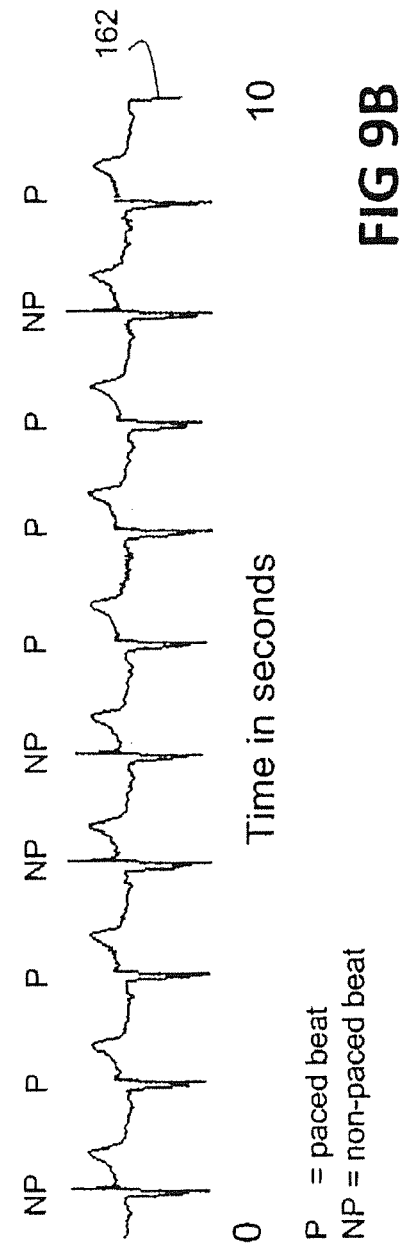
Figure 10A:
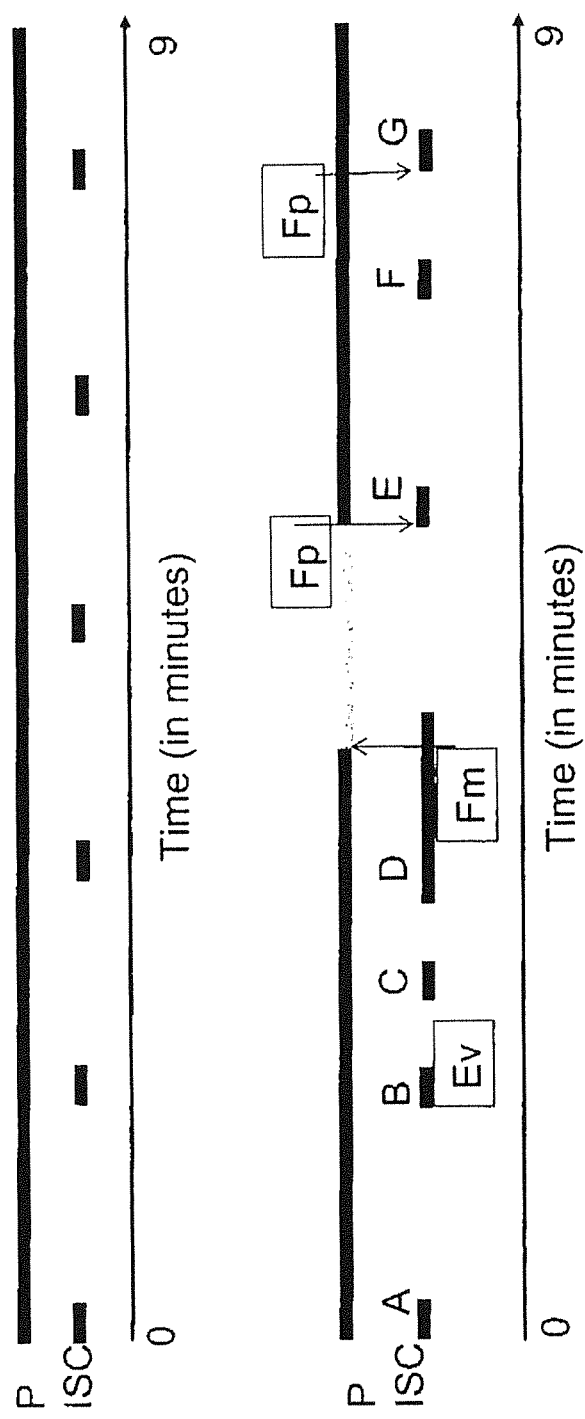
FIG. 10A shows two examples of monitoring schedules which are illustrative of both pacing protocols (P) and ischemia monitoring protocols (IS).
Figure 10B:
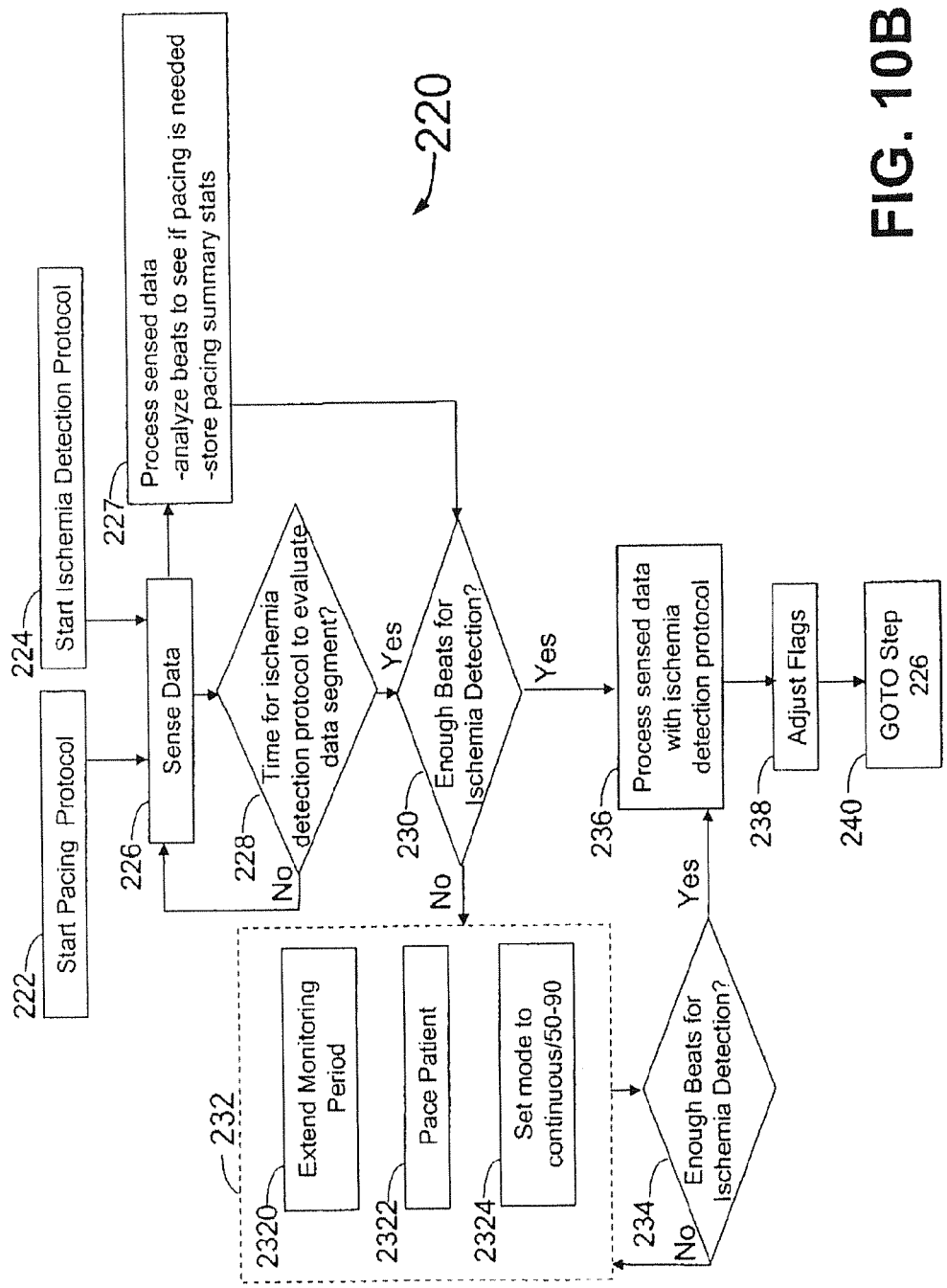
FIG. 10B shows steps of a method in which the monitoring pacing protocols (P) and ischemia monitoring protocols (IS) are modified based upon interactions between the two protocols.

FIGS. 9A and 9B show an electrogram segment of 10 seconds each. The electrogram segment 160 in FIG. 9A is characterized by 6 non-paced beats followed by 4 paced beats. The paced beats of this figure are simulated and are provided for demonstration purposes, the morphology of actual paced beats will often deviate considerably from those shown. The first and tenth beats may be immediately excluded by the ischemia monitoring algorithm since the features of these beats may not land fully within the measured segment and the first segment has no prior beat with which to reference R-R interval. The remaining beats may each be measured using non-paced and paced protocols, respectively, to obtain non-paced and paced beat features. The non-paced and paced beat features may then be compared to reference data for the two types of beats to derive quantitative results. The quantitative results for each beat type may be combined, or may be compared to ischemic thresholds for each beat type in order to obtain qualitative results such as non-ischemic or ischemic. The quantitative and/or qualitative results can then be used by an ischemia detection algorithm that evaluates individual beats or the entire segment in its detection of ischemia. In the segment 162 shown in FIG. 9B, paced beats and non-paced beats are interspersed. Under certain protocols, this distribution may cause the segment to be rejected, or certain beats may be rejected (or may cause data collection to be extended as shown in the example of FIGS. 10A and 10B). The order of beats may be used in the analysis of the cardiac data. In one example, the manner of evaluating the beat may change depending upon whether the beat is the first paced beat or a subsequent beat. Likewise, the first non-paced beat may be treated differently (e.g. rejected from analysis) than subsequent non-paced beats.

There may be morphology changes in the heart beats occurring during the transition from paced to non-paced and back. Thus one embodiment of the present invention would intentionally ignore (or otherwise treat differentially) any beat that is not preceded and followed by a beat of the same type thus negating any morphology changes in the transition from paced to non-paced beats and back. For example in FIGS. 9A and 9B, if transition beats were to be avoided then the electrogram segments 160 and 162 would have the same number of acceptable paced beats (i.e. 3) since beat 7 would be rejected from the electrogram segment 160 and beats and 1, 5 and 9 would be rejected as being transition beats.

FIG. 10A illustrates an example of how the pacing protocol (P) and ischemia monitoring protocols (ISC) can be used to contingently adjust the parameters of the other. In the top panel, the two protocols are shown over about a 9 minute period. While the pacing protocol is continuously activated, ischemia monitoring occurs discretely at 90 second intervals. When the pacing and ischemia monitoring protocols use the same sensed data, then the ISC bars simply show the data that is analyzed by the ISC protocol (e.g., a 10 seconds electrogram segments of data for every 90 seconds is analyzed). When the P and ISC monitoring protocols use different sensed data, then the ISC bars represent intervals during which data is both sensed and analyzed. This first scenario is reflective of what would normally occur during daily life monitoring when no ischemic beats are detected and when a sufficient number of beats are sampled during the sampling period. The lower panel shows a more complex scenario in which between-protocol interactions occur. At time zero, a 10 second electrogram segment is sampled (A) as defined in the default ischemia monitoring protocol. Ninety seconds later another 10 second electrogram segment is sampled and the ISC monitoring protocol detects an event (EV) in the sensed data segment (B). This causes the ISC monitoring protocol to switch from a "normal" mode to a "possible event" mode where sampling occurs more frequently (e.g., a 10 second sample is made every 30 seconds). The third sensed segment of data (C) in the ISC monitoring protocol therefore occurs 30 seconds after (B). The $4^{th}$ data segment (D) is initiated 30 seconds later. Rather than lasting 10 seconds, its duration is extended to 1 minute because the first portion of the segment (D) does not have enough beats of a particular beat type for analysis according to a segment criterion. For example, if the sensed data of the segment (D) does not contain a sufficient number of paced beats and the ischemia monitoring protocol requires ischemia detection to only occur by evaluation of paced beats, then the sampling interval can be extended from 10 seconds up to 30 seconds. After 30 seconds, a flag is set by the monitoring protocol (Fm). The flag (Fm) causes the ischemia monitoring segment to be extended and causes an adjustment in the pacing protocol (indicated by the gray shading) in which the pacing protocol paces until a sufficient number of paced beats have been obtained by the ischemia monitoring protocol (e.g. 8-10 beats). In this example segments B, C, and D were not all evaluated as ischemic and so normally this would revert to the ischemia monitoring returning to every 90 seconds instead of every 30 seconds. However, in this case the flag (Fm) not only causes the pacing protocol to provide pacing for segment D but also initiated a mode where the pacing protocol keeps track of the paced and non-paced beats over the subsequent 90 second interval. Due to the flag (Fm) the pacing protocol monitors data continuously and sets a flag (Fp) when the pacing occurs, even if the full 90 seconds hasn't elapsed. The flag (Fp) causes the ischemia monitoring protocol to sample data segment E at 70 rather than 90 seconds since pacing is occurring during this interval (or the ischemia monitoring protocol can use the interval of data which just occurred if the data was stored in a circular buffer).

The next monitoring interval "F" occurs after 90 seconds in the normal manner. The last interval is triggered 50 seconds later by another flag (Fp) which is set by the pacing protocol. In this case, the flag (Fp) was triggered because a baseline segment of data has been scheduled to occur within the next 2 minutes by the monitoring algorithm being implemented by the processor 100 of the IMD 3. The since the monitoring protocol requires that a baseline sample for the paced baseline dataset is needed within the next 2 minutes for the upcoming hour and the pacing protocol has a history of pacing that indicates pacing is occurring relatively infrequently in a selected prior time period (e.g. <20% over the last 20 minutes) and therefore issues the flag (Fp) which causes the ISC protocol to sense and analyze the baseline data segment within 2 minutes of the top of the hour since the patients need for pacing has naturally increased during this time period.

In an alternative example, the flag (Fm) may be defined to indicate that the sensed data is not of good quality due to excessive noise. This causes the pacing protocol to monitor the amount of noise in the sensed data and to set a flag (Fp) when the signal quality returns to a level where beats can again be accurately measured for ischemia detection purposes. This is of value since device resources aren't wasted by the ischemia detection algorithm's efforts towards analyzing data which is not of sufficient quality to be meaningful. In this example, the triggering of the Fp flag causes the ISC protocol to sense an additional data when the quality is again acceptable in order to provide ischemia monitoring. In the examples just provided, it is illustrated how the 2 different protocols can influence each other by setting flags in order to realize benefits such as providing more efficient and accurate evaluation of ischemia, or providing and adjusting pacing in relation to the evaluation or detection of ischemia.

In yet another alternative embodiment, flags set in the pacing protocol can be used to adjust the ischemia monitoring protocol in other manners as well. For example, a flag F1 may be set after pacing is provided for at least 50% of the time over a 1 hour period, while a different flag F2 is used if this has occurred for a 12 hour period. A flag F3 can also be set if pacing has not been provided for at least 50% of the time for at least 1 hour period, while another flag F4 is set when pacing has not been provided for at least a 12 hour period. By analyzing these sequences of flags, the ischemia monitor can adjust its function in relation to the recent history of pacing. For example, if pacing has been provided for at least a 12 hour period, and indicated by flag F2 in the pacing protocol, then the ischemia detection algorithm can adjust its function to compensate for "cardiac memory" changes that may be present in the data and this may occur until flag F4 is encountered. In an alternative embodiment, rather than using flags to indicate periods of cardiac memory, histograms, trend graphs, and summary tables can be calculated separately for paced and non-paced beats and can be operated upon to determine recent patterns in the provision of pacing. If a trend graph shows that the total number of pacing pulses has been over a threshold level within a recent period then compensate for cardiac memory, otherwise don't. This latter strategy may be easier for the IMD processor to implement since multiple flags may tend to lead to an overly state-dependent machine. Additionally, rather than flags, timers can be used when thresholds related to amount of pacing are exceeded, and the timer value can be compared to values set for various conditions to see if a particular condition is still active.

FIG. 10B diagrams an example of a process 220 for detecting of ischemia in patients with pacemakers whereby the ischemia monitoring and pacing protocols interact to adjust each other's operation. The process begins with steps 222 and 224 where the pacing protocol and ischemia detection protocol are both initiated. The process 220 first performs step 226 which consists of sensing data continuously. The sensed data may be for one or more channels and may be sensed and processed differently for the pacing and ischemia detection protocols, but in this example the same data is relied upon and any different filtering used for the two protocols is done digitally in processing that takes place in steps 228 and 230. In step 227 the sensed data is processed and analyzed to determine beats for which pacing is required. As a part of the pacing program, summary data are generated for defined intervals and this includes times at which pacing was provided, number of beats for which pacing was provided and number of non-paced beats which occurred, and an estimation of heart rate or average R-R interval across the interval. In the case where 10 second segments are used by the ischemia detection algorithm, the interval for which summary data are generated may be set to the segment length. In step 228 the processor 100 checks to see if the current time is indicated for evaluating ischemia (e.g. have 90 seconds elapsed since the last 10-second segment was evaluated?). If not enough time has elapsed then more data is sensed and if enough time has elapsed then the program moves to step 230. In step 230 the summary data from step 228 is reviewed to see if there were sufficient beats to perform ischemia detection. For example, if only paced beats are being used for ischemia detection, then the total number of paced beats can be compared to a lower limit value (e.g., 6 out of 8 beats must be paced). If there are a sufficient number of beats then the program continues to step 236, whereas if not then the program steps into subroutine 232. In step 232 at least one of several supplemental steps may occur as defined by the ischemia detection protocol in order to increase the number of beats on which ischemia may be measured. In step 2320 the monitoring period may be extended to M seconds and the additional sensed data is added to the current segment of data. In step 2322 the ischemia monitoring algorithm sets a flag (Fm) which causes the pacing algorithm to pace the patient for a specified number of beats or for a specified interval. When step 2324 is implemented then the flag (Fm) also causes the pacing protocol to change its mode. For example, the mode may be set to "continuous 50-90" whereby instead of waiting a full 90 seconds, if pacing is delivered any time between 50 and 90 seconds then the 10-second segment may be obtained at that time rather than waiting until the full 90 seconds have elapsed. Additionally rather than a continuous 10 second segment, data may be sensed continuously and non-adjacent portions of data with paced beats may be concatenated. For example, two segments of 5 seconds each or 3 segments of 4 seconds each may be "stitched together" such that a sufficient number of paced beats are obtained. In this step a parameter of the ischemia detection protocol is changed so that in step 228 the time parameter reads true at times which occur between 50 and 90 seconds after the last segment was obtained. Step 228 Obtaining the 10-second interval from a time period spanning from 50 to 90 seconds increases the chances that a sufficient number of paced beats will be obtained. In step 234 the program evaluates if enough beats have been collected for ischemia detection to occur and if so goes to step 236. If not enough beats have been collected then step 234 reverts to block 232 and steps may be repeated or contingently activated according to the ischemia detection protocol. For example, if routine 232 has not been entered recently (e.g., within the last hour) and is triggered after step 230 then step 2320 may be implemented where the monitoring period is extended, whereas if 232 is entered from step 234 then step 2322 may be triggered in which the patient is paced. In other words if there are not enough beats to measure ischemia then the segment interval is first extended M-seconds and if this still does not solve the problem then the patient is paced rather than extending the interval further. In step 238, any flags which have been set may have their status unaffected, may have their status adjusted back to a default state, or may be otherwise adjusted based upon the ischemia detection protocol. For example, if the pacing summary statistics indicate that over the last 15 minutes the occurrence of pacing has transitioned from infrequent to frequent, and in step 3234 the mode had been set to 50-90, then this flag may be set to false so that the timing of data intervals used for ischemia detection again are scheduled to occur every 90 seconds. In step 240 the process returns to step 226 where more data is sensed.

In an alternative embodiment, rather than sampling beats periodically, beats can be sensed and evaluated continuously.

As beats are sensed these are categorized and then processed in order to derive measured features for each heartbeat. The results for different beat types (e.g. paced, non-paced, ischemic-paced, irregular, etc.) are stored in buffers which are operated upon to erase the oldest data either as a function of new data entering the buffer or as a function of time. The buffers are operated upon to derive baseline reference data when needed. The buffers are also operated upon to assess whether the measured cardiac features meet ischemia detection thresholds. Ischemic events can be detected using intra-buffer or inter-buffer criteria, which assess data across different buffers.

Figure 11:
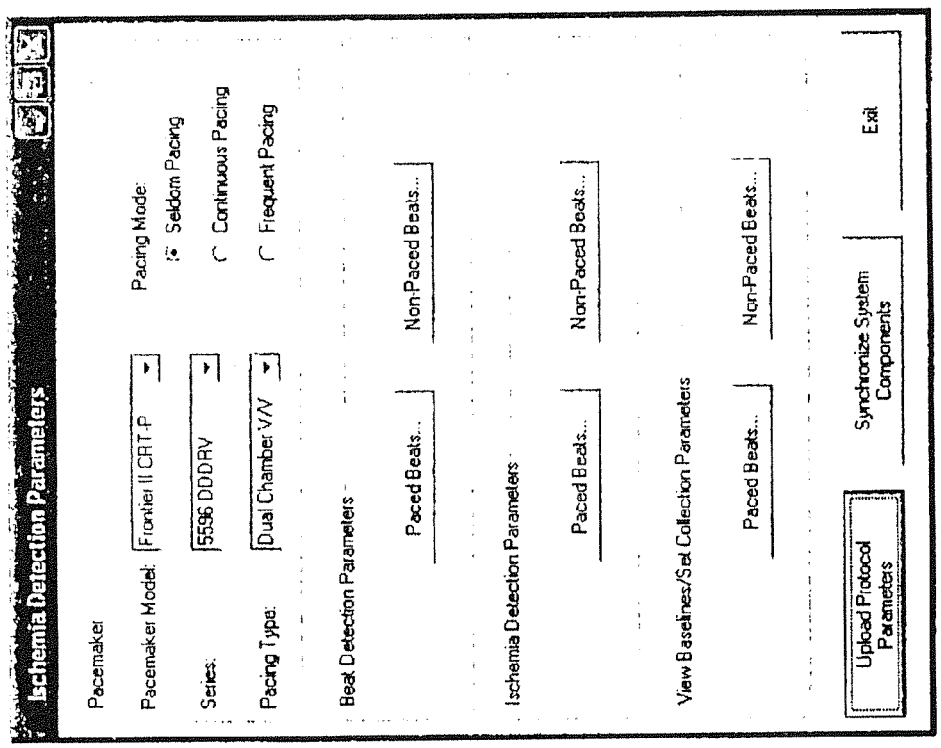
FIG. 11 shows a programming screen for adjusting beat measurement and ischemia detection characteristics used for both paced and non-paced beats.

FIG. 11 shows a display screen of the programmer 18' of FIG. 2 for the IMD 3' which is related to setting parameters used to monitor ischemia in a patient that receives pacing when the IMD itself does not provide the pacing as does the IMD 3 in FIG. 1. The screen is defined by the pacer module 24' of the programmer 18'. The screen permits the modification of various protocol parameters. The "set beat detection parameters" allows the user to configure the IMD measurement protocols used to measure features of paced and non-paced beat types (see FIG. 5A-C). The "set ischemia detection parameters" allows the user to configure the IMD ischemia detection protocols used to assess features of paced and non-paced beat types and to determine if a beat is ischemic (see FIG. 5C). The "View baselines/set collection parameters" allows the user to view baselines and summary statistics for baselines collected for each beat-type and to configure the IMD measurement protocols used to measure baseline data for paced and non-paced beat types. The "Choose Pacemaker Type" allows the user to configure the IMD ischemia measurement protocols according to the type of pacemaker, as well as the mode of pacing, that is concurrently provided in the patient. The Choose Pacemaker Model" and "Choose Series" menus comprise commercially available pacemaker models and series with which the IMD 3/3' has been designed to work. In other words, choosing a Frontier II model and selecting the 5596 DDDRV series can allow the programmer 18' to communicate with this implanted pacemaker 60, and can also be used to adjust the ischemia monitoring according to the types of pacing which are available within that particular type of pacing device. Additionally, there an "upload" button which allows the programmer to directly upload this information by communicating with an implanted Pacemaker 60 of FIG. 2, its EXD, or its programmer. The "synchronize system components" button allows the programmer to synchronize the values defined on this screen with the other system components. This can also occur automatically when exiting the screen or when terminating or establishing communication with the IMD 3'. The "Choose mode" field allows the medical practitioner to select one of 3 possible default or starting pacing modes which are oriented towards different pacing needs of individual patients Mode 1 (rare pacing), mode 2 (frequent pacing), mode 3 (both frequent and infrequent pacing).

Figure 12:
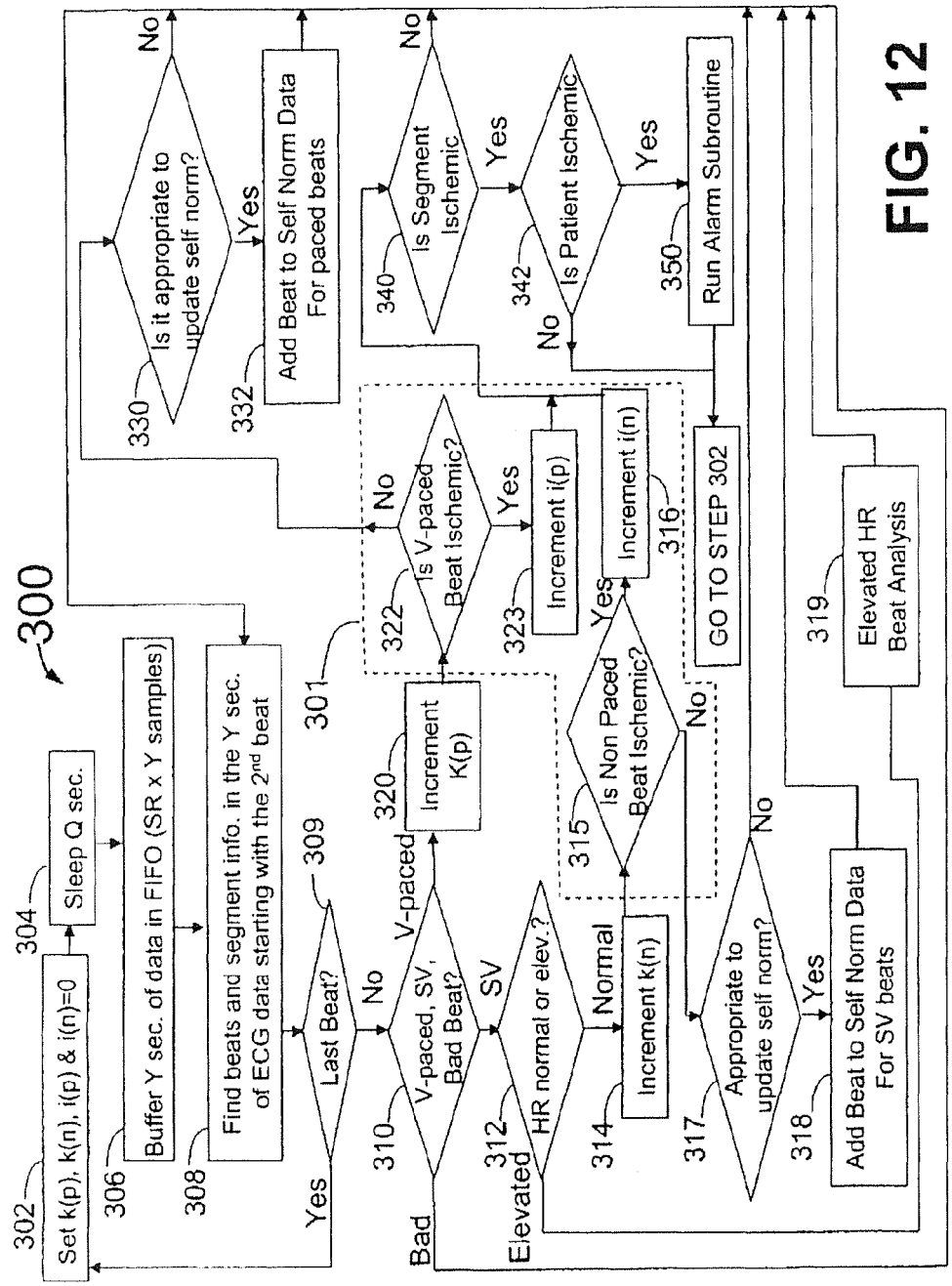
FIG. 12 shows steps of a method used to obtain self normative data for both ventricularly paced and supraventricular beats.

FIG. 12 diagrams an example of the main loop 300 of the process for detection of ischemia in patients with pacemakers. The process begins in step 302 by setting the counters k(p) (number of total ventricularly paced beats), k(n)(number of total supraventricular beats), i(p)(number of total ischemic ventricular paced beats), i(n)(number of total ischemic supraventricular beats) to zero. The loop 300 then in step 304 waits Q seconds before step 306 that collects and stores in a First-In-First-Out (FIFIO) buffer Y seconds of data at a sampling rate of SR samples-per-second for a total of SR x Y samples. Both Q and Y may be either constant values or may vary depending on other steps of the process. For example, in one embodiment the main loop 300 would sleep Q=80 seconds then collect Y=10 seconds of data if the heart signal appears to be within the definition of normal but change to X=20 seconds and Y=15 seconds if abnormalities are detected. These abnormalities include ST segment voltage changes exceeding half the detection threshold for ischemia, too many short R-R intervals indicating PVCs or other arrhythmias or an interval that reflects a transition to a period when there is little or no pacing for a substantial period of time. The FIFO buffer is typically part of the memory 118 of FIG. 3.

Step 308 follows to identify each beat starting with the $2^{nd}$ beat of the Y seconds of data and sends the digital signal samples to step 309. Step 308 also sends segment information to step 309 such as the R-R interval for the beat as measured from the prior beat and whether the beat is the last beat in the Y seconds. In step 309 if the beat is the last beat then the loop 300 will return to step 302 to begin again. The first and last beats are typically excluded from analysis because the first beat has no known R-R interval from a prior beat and the last beat may have important features such as the ST segment or T wave missing. The loop 300 continues with step 310 if the beat is any beat but the first or last beat.

Step 310 analyzes the digital samples of the beat and classifies the beat as ventricularly paced, supraventricular or bad (rejected). In this and other figures, ventricularly paced beats are abbreviated by "V-paced" and supraventricular beats are abbreviated by "SV". For ventricularly paced and supraventricular beats, step 312 checks which pacing detection mode is operative. The operative pacing detection mode is determined according to the method that will be described with reference to FIG. 15. In Mode 1, which corresponds to rare ventricular pacing, ventricularly paced beats are rejected unless choice C/block 419 in FIG. 15 is implemented. In Mode 2, which corresponds to very frequent ventricular pacing, supraventricular beats are rejected unless choice 3/block 466 in FIG. 16 is implemented. In Mode 3, neither ventricularly paced nor supraventricular beats are rejected. If in step 310 the beat is classified as "bad" or rejected, then the main loop will go back to step 308 and get the next beat.

If the beat is not paced, step 312 will then check to see if the R-R interval for the beat is appropriate to the preset normal heart rate range for the patient. If it is elevated above the normal range, then the loop 300 goes to step 319 where it performs analysis on the beat at elevated heart rate. An example of such an analysis is shown in the Hi/Low Heart Rate subroutine in FIG. 9 of U.S. Pat. No. 6,669,023 by Fischell et al. If the beat is in the normal heart rate range, the loop 300 then goes to step 314 where it increments the count of supraventricular beats k(n) and then step 315 analyzes the supraventricular beat to see if it is ischemic. An example of step 315 is included in FIG. 13 which includes the steps 315, 316, 322 and 323. If the beat is ischemic then step 316 increments the counter of ischemic supraventricular beats i(n) and proceeds to step 340 to see if the Y second long segment is classified as ischemic. FIGS. 14A and 14B show an example of the steps 340 and 342. If the beat is not ischemic the main loop 300 then proceeds to step 317 where if it is appropriate to update the self norm/baseline data for supraventricular beats. The determination in step 317 of what is appropriate may be based on time criteria, for example if it has been at least one hour since the last time 8 beats were collected for analysis in determining self norm values. If it is appropriate, in step 318 the beat is analyzed and the measured heart signal parameters are used to update the self norm/baseline data for supraventricular beats in the manner described in U.S. patent application Ser. No. 12/367,155, entitled "Baseline Processing for the Detection of Cardiac Events", filed 2/2009 and owned by the assignee hereof. If in step 317 it is not appropriate to update the self norm data or after the self norm data has been updated, the loop 300 returns to step 308 to get the next beat.

If in step 310 the beat is ventricularly paced, step 320 increments the count of ventricularly paced beats k(p) and then step 322 analyzes the beat to see if it is ischemic. If it is ischemic then step 323 increments the counter of ischemic paced beats i(p) and proceeds to step 340 to see if the Y second long segment is classified as ischemic. If the beat is not ischemic the main loop 300 then proceeds to step 330 where if it is appropriate to update the self norm/baseline data for ischemia detection. Being appropriate may involve similar or different conditions than that used in step 317 for supraventricular beats. If it is appropriate, in step 332 the beat is analyzed and the measured heart signal parameters are used to update the self norm/baseline data for ventricularly paced beats. If in step 330 it is not appropriate to update the self norm data or after the self norm data has been updated, the loop 300 returns to step 308 to get the next beat.

If in step 322 or step 315, a beat of either beat type is classified as ischemic, then step 340 will check to see if the Y second long segment can now be classified as ischemic. If it is not ischemic, then the loop 300 returns to step 308 to get the next beat. If the segment is ischemic, the main loop 300 goes to step 342 to see if the patient can be classified as ischemic. Such classification may include the cardiac features showing changes which are large enough to surpass ischemia detection criteria and can include evaluating the recent history of how segments have been classified to see if the ischemia has existed for longer than a selected duration. In the preferred embodiment, the patient is classified as ischemic if for example, three consecutive segments are classified as ischemic or 4 out of 7 consecutive segments are classified as ischemic. If in step 342 the patient is ischemic then the main loop 300 goes to run the alarm subroutine 350 which may also include the transmission of event and alarm information to external equipment and medical personnel. The alarm subroutine 350 may also include the capability to differentiate two types of ischemic conditions that occur at normal heart rates. The first of these are recovery events much like a failed stress test where the patient has an ischemic episode that follows a period of elevated heart rate. Recovery events usually indicate a stable form of ischemia that can be treated on a non-emergency basis, typically by implanting a stent at a narrowing in the patient's coronary artery. The second type of ischemic event which occurs without a prior period of elevated heart rate is much more serious and may be the indication of a heart attack. For this reason, these two types of ischemic events may trigger very different alarms. Recovery events may not even warrant an alarm, but may cause the storage of data for later physician review, initiate a minor alert to the patient to see their doctor soon, or may cause the data to be transmitted to a remote station 22. The second type of alarm however should be indicated as an emergency which alerts the patient to call 911 and get to a hospital as soon as possible because heart attacks can otherwise result in death or severe damage to the patient's heart.

Figure 13:
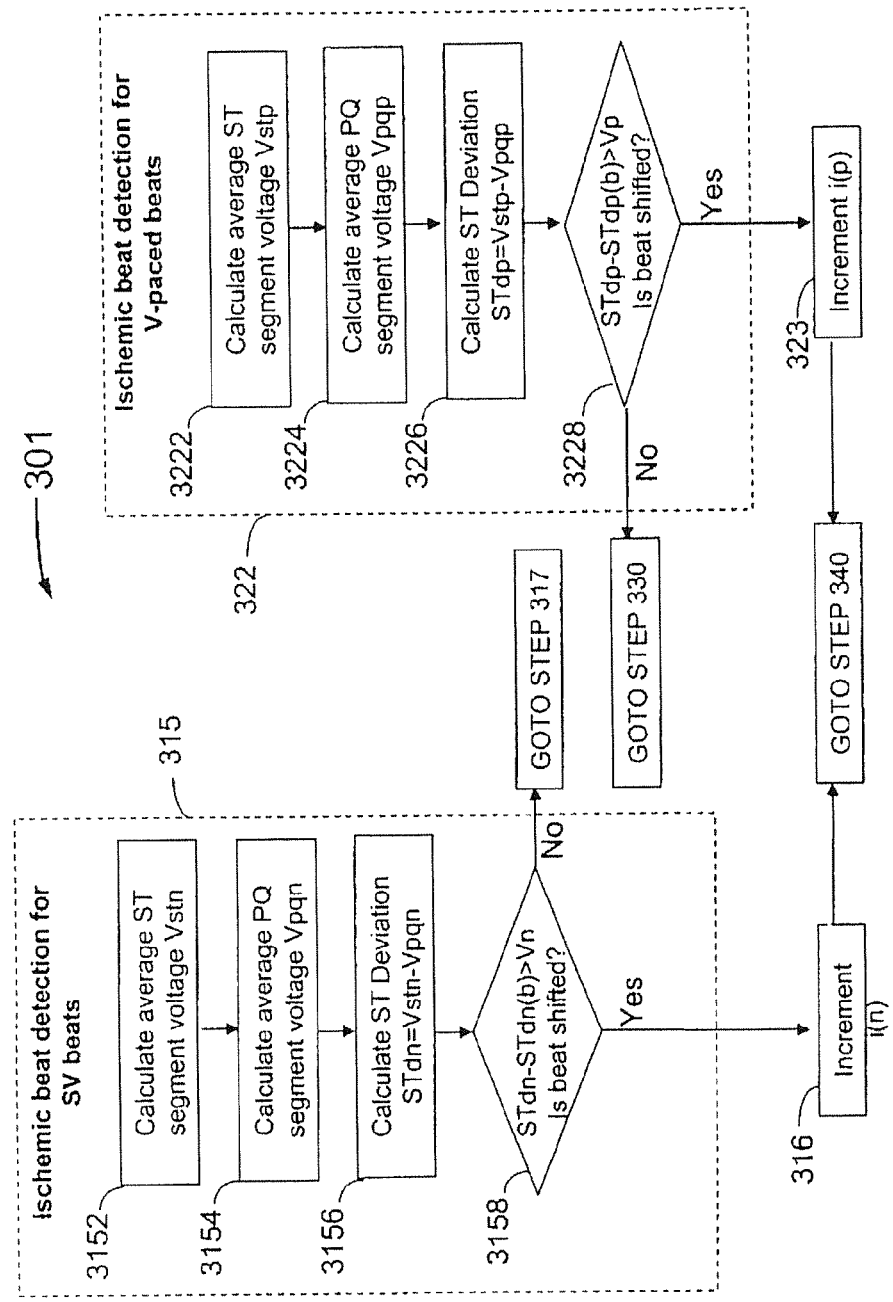
FIG. 13 shows steps of a method used to obtain self normative data for both ventricularly paced and supraventricular beats.
Figure 14A:
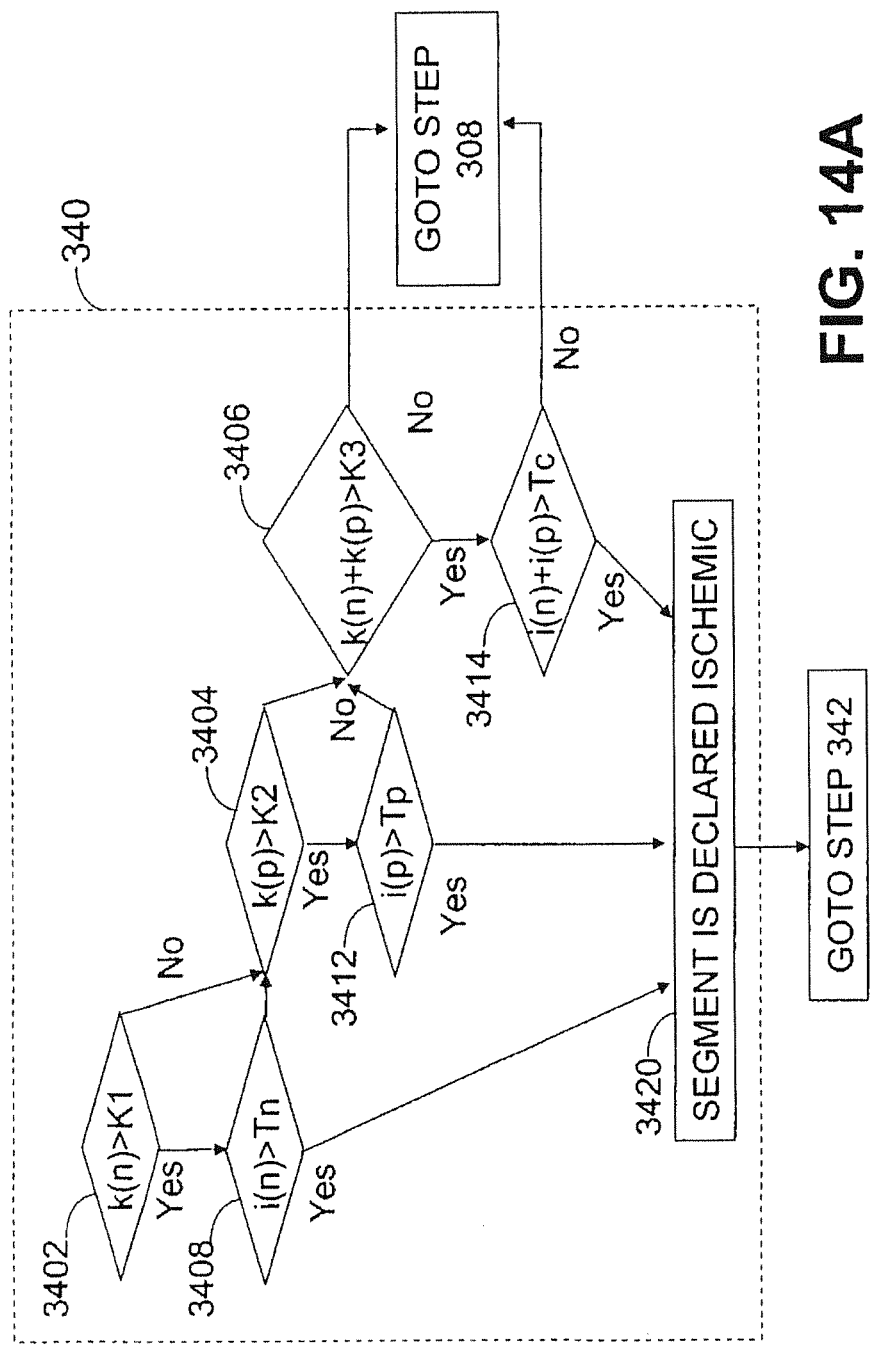
FIGS. 14a and 14b show steps of a method used to obtain self normative data for both ventricularly paced and supraventricular beats.
Figure 14B:
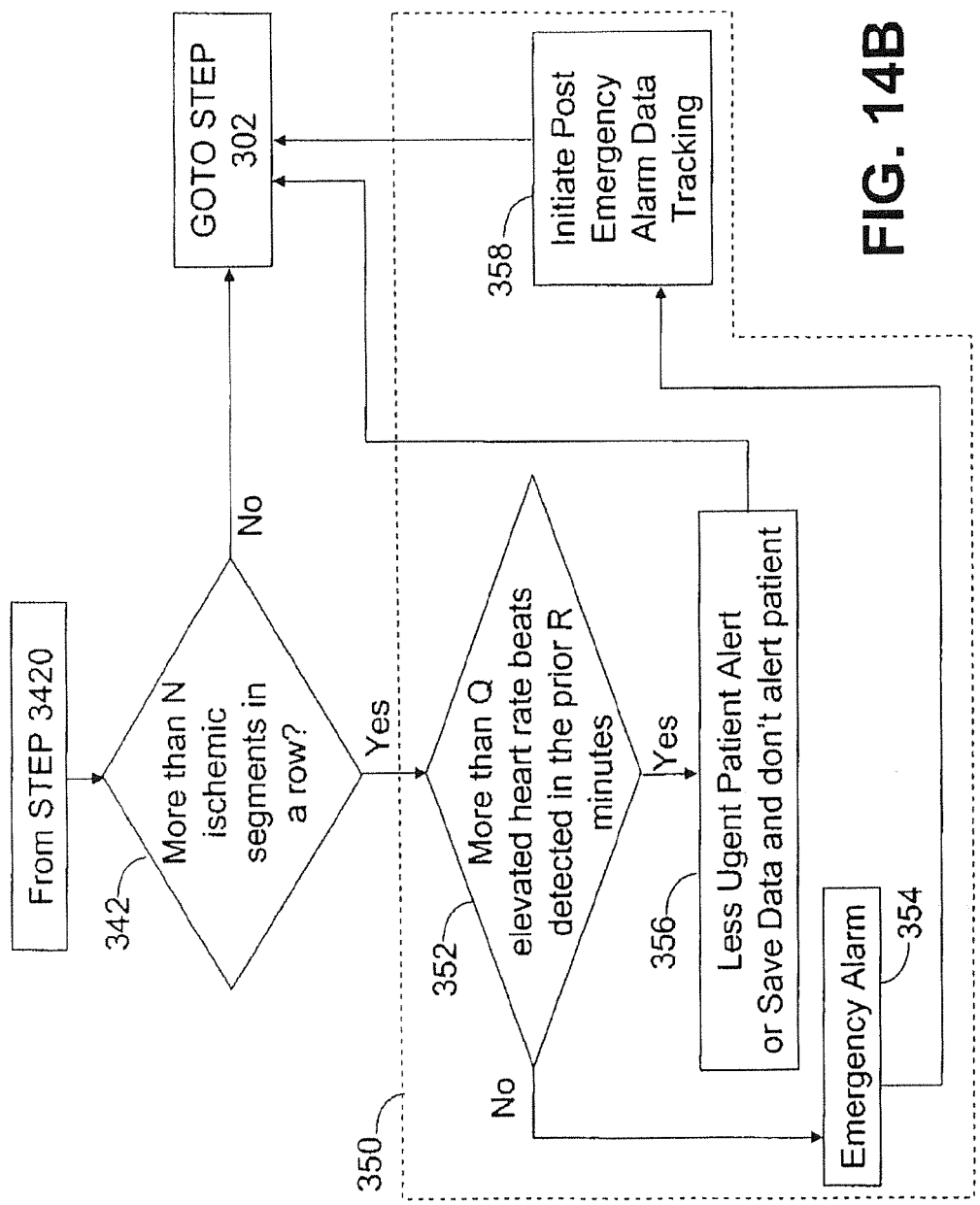

FIG. 13 shows an example of the steps involved in detecting ischemic ventricularly paced and supraventricular beats. In this example, the ST deviation which is the average ST segment voltage minus the PQ segment voltage as calculated for each of any ventricularly paced or supraventricular beats which may exist in the currently sampled data. The resulting ST deviation is then compared to a baseline value calculated from at least one prior period of the data of that patient. Specifically the step 315 is broken down into sub-steps, such as step 3152 where the average ST segment voltage for a non-paced beat "Vstn" is calculated from the digital data for that beat. Next in step 3154, the average PQ segment voltage for the supraventricular beat "Vpqn" is computed. Next step 3156 calculates the ST deviation for the supraventricular beat "STdn", which is the difference between the ST and PQ average voltages. In step 2158, the ST deviation STdn is compared to a baseline ST Deviation "STdn(b)" calculated from the average ST deviation voltages from a multiplicity of supraventricular beats over a prior time period. For example, the baseline value STdn(b) might be the average of the ST deviation of 24 sets of 8 supraventricular beats collected once per hour each hour for the prior 24 hours. A beat may be classified as ischemic in step 3158 if the beat is shifted by more than a preset ST shift threshold for supraventricular beats, "Vn". In other words, the beat is shifted if the current beat's ST deviation minus the baseline ST deviation is more than the ST shift threshold. This condition is met when STdn−STdn(b)>Vn. It is also envisioned that the threshold can be a set percentage of the baseline signal amplitude for non-paced beats A(n) which can be the height of the R wave or the peak to peak amplitude of the entire QRS complex. In this case the condition for detection of ST shift would be calculated as:

$$\frac{(STdn - STdn(b))}{A(n)} > Sn$$

Where Sn is a percentage. For example Sn might be 20% and if the ST deviation shifts more than 20% of the R height from the baseline data collected over the prior period, then the beat is classified as ischemic.

If the beat is ischemic, step 315 goes on to step 316 where it increments the ischemic supraventricular beat counter i(n) and then on to step 340 of the main loop 300 of FIG. 12. If the beat is not ischemic then step 315 goes to step 317 of the main loop 300 described in FIG. 12.

For ventricularly paced beats the step 322 is broken down into sub-steps including step 3222 where the average ST segment voltage for a ventricularly paced beat Vstp is calculated from the digital data for that beat. Next in step 3224, the average PQ segment voltage for the ventricularly paced beat Vpqp is computed. Next step 3226 calculates the ST deviation for the ventricularly paced beat, STdp which is the difference between the ST and PQ average voltages. Then in step 3228, the ST deviation STdp is compared to a baseline ST Deviation STdp(b) calculated from the average ST deviation voltages from a multiplicity of ventricularly paced beats over a prior time period. For example, the baseline value STdp(b) might be the average of the ST deviation of 24 sets of 8 ventricularly paced beats collected once per hour each hour for the prior 24 hours. To see if the beat is ischemic one checks in step 3228 if the beat is shifted by more than a preset ST shift threshold for supraventricular beats, Vp. In other words, the beat is shifted if the current beat's ST deviation minus the baseline ST deviation is more than the ST shift threshold. This condition is met when STdp−STdp(b)>Vp. It is also envisioned that the threshold can be a set percentage of the baseline signal amplitude for supraventricular beats A(p) which can be the height of the R wave or the peak to peak amplitude of the entire QRS complex. In this case the condition for detection of ST shift on paced beats would be calculated as $$\frac{(STdp - STdp(b))}{A(p)} > Sp$$

Where Sp is a percentage. For example Sn might be 20% and if the ST deviation shifts more than 20% of the R height from the baseline data collected over the prior period, then the beat is ischemic. When STdp(b) an A(p) are not available, then STdn(b) and A(n) may be used with a correction factor so that ventricularly paced beats may be compared to a supraventricular beat baseline, with correction for differences expected between the 2 beat types.

If the beat is ischemic, step 322 goes on to step 323 where it increments the ischemic ventricularly paced beat counter i(p) and then on to step 340 of the main loop 300 of FIG. 12. If the beat is not ischemic then step 322 goes to step 330 of the main loop 300 described in FIG. 12.

FIGS. 14A and 14B show an example of steps 340, 342 and 350 as follows: As shown in FIG. 14A, in step 340 sub-step 3402 first checks if there are enough supraventricular beats k(n) to perform a detection analysis with step 3408. It does this by comparing k(n) to a preset value K1. If k(n) is not greater than K1 the step 340 continues to step 3404. If k(n) is greater then K1 then sub-step 3408 is initiated to check if there have been enough ischemic beats in the segment to declare the segment of Y seconds of being ischemic. It does this by comparing the number of ventricularly ischemic beats i(n) to a preset threshold for ventricularly beats Tn. If i(n) is not greater than Tn step 340 goes on to step 3404. If i(n) is greater than Tn then the segment is declared to be ischemic by sub-step 3420.

In step 3404 the step 340 sees if there have been a sufficient number of ventricularly paced beats in the segment to declare the segment ischemic based only on ventricularly paced beats. If there are enough paced beats where k(p) is greater than the preset value K2, the step 340 continues to step 3412 to see if the segment has enough ventricularly paced beats i(p) to be declared ischemic. If i(p) is greater than the threshold for detecting ventricularly paced beats Tp then step 340 goes to step 3420 and declares the segment to be ischemic. If there are not enough ventricularly paced beats k(p) then step 340 continues on to step 3406 where it checks to see if there are enough combined number of ventricularly paced and supraventricular beats. In step 3406 if the total number of ventricularly paced and supraventricular beats combined k(n)+k(p) is greater than a preset value K3 then the step 340 goes to sub-step 3414 to check if the combination of the number of ischemic supraventricular beats i(n) and ventricularly paced beats i(p) when summed together exceed a preset threshold Tc for combined ischemic beats in a segment. If i(n)+i(p) is greater than Tc then the segment is declared ischemic by sub-step 3420. If i(n)+i(p) is not greater than Tc then step 340 returns to step 308 of the main loop to get the next beat. In step 3406 if the total number of ventricularly paced and supraventricular beats combined k(n)+k(p) is not greater than a preset value K3 then the step 340 goes back to the main loop step 308 to get the next beat.

An example of the execution of this method can require that that K1 and K2 are set to 6 beats and K3 is set at 8 beats. Tn could be 4 beats, Tp could be 5 beats and Tc could be 6 beats. Thus if 4 out of 6 supraventricular beats or 5 out of 6 ventricularly paced beats or 6 out of 8 combined ventricularly paced and supraventricular beats are ischemic then the segment would be declared ischemic in sub-step 3420.

If the segment is declared ischemic by sub-step 3420 of step 340 then, as shown in FIG. 14B, step 342 is run to check if there have been enough (e.g. N) ischemic segments in a row to declare that the patient is ischemic and alert the patient. For example N might be 3 segments in a row. Additionally, if the change in a beat feature causes a second threshold (e.g. a second Sn might be set to 50%) is large enough then N may be adaptively adjusted to 1 or 2.

If there have not been enough segments in a row in step 342 then return to step 302 and begin collecting data for the next segment, incrementing a counter to keep track of the current number of successive ischemic segments.

If there have been enough ischemic segments in a row in sub-step 342, then step 350 is initiated to alert the patient or take additional actions. The first check in step 350 is to determine if the ischemia is a recovery event by looking for periods of elevated heart rate in the prior R minutes. In sub-step 352 if there have been more than Q elevated heart rate beats detected in the prior R minutes then sub-step 352 declares that the ischemic event is a recovery type event and initiates a less urgent patient alert or just saves the data for later physician review. For example if more than Q=20 beats in the last R=5 minutes, a recovery event may be detected. In this case, after a less urgent type alert is issued or data is saved, step 350 returns to step 302 of the main loop to get another Y seconds of data. According to one embodiment, the recovery event handling in step 352 is applied only if both all of the current beats and prior high heart rate beats were associated with sinus/atrial rhythm.

Alternatively, if there has not been a prior period of elevated heart rate then the ischemic event may be a heart attack and an emergency alarm is initiated by sub-step 354 to get the patient to immediately seek medical attention. If an Emergency alarm is initiated by step-sub 354, then step 350 may initiate sub-step 358 to begin addition electrogram data storage associated with the detected emergency alarm. For example, electrogram segments of Y seconds of data from the prior 24 hours before the event and the 8 hours after the event might be stored in the memory 118 of the IMD 3' of FIG. 3 for later review. At some time after this tracking is initiated by sub-step 358, the step 350 returns to step 302 to begin collecting Y second long segments of data again. It is envisioned that this period could be the 8 hours of post event data storage. The reason for not immediately restarting detection following an emergency alarm is that there is no need to keep warning the patient and an ischemic event can last, or re-occur, for hours.

Figure 15A:
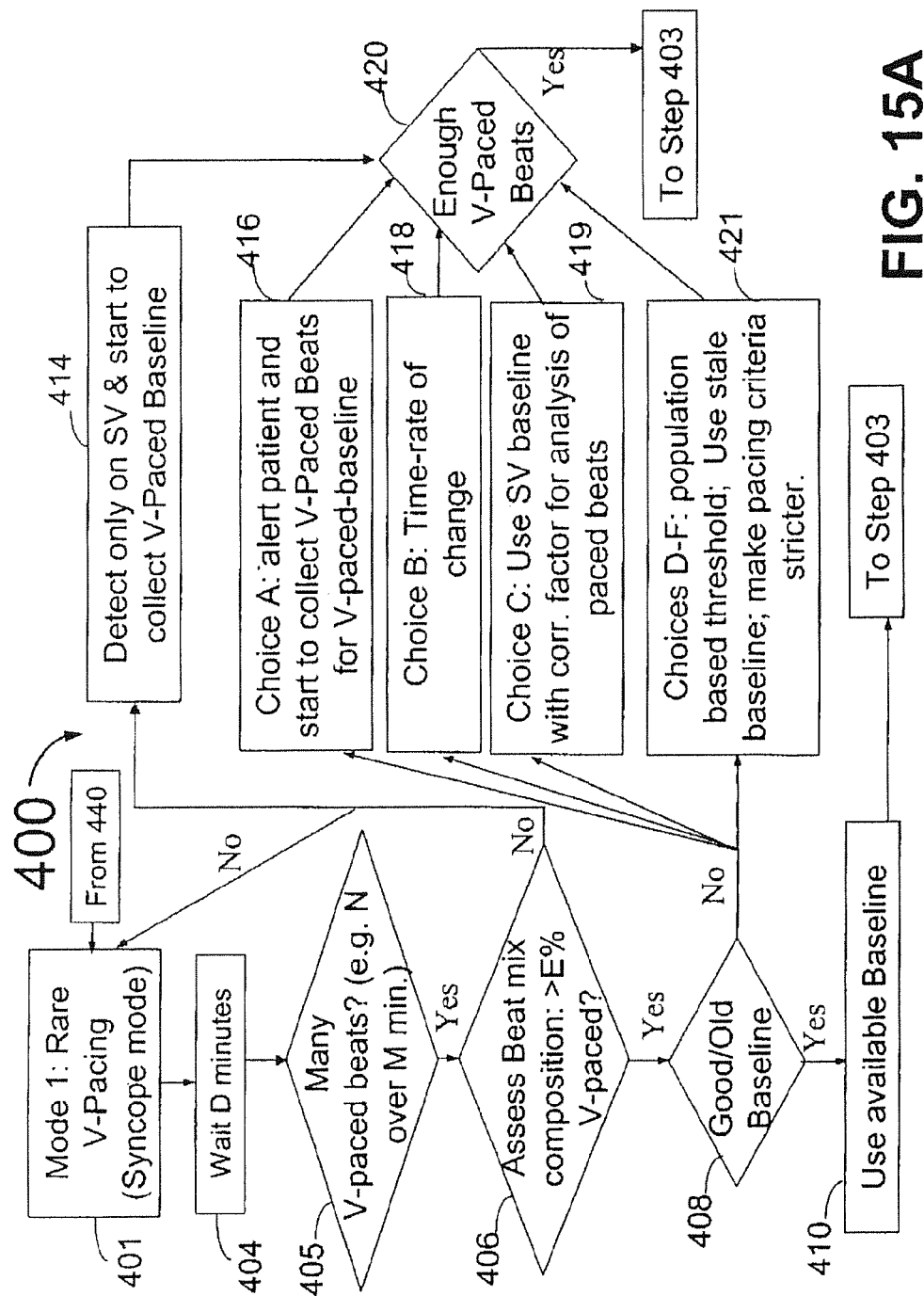
FIGS. 15a and 15b show steps of a method used to transition from Mode 1 in which ventricular pacing occurs rarely to Modes 2 or 3 when the pattern of ventricular pacing changes for a patient.
Figure 15B:
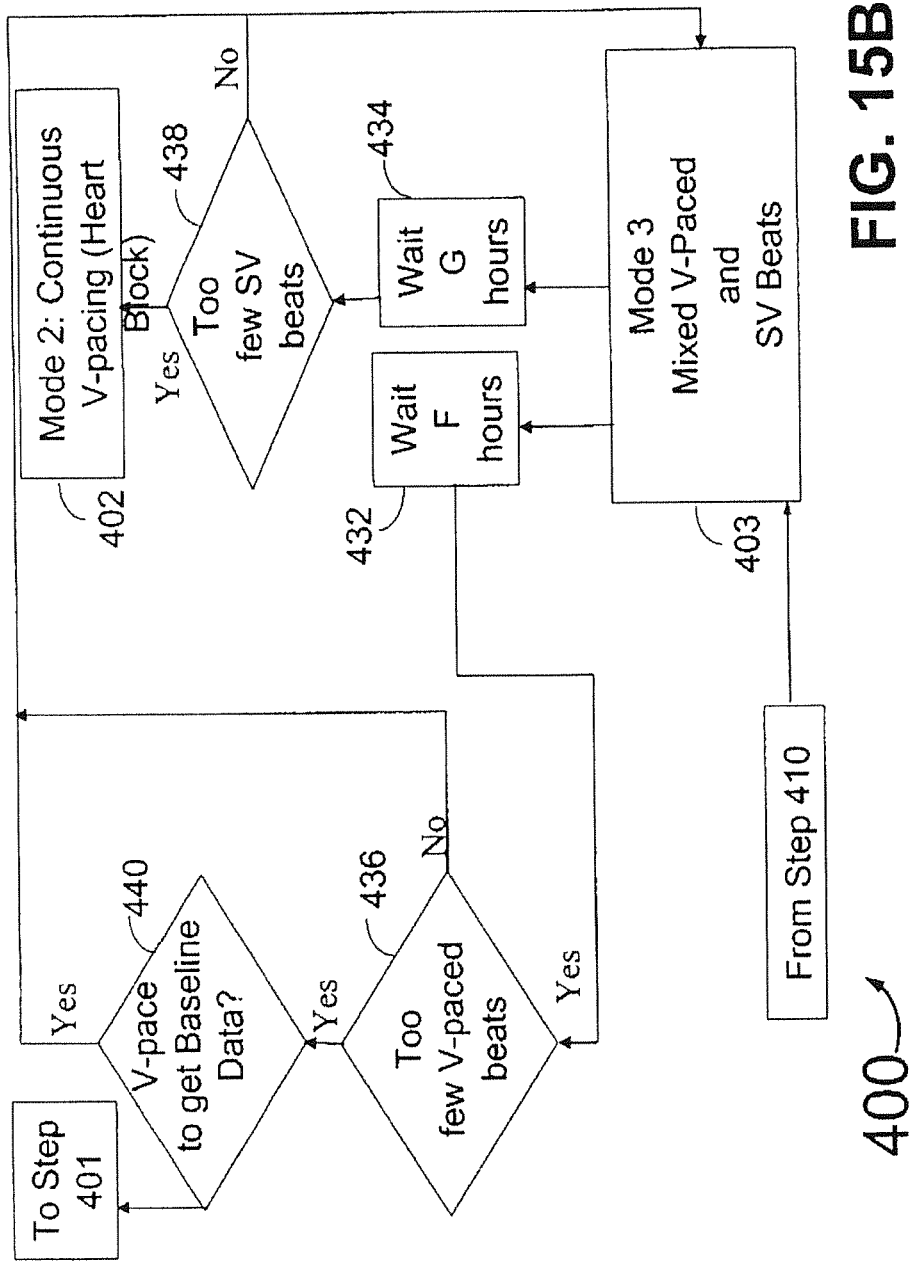

FIGS. 15A and 15B show a diagram of the process 400 used by an embodiment of the present invention. This embodiment relies on the classification of the state of pacing to be in one of three modes. Mode 1 (401) where ventricular pacing is rare, as may be the case in patients with episodes of syncope; Mode 2 (block 402 in FIG. 16) where ventricular pacing is essentially continuous, typically associated with heart block or other nerve disorders of the heart; and, Mode 3 (403) where the patient has daily episodes of both ventricular pacing and sinus/atrial rhythm without ventricular pacing. FIGS. 15A and 15B detail how the process 400 detects ischemia in the presence of each mode of pacing as well as the conditions and process by which the process 400 can change from one pacing mode to another.

In an illustrative example, patient is in Mode 1 at step 401 in FIG. 15A where the pacemaker rarely paces a ventricle and except for infrequent instances each lasting a relatively limited period. For this embodiment of the present invention, in Mode 1, ventricularly paced beats are ignored for ischemia detection. For example, in Mode 1, step 310 in FIG. 12, would not go to step 320 if a ventricularly paced beat is detected, but instead would classify the ventricularly paced beat as a bad/rejected beat (and also increment K(p)) and return to step 308 to get the next beat. It would only look for ischemia by following step 314 if the beat is a supraventricular beat identified in step 310. This would affect step 340 of FIGS. 12 and 14 as there would be no ventricularly paced beats counted and only the sub-steps 3402 and 3408 for supraventricular ischemia detection for the segment of Y seconds would operate.

Similarly if the patient is in Mode 2, then operation of step 402 (FIG. 16) would occur where the pacemaker almost always paces a ventricle. For this embodiment of the present invention, in Mode 2, supraventricular beats are ignored for ischemia detection. For example, in Mode 2, the step 310 in FIG. 12, would not go to step 312 if a supraventricular beat is detected, but instead would classify the supraventricular beat as a bad/rejected beat and return to step 308 to get the next beat (although K(n) would still be augmented). It would only assess ischemia if the beat is a ventricularly paced beat identified in step 310. This would affect step 340 of FIGS. 12 and 14 as there would be no non-paced beats counted and only the sub-steps 3404 and 3412 for ventricularly paced ischemia detection for the segment of Y seconds would operate.

Of course in Mode 3 (block 403 in FIG. 15a and FIG. 16) the full process 300 for both ventricularly paced and supraventricular beats would be operative and neither type would be classified as bad/rejected by the step 310 of FIG. 12.

FIGS. 15A and 15B provides a first example of how the IMD 3/3' of FIGS. 1 and 2 might identify changes in pacing and therefore switch between different pacing modes. The processor 100 is configured to identify pacing mode transitions based on the proportion of beats of different beat types, or a change in the proportion of beat types from a prior interval. As shown in FIG. 15A, if the patient is in Mode 1, step 401, then after a D minute delay step 404, the step 405 will check to see if there are enough ventricularly paced beats to warrant a mode change. Step 405 checks to see if there are a lot of venetricularly paced beats, e.g. more than N ventricularly paced beats over a period of M minutes, where N and M could be 50 beats over 10 minutes. If there are not enough ventricularly paced beats, the process 400 returns to Mode 1. If there are enough ventricularly paced beats in step 405, the process 400 then goes to step 406 where it is determined whether there is mostly ventricularly paced beats where for example, more than E % of the beats are ventricularly paced. E % for example, might be 90%. This would correspond to a condition where the patient's heart would go from rarely ventricularly pacing to almost continuously ventricularly pacing. If the answer to step 406 is no and there are still a fair number of supraventricular beats, then the process 400 sits in step 414 where it detects ischemia only on supraventricular beats, but will begin collecting ventricularly paced beats to create a ventricularly paced beat baseline so long as the supraventricular beats are looking "normal".

Regarding baseline acquisition, in the aforementioned application entitled "Baseline Processing for the Detection of Cardiac Events", a candidate baseline segment does not qualify as a valid baseline if its average ST segment deviation is too far shifted from the then applicable baseline, which is an average of preceding qualifying baseline segments. Obviously, such a scheme requires a start-up period. In the context of the present invention, startup periods may be required after a switch from long term pacing of one type, in which case there may not be any valid baselines with which to compare a current segment.

In this case, to define an initial baseline, the system may collect W segments over a P hour period (during which normal baseline acquisition will not be attempted) with W and P preferably set to 40 and 4, respectively. The applicable baseline may be set as an average of the ST deviation of these W segments, after eliminating outliers. Normal baseline acquisition may then be performed, using the above mentioned applicable baseline. Initially, candidate baseline segments will be compared against this applicable baseline to determine if they qualify as valid baselines. The new applicable baseline will then be updated as a weighted average of the then applicable baseline and the new valid current baseline segment. The applicable baseline will be updated with subsequent valid baselines. Alternatively, a prior "stale" baseline value may be used, or a best guess baseline may be set by the system (e.g. it may select a baseline that is related to another beat type), and the ischemia detection threshold may be increased to avoid any lack of specificity caused by using a sub-optimized baseline reference value.

After enough ventricularly paced beat baseline data is collected in step 420 that follows step 414, the process will go to step 403 entering Mode 3 where both ventricularly paced and supraventricular beats are checked for ischemia (if step 420 is no then the process reverts to step 414). Alternatively, if the answer is yes to step 406 then there may not be enough supraventricular beats present to detect an ischemic event. If this is so, step 408 will check to see if there is baseline data for paced beats that is not too old (i.e. "stale") and is sufficient for detecting ischemia in paced beats. If the old baseline is not stale then step 410 will cause the baseline for paced beats to become the current baseline and the process 400 will then move to step 403 Mode 3 in FIG. 15B.

In an alternate embodiment, the good baseline determination also depends on cardiac memory. Cardiac memory refers to the tendency of cardiac tissue to alter its electrical characteristics over time in response to a change in a pacing regime. The pacing regime change generally affects the T wave and the QT interval, but these sorts of repolarization changes may also impact the measurement of ST segment deviation. Cardiac memory will be discussed further with respect to the flow chart shown in FIG. 17.

If there is not baseline data from a sufficiently recent period then there are three different embodiments (Choices A, B and C) of the present invention which may be operated. In Choice A, step 416 would alert the patient that pacing needs have changed radically in their heart which is true if the patient has gone from rare ventricularly pacing to continuous ventricular pacing. This change in the patient's condition may be treated as less urgent alert than an ischemic event but still merits an alert for the patient to see their doctor, for example, to determine if perhaps a change in medication is warranted. In this case, step 420 would then begin collecting ventricularly paced beats to create a baseline for ischemia detection. Once enough ventricularly paced beats are collected, the method 400 then proceeds to step 403 Mode 3.

In Choice B, if non-stale baseline data does not exist as determined in step 408 then in step 418 a different ischemia detection method is selected. In this example, ischemia detection can occur by examining the time rate of change of either ST segment voltage or ST deviation where there is no longer a baseline term incorporated into the ischemia evaluation formula. For example if over a 3 minute moving-window period there is a ST-shift of more than 20% of the current R-wave height that has occurred consistently over a number segments (e.g. as described with reference to blocks 1004, 1006 and 1008 of FIG. 17) and this feature remains shifted for an additional 2 minutes, then ischemia could be detected and the process will jump to step 350 where an alarm is provided. Even while running such a time rate of change algorithm, ventricularly paced beats might be collected for a standard baseline where in step 420 after enough are collected, the system can go to step 403 Mode 3 (otherwise it reverts step 406). Even in this instance, in step 420, the detection of ischemia from supraventricular beats is ongoing if possible.

In Choice C, the existing baseline data for supraventricular beats with a correction or offset is used to provide a temporary baseline that can be used for ventricularly paced beat ischemia detection. For example, the ventricularly paced beat baseline might be some percentage of the supraventricular baseline data for ST deviation and R-wave height or there might be an offset. There are other choices which may occur and these may be available in addition to choices A-C or A-C may be substituted with these. For example, Choice D can include reverting to use of a population based threshold which does not require comparison of the ST-deviation to a self-normative baseline value. Choice E can include using a baseline which is stale as long as certain criteria are met (e.g. the baseline for the subject has been very stable and, for example, has only deviated within +/−1% for the last 4 days) suggesting that this information is still adequate for a comparison. Choice F, could include making the pacing criteria stricter (e.g. pace only if absolutely necessary) in an attempt to obtain more supraventricular beats.

In Mode 3 403 in FIG. 15B, the process 400 is checking both ventricularly paced and supraventricular beats for ischemia using the entire process 300 of FIGS. 12, 13 and 14. The present invention envisions that in Mode 3 if after a time period of F hours in step 432, there are almost no ventricularly paced beats seen by step 436 then the process goes to step 440 where it can do one of 2 things as programmed. If pacing is enabled in step 440 then the IMD 3 (and 3' if provided with this ability) will initiate a period where the patient's heart is ventricularly paced so that ventricularly paced baseline data can be collected. The process 400 would then return to Mode 3, 403 where it should now have sufficient baseline information for both ventricularly paced and supraventricular beats. If automated ventricular pacing is not enabled and there are too few ventricularly paced beats seen in step 436 then the process 400 would return to Mode 1, 401 (FIG. 15A) where ventricularly paced beats are ignored for ischemia detection.

Similarly if after a period of G hours in step 434 there are almost no supraventricular beats seen by step 438, the process 400 can go to step 402 Mode 2 operation where supraventricular beats are ignored for ischemia detection.

In both steps 436 and 438 if the answer is no, then the process 400 returns back to Mode 3, 403 where both ventricularly paced and supraventricular beats are examined for ischemia.

FIG. 16 continues the flow chart for the process 400 showing how the process 400 moves out of Mode 2 with nearly continuous ventricular pacing into Mode 3. The process 400, as shown, cannot go from either Mode 1 to Mode 2 or Mode 2 to Mode 1 without first passing through Mode 3. While a direct transition from Model to Mode 2 is obviously possible, skipping Mode 3 could cause periods where ischemia cannot be measured accurately if there is not a good ventricular paced baseline. FIG. 15 already shows how the process 400 transitions from Mode 1 to Mode 3, and how Mode 3 goes back to Modes 1 and 2. In FIG. 16, if the patient is being ventricularly paced continuously as in the case of heart block, it is conceived that the heart could at some point begin pacing on its own where there would be a large number of supraventricular beats.

While in Mode 2, 402 the process 400 would go to step 452 and wait D' minutes and then check to see if there have been a large number of supraventricular beats in step 454. For example step 454 might look to see if there have been N' supraventricular beats in M' minutes where N' and M' could be 50 beats over 10 minutes. If the condition of step 454 is not met, the process 400 returns to step 402 then 452 to wait another D' minutes where D' for example could be 5 minutes. Step 402 is active while block 452 is in effect so that ventricular pacing is not stopped while waiting time D'. If the condition of step 454 is met and there are a sufficient number of supraventricular beats the step 456 checks to see if there are mostly supraventricular beats with more than E'% of the beats in the last M' minutes being supraventricular where for example E' might be 90%. If there are less than this number of supraventricular beats but still enough to have met the condition of step 454 then the process 400 will detect ischemia only on ventricularly paced beats until it has enough time and supraventricular beats to develop a supraventricular beat baseline in step 457. Methods for establishing baselines were described with respect to to step 414 of FIG. 15). Once a baseline has been established, the process 400 will go to step 403 which is Mode 3 where detection of ischemia looks at both paced and non-paced beats as shown in the example of FIGS. 12 through 14b.

If the condition of step 456 is yes in step 458 checks to see if there is older baseline data for supraventricular beats that is still usable/good. Again, in an alternate embodiment, cardiac memory also plays a role in the baseline validity determination. If so that baseline is then enabled for ischemia detection in step 460 and the process 400 goes to step 403 for Mode 3 detection. If there is not a usable baseline for supraventricular beats, step 458 then moves to one of 3 embodiments or choices 462, 464 and 466. These choices are:

Choice 1, 462—pace the heart periodically and use this ventriculary paced data for ischemia detection, ignoring supraventricular beats for detection, but collecting supraventricular beat data until the condition of step 480 where there is enough supraventricular beats to form a usable baseline for step 403 Mode 3 detection. In one embodiment ventricular pacing occurs periodically every time a current segment is sensed, in other words 10 seconds out of every 90 is ventricularly paced. In another embodiment, ventricular pacing is applied for between 10 to 55 minutes and then supraventricular beats are allowed to occur during the other periods so that supraventricular baselines and sample "current" data sets are obtained. In a further embodiment, a smaller sample, such as a single beat is paced, and this is evaluated to see if additional beats should be ventricularly paced. For example, if the ST-segment of the ventricularly paced beat is above a particular level suggesting that ischemia may be present then additional paced beats are collected. The preferred embodiment may be any of these variations depending upon the condition of the patient, but normally the second option would be used, with 10 minutes of imposed-ventricular pacing followed by 10 minutes of non-imposed pacing.

Choice 2, 464—while collecting supraventricular beat data to form a usable baseline determined by step 480, monitor supraventricular beats for ischemia using a different algorithm for example, look at the time rate of change of ST segment deviation analogous to the manner described with reference to step 418 of FIG. 15.

Choice 3, 466—there may be strong similarities to the changes in both ventricularly paced and supraventricular beats due to ischemic conditions that would allow the ventricular paced baseline to be used to calculate an approximate supraventricular baseline for ischemia detection. For example, the threshold for detection of an ischemic ventricularly paced beat might be 25% of the baseline R height, and 25% for ischemic supraventricular beats. The average ST shift over the last hour for paced beat ST deviation as compared to the paced baseline ST deviation might be 10% of the baseline R height. One could then assume that for supraventricular beats the current average ST shift is also 10% and therefore calculate what the supraventricular baseline ST deviation would be based on ventricularly paced beat data and current measures of ST deviation for supraventricular beats. This technique could be used while continuing to collect supraventricular beats to create a usable baseline. Once step 380 determines that such a usable baseline exists, the process 400 goes to step 403 for Mode 3 operation. Alternatively, if for example, the threshold for detection of an ischemic ventricularly paced beat might be 35% of the baseline R height, and 25% for ischemic supraventricular beats, then a correction factor can be used which adjusts either the threshold or the feature being compared to the threshold.

Each of these 3 choices could work to allow the process 400 to still protect the patient by detecting significant electrogram changes indicative of heart attack even though there is not a usable baseline for supraventricular beats. When a usable baseline occurs then Mode 3 can be entered and from Mode 3 the process 400 may revert to either Mode 1 or Mode 2, according to the composition of ventricularly paced and supraventricular beats which are then subsequently acquired.

Figure 17:
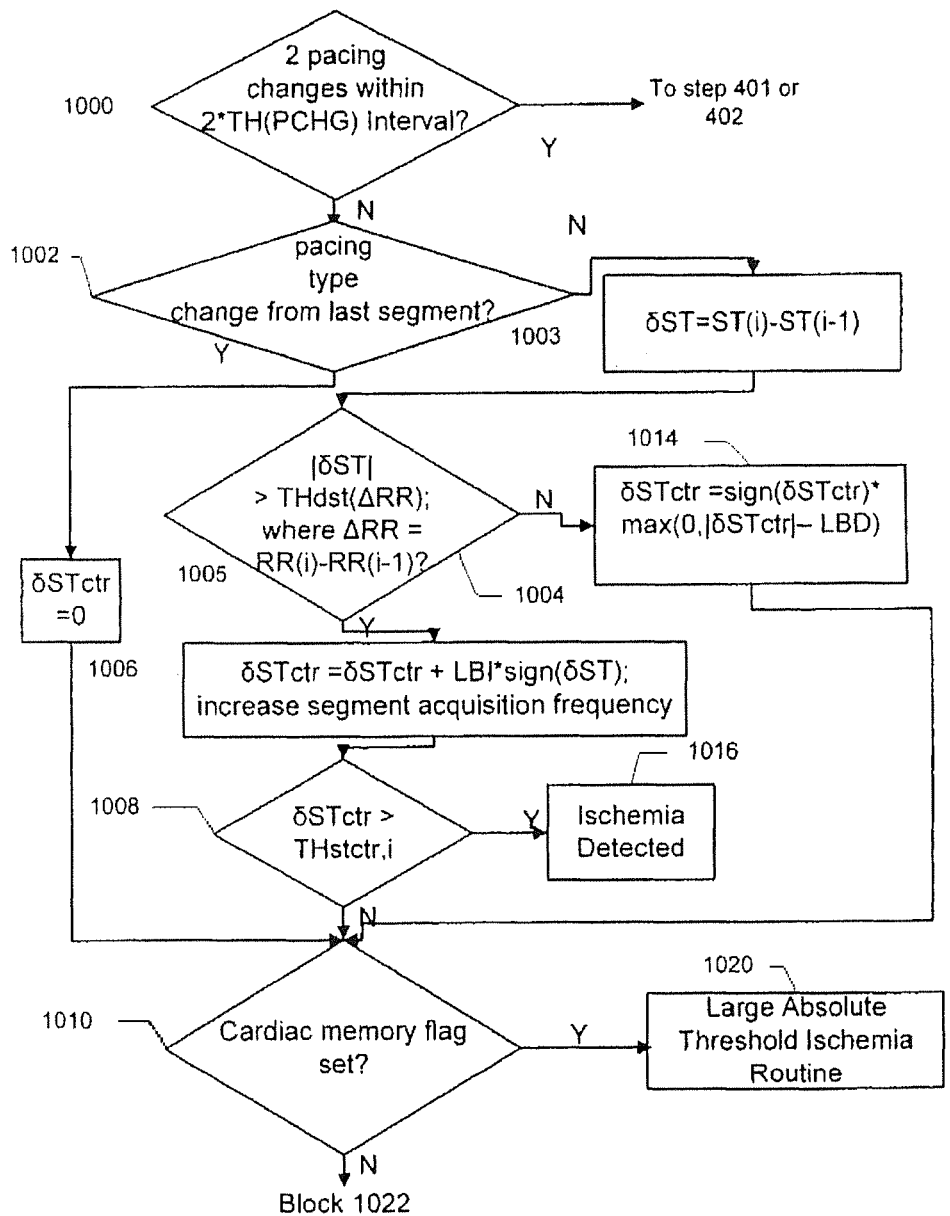
FIG. 17 shows steps of a method used to transition between different types of beats during measurement of ischemia.
Figure 18:
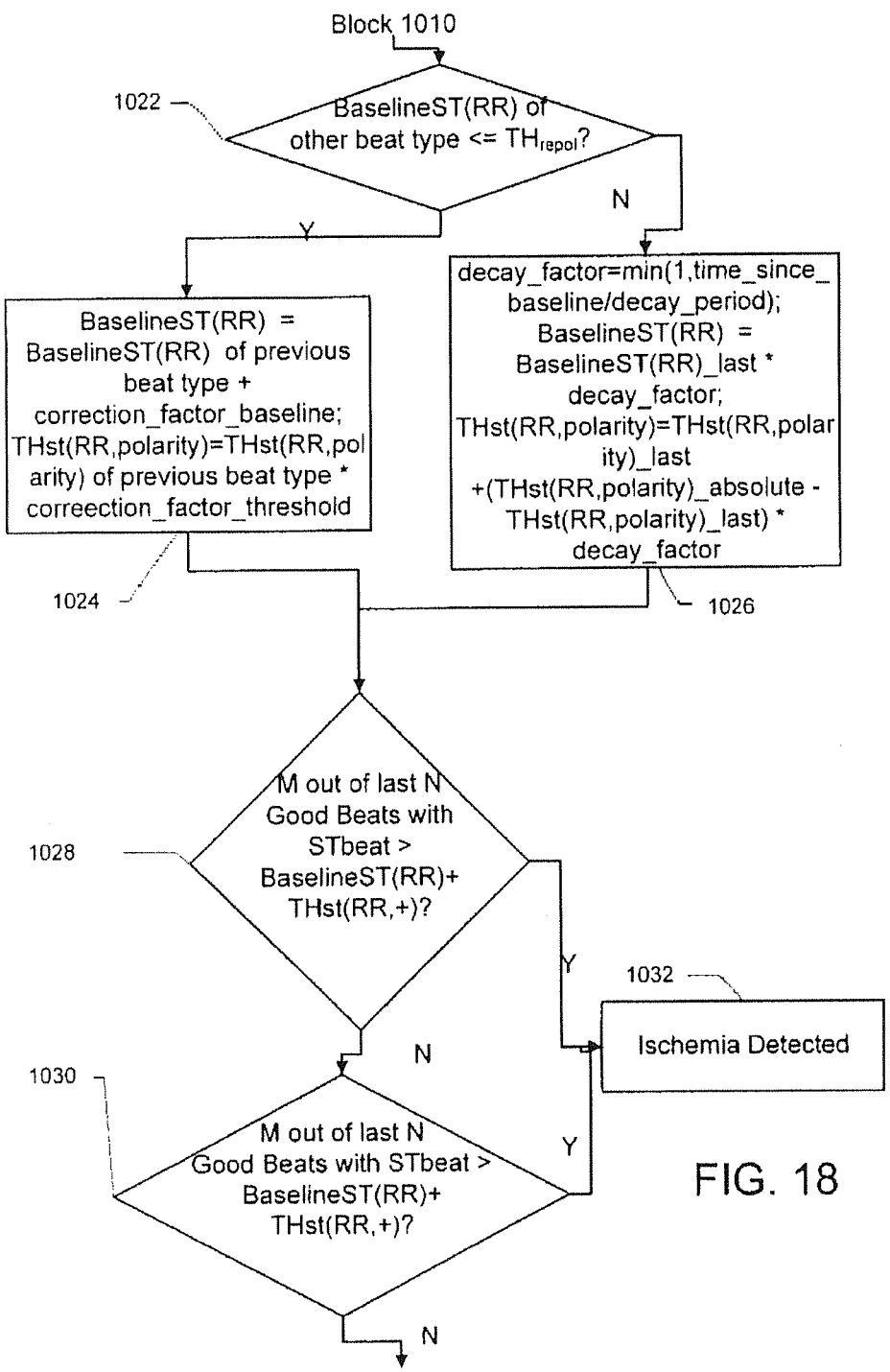
FIG. 18 shows additionally steps of a method of FIG. 17 which is used to transition between different types of beats during measurement of ischemia.

FIGS. 17 and 18 are a flow chart of an embodiment of steps 408, 418 and 419 of FIG. 15 and steps 458, 464 and 466 of FIG. 16.

At the start of this example, the ischemia detection and pacing have protocol have been active for some time. Step 1000 checks whether at least N pacing type changes have occurred within a preset interval, $TH_{pchg}$, which is preferably set to 3 minutes. In this embodiment, a pacing type change means any type of change in the cardiac conduction pathway that results in a distinct beat morphology, rather than being limited to a change in the pacing protocol itself. For example, a change from ventricular pacing to sinus rhythm is a pacing type change. However, a change from sinus rhythm to pure atrial pacing (i.e. pacing an atrium without any sequential ventricular pacing) will generally not be considered a pacing type change since the pacing is initiated in a similar fashion in both cases.

If a pacing type change has occurred within $TH_{pchg}$, then the preferred strategy is to allow ischemia checking to be performed on the new beat type for at least $TH_{pchg}$. In some cases, pacing type changes may occur very frequently (i.e. faster than the duration defined in $TH_{pchg}$). In a preferred embodiment, if there have been 2 consecutive pacing type changes within a $TH_{pchg}$ period, then control transfers to step 401 or 402 of FIG. 15 or 16, respectively, depending on which mode is currently active.

For example, if mode 1 is currently active, but there has been so much recent pacing that step 406 (FIG. 15A) has transferred control to step 408, which has in turn transferred control to steps 418/419. The combination of these steps is initiated in step 1000 of FIG. 17. If a segment of sinus rhythm has just interrupted a large number of pacing segments, then control is returned to step 401 (FIG. 15A), which will wait for enough sinus segments to invoke sinus based ischemia detection step 414. If there aren't a sufficient number of sinus segments (i.e. a large number of consecutive paced segments now occur), then step 1000 will transfer control to step 1002.

Step 1002 determines whether the majority of the beats of the current segment of a different pacing type than the previous segments. In order to avoid segments having a mixture of pacing beat types, if a pacing type change occurs within a 10—second segment, then preferably, the current segment is discarded and a new segment is immediately acquired.) This information can be obtained directly from the pacemaker circuitry. Additionally, the data collection can be made continuous until an acceptable 10-second segment of a particular pacing type is found, with a timeout occurring after 2 minutes of continuous sampling without success.

If the new segment is characterized by a majority of the same pacing type beats as the old segment, then control transfers to step 1003, which is the first part of a subroutine that detects ischemia based on the rate of change of ST segment deviation. Acute coronary occlusions result in abrupt ST segment changes that generally occur over an interval between 30s and 10 minutes. Therefore, tracking consistent ST segment deviation rates of change over this time frame can be useful for detecting ischemia.

To track these changes, a counter $\delta ST_{ctr}$, is maintained, as will be further described. In step 1006, $\delta ST_{ctr}$ is incremented if the heart rate corrected change in ST deviation between successive segments ($\delta ST$), which is calculated in step 1003, exceeds a threshold ($TH_{dst}$), as determined by step 1004. For details regarding the correction of ST segment changes based on heart rate, see U.S. patent application Ser. No. 12/461,442, entitled Heart Rate Correction System and Methods for the Detection of Cardiac Events, filed 8/2009, owned by the assignee hereof, which is incorporated by reference herein. $TH_{dst}$ is preferably set to a value that corresponds to 3%/minute for the heart rate corrected ST segment change, which is normalized according to QRS amplitude. Hereafter for the embodiment shown in this figure, all ST deviation related values will be expressed in terms of percentage of QRS amplitude. In scenarios where segments are acquired at different rates, $TH_{dst}$ is normalized according segment acquisition rate.

In step 1006, the counter is incremented by an amount LBI, which stands for "leaky bucket" increase, which is preferably set to 2. In step 1006, the segment acquisition frequency is also increased, preferably to 2 segments/minute, since the rate of change of the ST feature surpassed the $TH_{dst}$ threshold.

If $\delta ST$ is less than $TH_{dst,then}$ step 1004 transfers control to step 1014, which decrements the absolute value of $\delta ST_{ctr}$ by an amount LDB, which stands for "leaky bucket" decrease, which is preferably set to 1. By setting LBD less than LBI, $\delta ST_{ctr}$ will have better "memory" of past ST segment deviation increases, so that $\delta ST_{ctr}$ will be better able to track ST segment changes that are interrupted by temporary plateaus.

Returning to step 1006, control is transferred to step 1008, which determines whether $\delta ST_{ctr}$ has reached a threshold, which is preferably set to 5. If so, ischemia is detected in step 1016.

Otherwise, control transfers to step 1010, which begins a subroutine that tests for ischemia by comparing current ST deviation to a long term baseline similar to the manner described in U.S. patent application Ser. No. 12/367,155, entitled Baseline Processing for the Detection of Cardiac Events, filed 2/2009, owned by the assignee hereof, which is incorporated by reference herein. Step 1010 also receives control from step 1005, which resets $\delta ST_{ctr}$ in the event that the current segment represents a different pacing type than the previous segment.

Step 1010 handles cardiac memory by examining a programmable flag, as was discussed for FIG. 10B. If the flag is set to "false", cardiac memory is not examined. If the flag is set to "true", the present invention determines: (i) how long the current pacing regime has been running; and (ii) how long the previous pacing regime was running. In the preferred embodiment, both of these periods are evaluated with respect to patient specific, programmable thresholds, which are dependent on the pacing regimes (i.e., the thresholds may be different in the case of (a) a change from atrial to ventricular pacing or (b) vice versa. If the cardiac memory flag is set to on, and the current pacing regime started recently and was preceded by a long period of another type of pacing, then the baselines and expected ST deviation ranges for the current beats are not known, and step 1010 transfers control to step 1020, which checks for ischemia by detecting ischemia only if the current ST deviation exceeds relatively large absolute values (e.g. +/−35%). Alternatively, the value used for this detection may be based upon population normative values, or may be made relatively smaller if cardiac memory is altered in such a manner that the ischemia related change which is expected is less than that which occurs when no cardiac memory is present.

Assuming that the cardiac memory flag is not set to "true", control passes to step 1022, which begins a subroutine that determines both a baseline ST segment deviation and the applicable threshold to apply to determine whether a current beat is abnormally ST shifted. The subroutine selects either a baseline/threshold that is related to another beat type, or an old baseline/threshold of the same beat type. For purposes of discussion, it will be assumed that the current beat type is atrial rhythm, and that the previous beat type was a ventricular rhythm.

In FIG. 18, an RR in parenthesis (e.g, BaselineST(RR)) indicates that the corresponding parameter (e.g. BaselineST) is a (possibly constant) function of RR interval. In the preferred embodiment, BaselineST(RR) is determined at the resting heart rate, and this baseline is applied across all RR intervals in the manner described in, e.g., U.S. patent application 6,609,023. In this case, BaselinST(RR) is a constant function of RR interval. In an alternative embodiment, baselines are collected separately for each RR interval.

Step 1022 examines the value of the baseline ST deviation of ventricular paced beats. If the ventricular paced baseline ST deviation is less than or equal to a programmable threshold $TH_{repol}$, which is preferably set at +10% (can to tip lead polarity), then either the repolarization sequence is essentially normal or there is ischemia in the region of the RV apical electrode. In either case, a good correlation between the pacing and sinus ST shifts, measured by an RV apical electrode, may be assumed. The exact correlation is preferably determined empirically by measuring ST shifts in both ventricular and atrial rhythms shortly after pacemaker implantation.

The adjustment of the paced baseline and thresholds is made according to the characteristics of this correlation; the adjustment is reflected in step 1024 in the programmable correction factor baseline and correction factor threshold factors. Rather than a correlation the function which maps ST-values of ventricular rhythms to atrial rhythm, can be computed for a patient or for the population and can be used to adjust the baselines and thresholds accordingly.

Returning to step 1022, if the ST-values of the ventricular paced baseline reference data are greater than $TH_{repol}$, then the repolarization sequence is abnormal, and the correlation between ventricular and atrial ST deviation is therefore assumed to be invalid. For example, if there is an ischemic region distal to the RV apex in an area of late QRS activation (e.g. posterior), during normal sinus rhythm, the RV apex would tend to register ST elevation (can to tip lead polarity) due to the ischemia causing early repolarization of the distal tissue. However, for paced rhythms, a longer QRS period is associated with relatively delayed activation of the ischemic tissue and could allow the RV apex to repolarize relatively more during the ST segment, which would tend to reduce the ST elevation at the RV apex.

If the ventricular pacing baseline can not be applied, then step 1022 transfers control to step 1026, which determines an applicable baseline/threshold based on the old sinus rhythm baseline/threshold. The validity of the old baseline/threshold is assumed to decrease with time. To account for this, the old baseline BaselineST(RR)_last is multiplied by a decay factor (decay_factor), so that the applicable baseline (BaselineST(RR)) tends toward 0, or other selected constant, as the time since the old baseline was valid increases. Similarly, the ischemia detection thresholds increase toward large absolute values, THst(RR,polarity)_absolute, as the time since the old baseline was valid increases.

In steps 1028 and 1030, ischemia detection tests are performed using the baseline and thresholds calculated in steps 1024 or 1026, respectively.

The present invention generally describes a device which can be used to monitor patients who receive pacing therapy. An implantable device with heart pacing capability can be realized in which after the beats of the sensed data have been classified into paced or supraventricular beats, these may be compared to reference values, using beat specific parameter values and criteria, that have been based upon baseline data for each beat type. In one embodiment, baseline datasets are collected for at least two types of beats, and beats of current data are evaluated with respect to their respective baselines. The baselines for each beat type can be used to define parameters such as PQ-start, PQ-duration ST-start, ST-end, ST-duration, or ST-offset which are used to measure subsequent beats of each type which are sensed and classified by beat type and then evaluated during ischemia monitoring of the patient. Quantitative and qualitative measures can be calculated for each beat type. A measure such as ST-shift %, which is the normalized difference between a current ST-deviation and a reference ST-deviation can be calculated according to beat type. ST-Shift % can be compared to ischemic criteria, such as ischemic thresholds defined for each beat type. ST changes are not the only heart signal parameters which can be indicative of ischemia. It is also envisioned that other heart signal parameters such as QRS width, QT time and T wave amplitude may be used instead of or in addition to ST changes to allow the IMD 3/3' to accurately detect period of ischemia. In addition, the time rate of change of any of these heart signal parameters may also be used in the detection of ischemia.

In addition to paced and non-paced beats, the use of different baselines for different cardiac conditions can be used to address other ischemia monitoring scenarios as well. For example, in the case where a patient is normally medicated, but may occasionally forget medication, non-medicated and medicated baselines may be referred to so that the device can measure ischemia when sensed data indicates the patient has forgotten to take their medication. Further, cardiac state can be used to adjust ischemia detection in the case of certain abnormalities. Both LBBB and RBBB will affect the ST segment measured by the IMD 3. When this the BBB is intermittent then the use of sinus and BBB baselines may be beneficial, although the sinus baseline may also be compared to BBB beats with a correction coefficient.

In addition to ischemia other measures of cardiac status such as cardiac tone, risk of sudden cardiac death, good/bad response to medication or other intervention which may affect cardiac status can be obtained using the features of the current invention. Performing statistical operations upon the measured features of cardiac data as well as histogram analysis and trending of the measures described here is understood to be part of the current invention, as has been described previously by the current inventors.

The teachings of the present invention are applicable to beat types beyond sinus/atrial beats and ventricular beats. Most generally, the teachings of the present invention apply to any detection system that handles any number of beat types with varying electrical characteristics. For example, the present invention could be implemented to detect ischemia in the context of both RV only pacing and biventricular pacing. Further, the present invention is also applicable in cases where atrially paced beats have different electrical characteristics than sinus rhythm beats. Still further, the present invention may be applied to perform ischemia detection on both BBB beats and supraventricular beats.

Some of the steps in figures can occur earlier or later than are shown, steps can also be repeated, and steps may also be omitted altogether. The steps of the particular methods shown here can be incorporated into variants of other methods which are shown. Various other modifications, adaptations, and alternative designs are of course possible in light of the above teachings. Therefore, it should be understood at this time that, within the scope of the appended claims, the invention can be practiced otherwise than as specifically described herein.

We claim:

1. An implantable device with ischemia detection and heart pacing capability, including:
    at least one electrode adapted for implantation in a body;
    circuitry coupled to the electrode to sense signals therefrom and to generate corresponding digital signals;
    pacemaker circuitry;
    a processor configured to:
        distinguish between at least two beat types, including ventricularly paced and supraventricular beats;
        collect the values of a heart signal parameter from the digital signals for ventricularly paced beats during a first time period;
        count the number of ventricularly paced beats during the first time period;
        if the number of ventricularly paced beats during the first time period is insufficient to establish a ventricularly paced baseline, direct the pacemaker circuitry to pace the heart for a second time period, the second time period being sufficiently long so that a ventricularly paced baseline can be established;
        derive a ventricularly paced baseline for the heart signal parameter, wherein the ventricularly paced baseline is indicative of a normal value of the heart signal parameter and wherein the ventricularly paced baseline is based at least in part on a plurality of values of the heart signal parameter collected during the second time period;
        measure the value of the heart signal parameter for ventricularly paced beats over a third time period; and
        identify ischemic beats by the application of ischemia detection criteria to the comparison of the values of the heart signal parameter for ventricularly paced beats over the third time period to the ventricularly paced baseline.

2. The device of claim 1 further including the derivation of a baseline of the at least one heart signal parameter for supraventricular beats.

3. The device of claim 2 wherein the processor is further configured to apply separate ischemia detection criteria to identify ischemic beats for ventricularly paced and supraventricular beats.

4. The device of claim 3 wherein the processor is further configured to identify ischemic events by counting ischemic beats of either type operative when a sufficient number of such beats exist within a specified interval.

5. The device of claim 2, wherein the processor is further configured to use baseline data for each beat type to determine an ischemia threshold for assessing each type of beat.

6. The device of claim 2, wherein the processor is further configured to use the baseline for each beat type to adjust parameters for measuring features for each type of beat.

7. The device of claim 2 wherein the adaptive reference baselines for the ventricularly paced and the supraventricular beats pertain to the same cardiac feature.

8. The device of claim 1 wherein the second time period is such that the total number of paced beats from the first and second time periods is greater than the pre-set minimum number of beats.

9. The device of claim 1 wherein the number of ventricularly paced beats during the first time period is determined to be insufficient to establish a ventricularly paced baseline if that number is less than a pre-set number of beats.

10. The device of claim 9 wherein the minimum number of beats is 10 beats.

11. The device of claim 9 wherein the minimum number of beats is 100 beats.

12. The device of claim 1 wherein the heart signal parameter is the ST segment value determined from the voltage of one or more portions of the ST segment of the electrical signals of the heart.

13. The device of claim 12 wherein the processor is further configured to measure an ST segment value for a particular beat type in a different manner according to the type of beat.

14. The device of claim 1, wherein the processor is further configured to apply data acceptance criteria for at least one beat type and to reject data that does not meet the data acceptance criteria from being used as baseline data.

15. The device of claim 1, wherein the processor is further configured to operate to sense cardiac data and collect the baseline data for paced-beat baselines when pacing occurs if baseline data is needed even if this pacing occurs during a time when collection of data segments is not normally scheduled to occur.

* * * * *